US012584141B2

(12) United States Patent
Guo et al.

(10) Patent No.: US 12,584,141 B2
(45) Date of Patent: Mar. 24, 2026

(54) METHOD FOR IMPROVING WHEAT RESISTANCE TO FUSARIUM HEAD BLIGHT (FHB) BY GENOME EDITING

(71) Applicant: Northwest A&F University, Xianyang (CN)

(72) Inventors: Jun Guo, Xianyang (CN); Fuxin He, Xianyang (CN); Zhensheng Kang, Xianyang (CN); Huilin Sun, Xianyang (CN); Xingxuan Bai, Xianyang (CN); Ce Wang, Xianyang (CN); Yanfeng Wang, Xianyang (CN)

(73) Assignee: Northwest A&F University (CN)

( * ) Notice: Subject to any disclaimer, the term of this patent is extended or adjusted under 35 U.S.C. 154(b) by 236 days.

(21) Appl. No.: 18/558,619

(22) PCT Filed: Dec. 29, 2022

(86) PCT No.: PCT/CN2022/143089
§ 371 (c)(1),
(2) Date: Nov. 2, 2023

(87) PCT Pub. No.: WO2023/241004
PCT Pub. Date: Dec. 21, 2023

(65) Prior Publication Data
US 2025/0101450 A1      Mar. 27, 2025

(30) Foreign Application Priority Data
Jun. 15, 2022    (CN) .......................... 202210674184.4

(51) Int. Cl.
*C12N 15/82*        (2006.01)
(52) U.S. Cl.
CPC ..... *C12N 15/8282* (2013.01); *C12N 15/8213* (2013.01); *C12N 2310/20* (2017.05)

(58) Field of Classification Search
None
See application file for complete search history.

(56) References Cited

PUBLICATIONS

Deng et al. Ectopic expression of wheat TaCIPK14, encoding a calcineurin B-like protein-interacting protein kinase, confers salinity and cold tolerance in tobacco. Physiologia Plantarum 149: 367-377. 2013; Published Feb. 22, 2013 (Year: 2013).*
Kurusu et al. Regulation of Microbe-Associated Molecular Pattern-Induced Hypersensitive Cell Death, Phytoalexin Production, and Defense Gene Expression by Calcineurin B-Like Protein-Interacting Protein. Plant Physiology, Jun. 2010, vol. 153, pp. 678-692; Published Mar. 31, 2010 (Year: 2010).*
Brauer et al. Genome Editing of a Deoxynivalenol-Induced Transcription Factor Confers Resistance to *Fusarium graminearum* in Wheat. MPMI vol. 33, No. 3, 2020, pp. 553-560; Published Nov. 27, 2019 (Year: 2019).*

* cited by examiner

*Primary Examiner* — Anne Kubelik
*Assistant Examiner* — Keith R. Williams
(74) *Attorney, Agent, or Firm* — Lerner David LLP

(57)          ABSTRACT
A method for improving wheat resistance to *Fusarium* head blight (FHB) by genome editing is provided, and further provided is use of TaCIPK14 protein or related biomaterial thereto in the regulation of plant resistance to FHB; the TaCIPK14 protein is TaCIPK14-4A protein (SEQ ID NO: 4), TaCIPK14-4B protein (SEQ ID NO: 5), and/or TaCIPK14-4D protein (SEQ ID NO: 6). TaCIPK14 knockout mutant plants are successfully obtained by simultaneously editing three alleles of TaCIPK14 in wheat using CRISPR-Cas9 gene editing technology. The TaCIPK14 knockout mutant shows resistance to inoculation with FHB pathogens, and the results of evaluation of major agronomic traits confirm that the TaCIPK14 knockout mutant reserves the major agronomic traits.

13 Claims, 14 Drawing Sheets

Specification includes a Sequence Listing.

TaCIPK14-4A  ATGGCAAACAGAGGGAAGATTCTAATGGAGCGGTACGAGCTGGGAAGATT  50
TaCIPK14-4B  ATGGCAAACAGAGGGAAGATTCTAATGGAGCGGTACGAGCTGGGAAGATT  50
TaCIPK14-4D  ATGGCAAACAGAGGGAAGATTCTAATGGAGCGGTACGAGCTGGGAAGATT  50

TaCIPK14-4A  GTTGGGGAAAGGAACATTTGGCAAGGTACACTATGCAAGGAGCCTAGAGT  100
TaCIPK14-4B  GTTGGGGAAAGGAACATTCGGCAAGGTGCACTATGCAAGGAGCCTAGAGT  100
TaCIPK14-4D  GTTGGGGAAAGGAACATTCGGCAAGGTGCACTATGCAAGGAGCCTAGAGT  100

TaCIPK14-4A  CGAACCGAAGCGTCGCCATAAAGATGCTGGACAAGGAGAAGGTGCTCAAG  150
TaCIPK14-4B  CGAACCAAAGCGTCGCCATAAAGATGCTGGACAAGGAGAAGGTGCTCAAG  150
TaCIPK14-4D  CGAACCGAAGCGTCGCCATAAAGATGCTGGACAAGGAGAAGGTGCTCAAG  150

TaCIPK14-4A  GTTGGGCTCTCGGAGCAAATCAGGCGTGAGGTCACAACCATGCGGTTGGT  200
TaCIPK14-4B  GTTGGGCTCTCGGAGCAAATCAGGCGTGAGGTCACAACCATGCGGCTGGT  200
TaCIPK14-4D  GTTGGGCTCTCGGAGCAAATCAGGCGTGAGGTCACAACCATGCGGTTGGT  200 gRNA1 target   PAM

TaCIPK14-4A  GGCACACAAGAACATTGTTCAGCTTCATGAGGTCATGGCGACACGAAACA  250
TaCIPK14-4B  GGCACACAAGAACATTGTTCAGCTTCATGAGGTCATGGCGACACGAAACA  250
TaCIPK14-4D  GGCACACAAGAACATTGTTCAGCTTCATGAGGTCATGGCGACACGAAACA  250

TaCIPK14-4A  AAATATACTTTGTCATGGAGTATGTGAAAGGCGGTGAGCTCTTTGACAAG  300
TaCIPK14-4B  AAATATACTTTGTCATGGAGTATGTGAAAGGCGGTGAGCTCTTTGACAAG  300
TaCIPK14-4D  AAATATACTTTGTCATGGAGTATGTGAAAGGCGGTGAGCTCTTTGACAAG  300 gRNA2 target    PAM

TaCIPK14-4A  GTTGCAAAGAGTGGCAAGCTCACAGAGGGTGCTGCACATAAGTATTTCCA  350
TaCIPK14-4B  GTTGCAAAGAGTGGCAAGCTCACAGAGGGTGCTGCACATAAGTATTTCCA  350
TaCIPK14-4D  GTTGCAAAGAGTGGCAAGCTCACAGAGGGTGCTGCACATAAGTATTTCCA  350

TaCIPK14-4A  GCAGCTCATCAGTGCAGTGGATTACTGCCACAGCCAAGGCGTGTATCACC  400
TaCIPK14-4B  GCAGCTCATCAGTGCAGTGGATTACTGCCACAGCCAAGGCGTGTATCACC  400
TaCIPK14-4D  GCAGCTCATCAGTGCAGTGGATTACTGCCACAGCCAAGGCGTGTATCACC  400

TaCIPK14-4A  GGGATCTCAAGCTGGAGAACCTGCTCCTGGATGAGAATGAGAACCTTAAG  450
TaCIPK14-4B  GGGATCTCAAGCTGGAGAACCTGCTCCTGGATGAGAATGAGAACCTTAAG  450
TaCIPK14-4D  GGGATCTCAAGCTGGAGAACCTGCTCCTGGATGAGAATGAGAACCTTAAG  450

TaCIPK14-4A  GTCTCGGATTTTGGATTGAGCGCACTTTCAGAGTCAAAGAGGCAAGATGG  500
TaCIPK14-4B  GTCTCAGATTTTGGACTGAGCGCACTTTCAGAGTCAAAGAGGCAAGATGG  500
TaCIPK14-4D  GTCTCGGATTTTGGATTGAGCGCCCTTTCAGAGTCAAAGAGGCAAGATGG  500

FIG. 1A

```
TaCIPK14-4A   CTTGCTGCACACCACCTGCGGAACACCCGCATATGTAGCTCCGGAGGTCA   550
TaCIPK14-4B   CTTGCTCCACACCACCTGCGGAACACCTGCATATGTAGCTCCGGAGGTCA   550
TaCIPK14-4D   CTTGCTCCACACCACCTGCGGAACACCCGCATATGTAGCTCCGGAGGTCA   550

TaCIPK14-4A   TCAGCAAGACAGGTTATGATGGTGCGAAATCAGATATCTGGTCTTGTGGT   600
TaCIPK14-4B   TCAGCAAGACAGGTTACGATGGTGCGAAATCAGATATCTGGTCTTGTGGT   600
TaCIPK14-4D   TCAGCAAGACAGGTTACGATGGTGCAAAATCAGATATCTGGTCTTGTGGT   600

TaCIPK14-4A   GTTATCCTTTTTGTTCTTGTTGCTGGTTATCTCCCTTTCCATGGTTCCAA   650
TaCIPK14-4B   GTTATCCTTTTTGTTCTTGTTGCTGGTTATCTCCCTTTCCATGGTTCCAA   650
TaCIPK14-4D   GTTATCCTTTTTGTTCTTGTTGCTGGTTATCTCCCTTTCCATGGTTCCAA   650

TaCIPK14-4A   CTTGATGGACATGTACCGGAAGATTGAGCAAGGAGATTTCAGGTGCCCCA   700
TaCIPK14-4B   CTTGATGGACATGTACCGGAAGATTGAACAAGGAGATTTCAGGTGCCCCA   700
TaCIPK14-4D   CTTGATGGACATGTACCGGAAGATTGAGCAAGGAGATTTCAGGTGCCCCG   700

TaCIPK14-4A   GCTGGTTCTCACACAAACTCCAGAAGCTCTTGTTCAAGATTCTGGACCCC   750
TaCIPK14-4B   GCTGGTTCTCACACAAACTCCAGAAGCTCTTGTGCAAGATCCTGGACCCC   750
TaCIPK14-4D   GCTGGTTCTCACACAAACTCCAGAAGCTCTTGCTCAAGATCCTGGACCCC   750

TaCIPK14-4A   AATCCAAGCACCAGGGCATCTATCCAGAAGATAAAAGAGTCTACCTGGTT   800
TaCIPK14-4B   AATCCAAGCACCAGGGCATCTATCCAGAAGATAAAAGAGTCTACCTGGTT   800
TaCIPK14-4D   AATCCAAGCACCAGGGCATCTATCCAGAAGATAAAAGAGTCTACCTGGTT   800

TaCIPK14-4A   CCGGAAAGGTCCAAGGGGAACCCTTGCAGTGAAGGAGAGAACTCCCAGTG   850
TaCIPK14-4B   TCGGAAAGGTCCAAGGGGCACCCTTGCAGTGAAGGAGAGAACTCCCAGTG   850
TaCIPK14-4D   CCGGAAAGGTCCAAGGGGCACCCTTGCAGTGAAGGAGAGAACTCCCAGTG   850

TaCIPK14-4A   AGAACGTCACCACAAATGCTCCTCCTACAGCTGGTGTGAGGCCAAGGAAG   900
TaCIPK14-4B   AGAATGTCACCACAAATGCTCCTCCTACAGCTGGTGTGAGGCCAAGGAAG   900
TaCIPK14-4D   AGAATGTCATCACAAATGCTCCTCCTACAGCTGGTGTGAGGCCAAGGAAG   900

TaCIPK14-4A   AACACTCATGAAGATGTGAAGCCCCTGATGGTGACAAACTTAAATGCCTT   950
TaCIPK14-4B   AACACTCATGAAGATGTGCAGCCCCTGACGGTGACAAACTTAAATGCCTT   950
TaCIPK14-4D   AACACTCATGAAGATGTGAAGCCCCTCATGGTGACAAACTTAAATGCCTT   900

TaCIPK14-4A   TGAGATCATCTCCTTCTCCACGGGGTTTGACCTGTCTGGCCTATTCATCC   1000
TaCIPK14-4B   TGAGATCATCTCCTTCTCCACGGGGTTTGACCTGTCCGGCCTATTCATCC   1000
TaCIPK14-4D   TGAGATCATCTCCTTCTCCACGGGGTTTGACCTGTCCGGCCTATTCATCC   1000
```

FIG. 1B

```
TaClPK14-4A  GAGAGGAGTGCAGAAAGGAGACAAGGTTCACTTCAGACAAGCCTGCTTCA  1050
TaClPK14-4B  AAGAGGACTGCAGAAAGGAGACAAGGTTCACTTCAGACAAGCCTGCTTCA  1050
TaClPK14-4D  AAGAGGACTGCAGAAAGGAGACAAGGTTCACTTCAGACAAGCCTGCTTCA  1050

TaClPK14-4A  GCCATCATCTCGAAGCTGGAATATGTTGCGAAAGCGCTGAATCTCAGGGT  1100
TaClPK14-4B  GCCATCATCTCGAAGCTGGAATACGTTGCAAAGGCGCTGAATCTCAGGGT  1100
TaClPK14-4D  ACCATCATCTCGAAGCTGGAATATGTTGCGAAGGCGCTGAATCTCAGGGT  1100

TaClPK14-4A  AAGGAAGAAGGACATGGCGTGGTGAAGATGCAAGCGACCAAGGAAGGAA   1150
TaClPK14-4B  AAGGAAGAAGGACATGGTGTGGTGAAGATGCAAGCAACCAAGGAGGGAA   1150
TaClPK14-4D  AAGGAAGAAGGACATGGCGTGGTGAAGATGCAAGCGACCAAGGAGGGAA   1150

TaClPK14-4A  GGAATGGTGCTGTTCAGYYAGACAYGGAGATCTTCGAGATCACACCTTCC  1200
TaClPK14-4B  GGAATGGTGCTGTTCAGYYAGACAYGGAGATCTTCGAGATCACACCTTCC  1200
TaClPK14-4D  GGAATGGTGCTGTACAGYYAGACAYGGAGATCTTCGAGATCACACCTTCC  1200

TaClPK14-4A  CACCACCTCATTGAGATGAAACAAACAAGTGGTGATCCACTGGAGTACCG  1250
TaClPK14-4B  CACCACCTCATTGAGATGAAACAAACAAGTGGTGATCCGCTGGAGTACCG  1250
TaClPK14-4D  CACCACCTCATTGAGATGAAACAAACAAGTGGTGATCCGCTGGAGTACCG  1250

TaClPK14-4A  GGAGCTATTGGAGGACATCCGGCCAGCGCTGAAGGACATAGTCTGGGCCT  1300
TaClPK14-4B  GGAGCTATTGGAGGACATCCGGCCAGCGCTGAAGGACATAGTCTGGGCCT  1300
TaClPK14-4D  GGAGCTATTGGAGGACATCCGGCCAGCGCTGAAGGACATAGTCTGGGCCT  1300

TaClPK14-4A  GGCACGGAGATGACCACCACCAGCAGCTAGAGTAG                 1335
TaClPK14-4B  GGCACGGAGATGACCACCAGCAGCAGCTAGAGTAG                 1335
TaClPK14-4D  GGCACGGAGATGACCACCAGCAGCAGCTAGAGTAG                 1335
```

FIG. 1C

Kinase catalyzation domain                    *

| | | |
|---|---|---|
| TaClPK14-4A | MANRGKILMERTELGRLLGKGTFGKVHYARSLESNRSVAIKMLDKEKVLK | 50 |
| TaClPK14-4B | MANRGKILMERTELGRLLGKGTFGKVHYARSLESNRSVAIKMLDKEKVLK | 50 |
| TaClPK14-4D | MANRGKILMERTELGRLLGKGTFGKVHYARSLESNQSVAIKMLDKEKVLK | 50 |

Kinase catalyzation domain

| | | |
|---|---|---|
| TaClPK14-4A | VGLSEQIRREVTTMRLVAHKNIVQLHEVMATRNKIYFVMEYVKGGELFDK | 100 |
| TaClPK14-4B | VGLSEQIRREVTTMRLVAHKNIVQLHEVMATRNKIYFVMEYVKGGELFDK | 100 |
| TaClPK14-4D | VGLSEQIRREVTTMRLVAHKNIVQLHEVMATRNKIYFVMEYVKGGELFDK | 100 |

Kinase catalyzation domain

| | | |
|---|---|---|
| TaClPK14-4A | VAKSGKLTEGAAHKYFQQLISAVDYCHSQGVTHRDLKLENLLLDENENLK | 150 |
| TaClPK14-4B | VAKSGKLTEGAAHKYFQQLISAVDYCHSQGVTHRDLKLENLLLDENENLK | 150 |
| TaClPK14-4D | VAKSGKLTEGAAHKYFQQLISAVDYCHSQGVTHRDLKLENLLLDENENLK | 150 |

| | | |
|---|---|---|
| TaClPK14-4A | VSDFGLSALSESKRQDGLLHTTCGTPAYVAPEVISKTGYDGAKSDIWSCG | 200 |
| TaClPK14-4B | VSDFGLSALSESKRQDGLLHTTCGTPAYVAPEVISKTGYDGAKSDIWSCG | 200 |
| TaClPK14-4D | VSDFGLSALSESKRQDGLLHTTCGTPAYVAPEVISKTGYDGAKSDIWSCG | 200 |

Activation loop        Kinase catalyzation domain

| | | |
|---|---|---|
| TaClPK14-4A | VILFVLVAGYLPFHGSNLMDMYRKIEQGDFRCPSWFSHKLQKLLFKILDP | 250 |
| TaClPK14-4B | VILFVLVAGYLPFHGSNLMDMYRKIEQGDFRCPGWFSHKLQKLLLKILDP | 250 |
| TaClPK14-4D | VILFVLVAGYLPFHGSNLMDMYRKIEQGDFRCPSWFSHKLQKLLCKILDP | 250 |

Kinase catalyzation domain

| | | |
|---|---|---|
| TaClPK14-4A | NPSTRASIQKIKESTWFRKGPRGTLAVKERTPSENVTTNAPPTAGVRPPK | 300 |
| TaClPK14-4B | NPSTRASIQKIKESTWFRKGPRGTLAVKERTPSENVITNAPPTAGVRPPK | 300 |
| TaClPK14-4D | NPSTRASIQKIKESTWFRKGPRGTLAVKERTPSENVTTNAPPTAGVRPPK | 300 |

Rgulatory domain

| | | |
|---|---|---|
| TaClPK14-4A | NTHEDVKPLMVTNLNAFEIISFSTGFDLSGLFREECRKETRFTSDKPAS | 350 |
| TaClPK14-4B | NTHEDVKPLMVTNLNAFEIISFSTGFDLSGLFQEDCRKETRFTSDKPAS | 350 |
| TaClPK14-4D | NTHEDVQPLTVTNLNAFEIISFSTGFDLSGLFQEDCRKETRFTSDKPAS | 350 |

NAF/FISL        Rgulatory domain

| | | |
|---|---|---|
| TaClPK14-4A | AIISKLEYVAKALNLRVRKKDNGVVKMQARKEGRNGAVQLDMEIFEITPS | 400 |
| TaClPK14-4B | TIISKLEYVAKALNLRVRKKDNGVVKMQARKEGRNGAVQLDMEIFEITPS | 400 |
| TaClPK14-4D | AIISKLEYVAKALNLRVRKKDNGVVKMQARKEGRNGAVQLDMEIFEITPS | 400 |

PPI
Rgulatory domain

| | | |
|---|---|---|
| TaClPK14-4A | HHLIEMKQTSGDPLEYRELLEDIRPALKDIVWAWHGDDHHQQLE | 444 |
| TaClPK14-4B | HHLIEMKQTSGDPLEYRELLEDIRPALKDIVWAWHGDDHQQLE | 444 |
| TaClPK14-4D | HHLIEMKQTSGDPLEYRELLEDIRPALKDIVWAWHGDDHQQLE | 444 |

FIG. 2

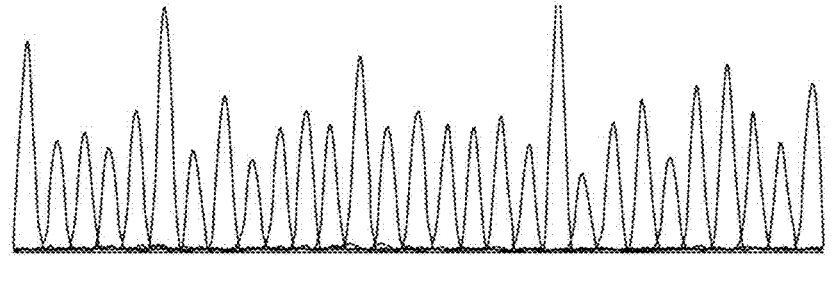
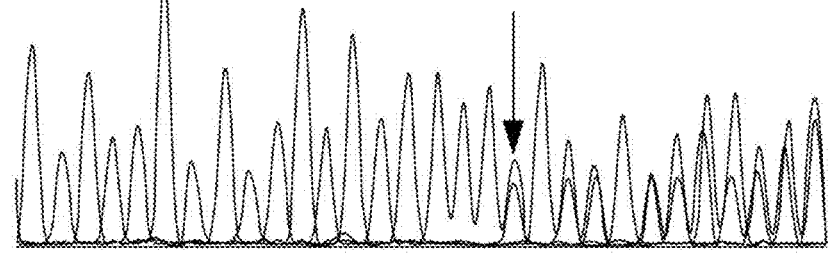
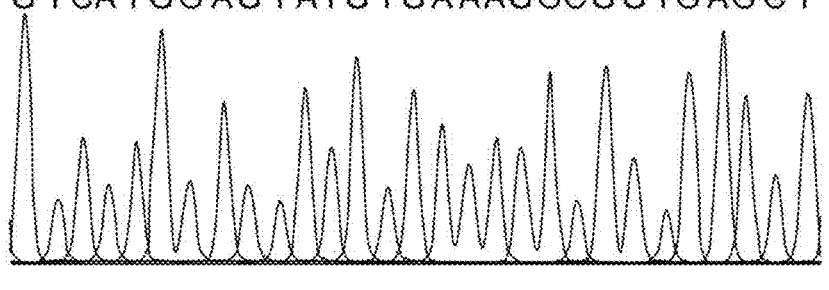
FIG. 5A

FIG. 5C

*TaCIPK14-4A*
gRNA1 target  PAM
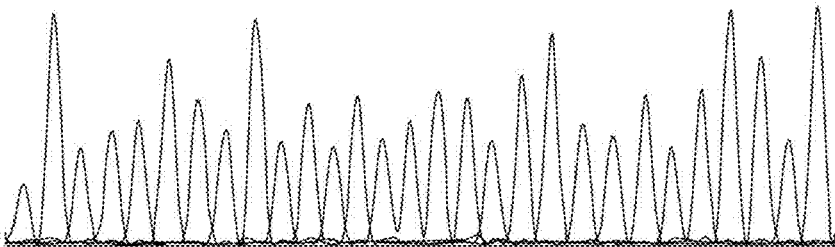
Fielder
G G C G T G A G G T C A C A A C C A T G C G G T T G G T G
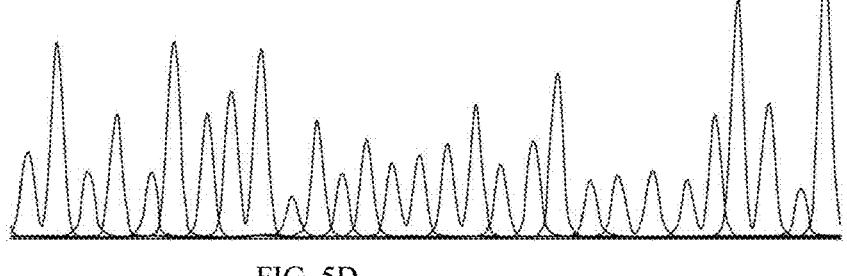
T₀-21
G G C G T G A G G T C A C A A C C A T G C G G T T G G T G
FIG. 5D
*TaCIPK14-4B*
gRNA1 target  PAM
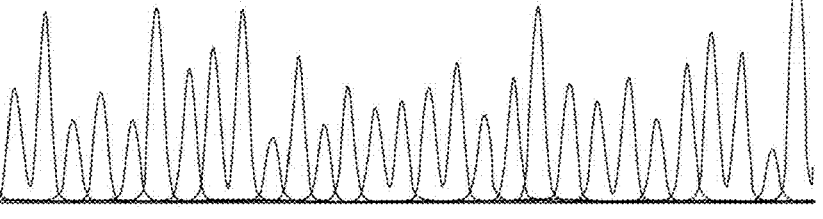
Fielder
G G C G T G A G G T C A C A A C C A T G C G G C T G G T G
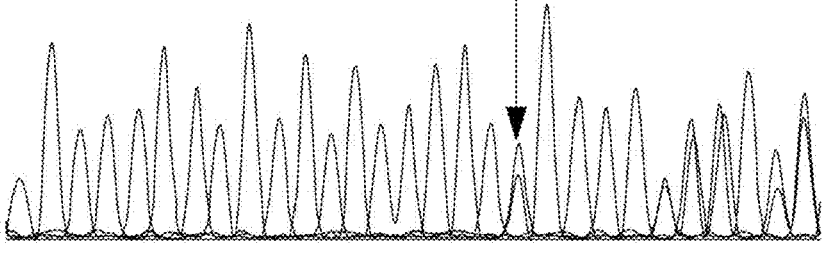
T₀-21
G G C G T G A G G T C A C A A C C A T G C G G T G G G C T
FIG. 5E

*TaCIPK14-4D*
gRNA1 target  PAM
GGCGTGAGGTCACAACCATGCGGTTGGTG
Fielder
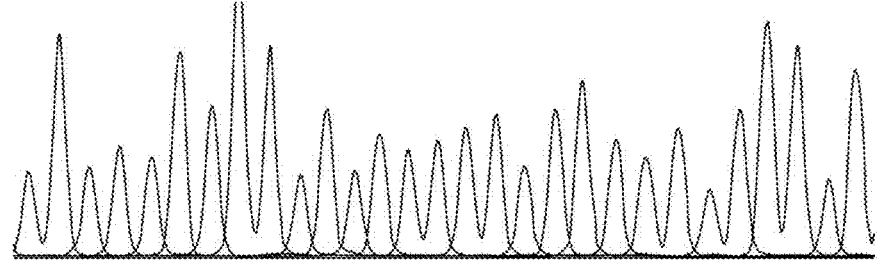
GGCGTGAGGTCGTTGGTGGCACACAAGAA
$T_0$-21
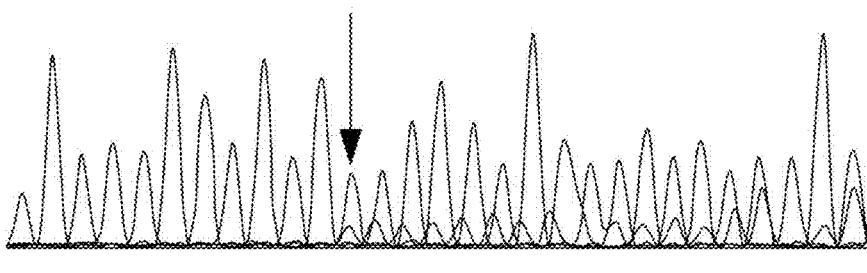
FIG. 5F

FIG. 6

|  | Deduced amino acid sequences | Length |
|---|---|---|

Fielder  A    ---//---IRREVTTMRLVAHKNIVQLHEVMATRNKIYFVMEYVKGGELFDKVAK
SGKLTEGAAHKYFQQLISAVDYCHSQGVYHRDLKLENLLLDENENLKVSDFGLSALSE---//---  444

Fielder  B    ---//---IRREVTTMRLVAHKNIVQLHEVMATRNKIYFVMEYVKGGELFDKVAK
SGKLTEGAAHKYFQQLISAVDYCHSQGVYHRDLKLENLLLDENENLKVSDFGLSALSE---//---  444

Fielder  D    ---//---IRREVTTMRLVAHKNIVQLHEVMATRNKIYFVMEYVKGGELFDKVAK
SGKLTEGAAHKYFQQLISAVDYCHSQGVYHRDLKLENLLLDENENLKVSDFGLSALSE---//---  444

KO-1 A    ---//---IRREVTTMRLVAHKNIVQLHEVMATRNKIYFVMEYVKRR*----------------  95
KO-1 B    ---//---IRREVTTMRLVAHKNIVQLHEVMATRNKIYFVME*----------------------  90
KO-1 D    ---//---IRREVTTMRLVAHKNIVQLHEVMATRNKIYFVMEYRR*------------------  93

KO-2 A    ---//---IRREVTTMRLVAHKNIVQLHEVMATRNKIYFVMEYVKRR*----------------  95
KO-2 B    ---//---IRREVTTMRLVAHKNIVQLHEVMATRNKIYFVMEYVKRR*----------------  95
KO-2 D    ---//---IRREVTTMRLVAHKNIVQLHEVMATRNKIYFVMEYRR*------------------  93

KO-3 A    ---//---IRREVTTMRLVAHKNIVQLHEVMATRNKIYFVMEYVKRR*----------------  95
KO-3 B    ---//---IRREVTTMRLVAHKNIVQLHEVMATRNKIYFVME*---------------------  90
KO-3 D    ---//---IRREVTTMRLVAHKNIVQLHEVMATRNKIYFVMEYVKAVSSLTRLQRVA
SSQRVLHISISSSSSVQWITATAKACITGISSWRTCSWMRMRTLRSRILD*-----------  155

KO-4 A    ---//---IRREVTTMRLVAHKNIVQLHEVMATRNKIYFVMEYVKRR*----------------  95
KO-4 B    ---//---IRREVTTRR*-----------------------------------------------  65
KO-4 D    ---//---IRREVVGGTQEHCSAS*----------------------------------------  72

KO-5 A    ---//---IRREVTTMRLVAHKNIVQLHEVMATRNKIYFVMEYVKRR*----------------  95
KO-5 B    ---//---IRREVTTMRLVAHKNIVQLHEVMATRNKIYFVMEYVKRR*----------------  95
KO-5 D    ---//---IRREVVGGTQEHCSAS*----------------------------------------  72

FIG. 7

SEQUENCE LISTING

```
Sequence total quantity: 134
SEQ ID NO: 1          moltype = DNA  length = 1335
FEATURE               Location/Qualifiers
source                1..1335
                      mol_type = other DNA
                      note = TaCIPK14-4A
                      organism = Triticum aestivum
```

```
CDS                     1..1335
                        protein_id = 4
                        translation = MANRGKILMERYELGRLLGKGTFGKVHYARSLESNRSVAIKMLDKE
                            KVLKVGLSEQIRREVTTMRLVAHKNIVQLHEVMATRNKIYFVMEYVKGGELFDKVAKSG
                            KLTEGAAHKYFQQLISAVDYCHSQGVYHRDLKLENLLLDENENLKVSDFGLSALSESKR
                            QDGLLHTTCGTPAYVAPEVISKTGYDGAKSDIWSCGVILFVLVAGYLPFHGSNLMDMYR
                            KIEQGDFRCPSWFSHKLQKLLFKILDPNPSTRASIQKIKESTWFRKGPRGTLAVKERTP
                            SENVTTNAPPTAGVRPRKNTHEDVKPLMVTNLNAFEIISFSTGFDLSGLFIREECRKET
                            RFTSDKPASAIISKLEYVAKALNLRVRKKDNGVVKMQARKEGRNGAVQLDMEIFEITPS
                            HHLIEMKQTSGDPLEYRELLEDIRPALKDIVWAWHGDDHHQQLE
SEQUENCE: 1
atggcaaaca gagggaagat tctaatggag cggtacgagc tgggaagatt gttggggaaa    60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaag cggtgagct ctttgacaag    300
gttgcaaaga gtggcaagct cacagagggt gctgcacata agtatttcca gcagctcatc   360
agtgcagtgg attactgcca cagccaaggc gtgtatcacc gggatctcaa gctggagaac   420
ctgctcctgg atgagaatga gaaccttaag gtctcggatt ttggattgag cgcactttca   480
gagtcaaaga ggcaagatgg cttgctgcac accacctgcg gaacaccgc atatgtagct    540
ccggaggtca tcagcaagac aggttatgat ggtgcgaaat cagatatctg gtcttgtggt   600
gttatccttt ttgttcttgt tgctggttat ctcccttttcc atggttccaa cttgatggac   660
atgtaccgga agattgagca aggagatttc aggtgcccca gctggttctc acacaaactc   720
cagaagctct tgttcaagat tctgacccc aatccaagca ccagggcatc tatccagaag    780
ataaaagagt ctacctggtt ccggaaaggt ccaaggggaa cccttgcagt gaaggagaga   840
actcccagtg agaacgtcac cacaaatgct cctcctacag ctggtgtgag gccaaggaag   900
aacactcatg aagatgtgaa gcccctgatg gtgacaaact aaatgcctt tgagatcatc    960
tccttctcca cggggtttga cctgtctggc ctattcatcc gagaggagtg cagaaaggag  1020
acaaggttca cttcagacaa gcctgcttca gccatcatct cgaagctgga atatgttgcg  1080
aaagcgctga atctcagggt aaggaagaag gacaatggcg tggtgaagat gcaagcgagg  1140
aaggaaggaa ggaatggtgc tgttcagtta gacatggaga tcttcgagat cacaccttcc  1200
caccacctca ttgagatgaa acaaacaagt ggtgatccac tggagtaccg ggagctattg  1260
gaggacatcc ggccagcgct gaaggacata gtctgggcct ggcacggaga tgaccaccac  1320
cagcagctag agtag                                                    1335

SEQ ID NO: 2             moltype = DNA   length = 1335
FEATURE                  Location/Qualifiers
source                   1..1335
                         mol_type = other DNA
                         note = TaCIPK14-4B
                         organism = Triticum aestivum
CDS                      1..1335
                         protein_id = 5
                         translation = MANRGKILMERYELGRLLGKGTFGKVHYARSLESNQSVAIKMLDKE
                             KVLKVGLSEQIRREVTTMRLVAHKNIVQLHEVMATRNKIYFVMEYVKGGELFDKVAKSG
                             KLTEGAAHKYFQQLISAVDYCHSQGVYHRDLKLENLLLDENENLKVSDFGLSALSESKR
                             QDGLLHTTCGTPAYVAPEVISKTGYDGAKSDIWSCGVILFVLVAGYLPFHGSNLMDMYR
                             KIEQGDFRCPSWFSHKLQKLLCKILDPNPSTRASIQKIKESTWFRKGPRGTLAVKERTP
                             SENVTTNAPPTAGVRPRKNTHEDVQPLTVTNLNAFEIISFSTGFDLSGLFIQEDCRKET
                             RFTSDKPASAIISKLEYVAKALNLRVRKKDNGVVKMQARKEGRNGAVQLDMEIFEITPS
                             HHLIEMKQTSGDPLEYRELLEDIRPALKDIVWAWHGDDHQQQLE
SEQUENCE: 2
atggcaaaca gagggaagat tctaatggag cggtacgagc tgggaagatt gttggggaaa    60
ggaacattcg gcaaggtgca ctatgcaagg agcctagagt cgaaccaaag cgtcgccata   120
aagatgctgg acaaggagaa ggtgctcaag gttgggctct cggagcaaat caggcgtgag   180
gtcacaacca tgcggctggt ggcacacaag aacattgttc agcttcatga ggtcatggcg   240
acacgaaaca aaatatactt tgtcatggag tatgtgaaag cggtgagct ctttgacaag    300
gttgcaaaga gtggcaagct cacagagggt gctgcacata agtatttcca gcagctcatc   360
agtgcagtgg attactgcca gccaaggc gtgtatcacc gggatctcaa gctggagaac    420
ctgctcctgg atgagaatga gaaccttaag gtctcagatt ttggactgag cgcactttca   480
gagtcaaaga ggcaagatgg cttgctccac accacctgcg gaacacctgc atatgtagct   540
ccggaggtca tcagcaagac aggttacgat ggtgcgaaat cagatatctg gtcttgtggt   600
gttatccttt ttgttcttgt tgctggttat ctcccttttcc atggttccaa cttgatggac   660
atgtaccgga agattgaaca aggagatttc aggtgcccca gctggttctc acacaaactc   720
cagaagctct tgtgcaagat cctgacccc aatccaagca ccagggcatc tatccagaag    780
ataaaagagt ctacctggtt tcggaaaggt ccaaggggca cccttgcagt gaaggagaga   840
actcccagtg agaatgtcac cacaaatgct cctcctacag ctggtgtgag gccaaggaag   900
aacactcatg aagatgtgca gcccctgacg gtgacaaact aaatgcctt tgagatcatc    960
tccttctcca cggggtttga cctgtccggc ctattcatcc aagaggactg cagaaaggag  1020
acaaggttca cttcagacaa gcctgcttca gccatcatct cgaagctgga atacgttgca  1080
aaggcgctga atctcagggt aaggaagaag gacaatggtg tggtgaagat gcaagcaggg  1140
aaggagggaa ggaatggtgc tgttcagtta gacatggaga tcttcgagat cacaccttcc  1200
caccacctca ttgagatgaa acaaacaagt ggtgatccgc tggagtaccg ggagctattg  1260
gaggacatcc ggccagcgct gaaggacata gtctgggcct ggcacggaga tgaccaccag  1320
cagcagctag agtag                                                    1335

SEQ ID NO: 3             moltype = DNA   length = 1335
FEATURE                  Location/Qualifiers
source                   1..1335
```

```
                          mol_type = other DNA
                          note = TaCIPK14-4D
                          organism = Triticum aestivum
CDS                       1..1335
                          protein_id = 6
                          translation = MANRGKILMERYELGRLLGKGTFGKVHYARSLESNRSVAIKMLDKE
                            KVLKVGLSEQIRREVTTMRLVAHKNIVQLHEVMATRNKIYFVMEYVKGGELFDKVAKSG
                            KLTEGAAHKYFQQLISAVDYCHSQGVYHRDLKLENLLLDENENLKVSDFGLSALSESKR
                            QDGLLHTTCGTPAYVAPEVISKTGYDGAKSDIWSCGVILFVLVAGYLPFHGSNLMDMYR
                            KIEQGDFRCPGWFSHKLQKLLLKILDPNPSTRASIQKIKESTWFRKGPRGTLAVKERTP
                            SENVITNAPPTAGVRPRKNTHEDVKPLMVTNLNAFEIISFSTGFDLSGLFIQEDCRKET
                            RFTSDKPASTIISKLEYVAKALNLRVRKKDNGVVKMQARKEGRNGAVQLDMEIFEITPS
                            HHLIEMKQTSGDPLEYRELLEDIRPALKDIVWAWHGDDHQQQLE
SEQUENCE: 3
atggcaaaca gagggaagat tctaatggag cggtacgagc tgggaagatt gttggggaaa    60
ggaacattcg gcaaggtgca ctatgcaagg agcctagagt cgaaccgaag cgtcgccata   120
aagatgctgg acaaggagaa ggtgctcaag gtttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaag gcggtgagct ctttgacaag   300
gttgcaaaga gtggcaagct cacagagggt gctgcacata agtatttcca gcagctcatc   360
agtgcagtgg attactgcca cagccaaggc gtgtatcacc gggatctcaa gctggagaac   420
ctgctcctgg atgagaatga gaaccttaag gtctcggatt ttggattgag cgcccttca    480
gagtcaaaga ggcaagatgg cttgctccac accacctgcg gaacaccgc atatgtagct    540
ccggaggtca tcagcaagac aggttacgat ggtgcaaat cagatatctg gtcttgtggt    600
gttatccttt ttgttcttgt tgctggttat ctcccttccc atggttccaa cttgatggac    660
atgtaccgga agattgagca aggagatttc aggtgccccg gctggttctc acacaaactc    720
cagaagctct tgctcaagat cctggacccc aatccaagca ccagggcatc tatccagaag    780
ataaaagagt ctacctggtt ccggaaaggt ccaggggca cccttgcagt gaaggagaga    840
actcccagtg agaatgtcat cacaaatgct cctcctacag ctggtgtgag gccaaggaag    900
aacactcatg aagatgtgaa gcccctaatg gtgacaaact aaatgcctt tgagatcatc    960
tccttctcca cggggtttga cctgtccggc ctattcatcc aagaggactg cagaaaggag   1020
acaaggttca cttcagacaa gcctgcttca accatcatct cgaagctgga atatgttgcg   1080
aaggcgctga atctcagggt aaggaagaag gacaatggcg tggtgaagat gcaagcgagg   1140
aaggagggaa ggaatggtgc tgtacagtta gacatggaga tcttcgagat cacaccttcc   1200
caccacctca ttgagatgaa acaaacaagt ggtgatccgc tggagtaccg ggagctattg   1260
gaggacatcc ggccagcgct gaaggacata gtctgggcct ggcacggaga tgaccaccag   1320
cagcagctag agtag                                                     1335

SEQ ID NO: 4          moltype = AA   length = 444
FEATURE               Location/Qualifiers
source                1..444
                      mol_type = protein
                      note = Protein encoded by TaCIPK14-4A
                      organism = Triticum aestivum
SEQUENCE: 4
MANRGKILME RYELGRLLGK GTFGKVHYAR SLESNRSVAI KMLDKEKVLK VGLSEQIRRE    60
VTTMRLVAHK NIVQLHEVMA TRNKIYFVME YVKGGELFDK VAKSGKLTEG AAHKYFQQLI   120
SAVDYCHSQG VYHRDLKLEN LLLDENENLK VSDFGLSALS ESKRQDGLLH TTCGTPAYVA   180
PEVISKTGYD GAKSDIWSCG VILFVLVAGY LPFHGSNLMD MYRKIEQGDF RCPSWFSHKL   240
QKLLFKILDP NPSTRASIQK IKESTWFRKG PRGTLAVKER TPSENVTTNA PPTAGVRPRK   300
NTHEDVKPLM VTNLNAFEII SFSTGFDLSG LFIREECRKE TRFTSDKPAS AIISKLEYVA   360
KALNLRVRKK DNGVVKMQAR KEGRNGAVQL DMEIFEITPS HHLIEMKQTS GDPLEYRELL   420
EDIRPALKDI VWAWHGDDHH QQLE                                          444

SEQ ID NO: 5          moltype = AA   length = 444
FEATURE               Location/Qualifiers
source                1..444
                      mol_type = protein
                      note = Protein encoded by TaCIPK14-4B
                      organism = Triticum aestivum
SEQUENCE: 5
MANRGKILME RYELGRLLGK GTFGKVHYAR SLESNQSVAI KMLDKEKVLK VGLSEQIRRE    60
VTTMRLVAHK NIVQLHEVMA TRNKIYFVME YVKGGELFDK VAKSGKLTEG AAHKYFQQLI   120
SAVDYCHSQG VYHRDLKLEN LLLDENENLK VSDFGLSALS ESKRQDGLLH TTCGTPAYVA   180
PEVISKTGYD GAKSDIWSCG VILFVLVAGY LPFHGSNLMD MYRKIEQGDF RCPSWFSHKL   240
QKLLCKILDP NPSTRASIQK IKESTWFRKG PRGTLAVKER TPSENVTTNA PPTAGVRPRK   300
NTHEDVQPLT VTNLNAFEII SFSTGFDLSG LFIQEDCRKE TRFTSDKPAS AIISKLEYVA   360
KALNLRVRKK DNGVVKMQAR KEGRNGAVQL DMEIFEITPS HHLIEMKQTS GDPLEYRELL   420
EDIRPALKDI VWAWHGDDHQ QQLE                                          444

SEQ ID NO: 6          moltype = AA   length = 444
FEATURE               Location/Qualifiers
source                1..444
                      mol_type = protein
                      note = Protein encoded by TaCIPK14-4D
                      organism = Triticum aestivum
SEQUENCE: 6
MANRGKILME RYELGRLLGK GTFGKVHYAR SLESNRSVAI KMLDKEKVLK VGLSEQIRRE    60
VTTMRLVAHK NIVQLHEVMA TRNKIYFVME YVKGGELFDK VAKSGKLTEG AAHKYFQQLI   120
```

-continued

```
SAVDYCHSQG VYHRDLKLEN LLLDENENLK VSDFGLSALS ESKRQDGLLH TTCGTPAYVA    180
PEVISKTGYD GAKSDIWSCG VILFVLVAGY LPFHGSNLMD MYRKIEQGDF RCPGWFSHKL    240
QKLLLKILDP NPSTRASIQK IKESTWFRKG PRGTLAVKER TPSENVITNA PPTAGVRPRK    300
NTHEDVKPLM VTNLNAFEII SFSTGFDLSG LFIQEDCRKE TRFTSDKPAS TIISKLEYVA    360
KALNLRVRKK DNGVVKMQAR KEGRNGAVQL DMEIFEITPS HHLIEMKQTS GDPLEYRELL    420
EDIRPALKDI VWAWHGDDHQ QQLE                                          444

SEQ ID NO: 7            moltype = RNA   length = 20
FEATURE                 Location/Qualifiers
source                  1..20
                        mol_type = other RNA
                        note = gRNA1
                        organism = synthetic construct
SEQUENCE: 7
ggcgtgaggt cacaaccatg                                               20

SEQ ID NO: 8            moltype = RNA   length = 20
FEATURE                 Location/Qualifiers
source                  1..20
                        mol_type = other RNA
                        note = gRNA2
                        organism = synthetic construct
SEQUENCE: 8
gtcatggagt atgtgaaagg                                               20

SEQ ID NO: 9            moltype = DNA   length = 24
FEATURE                 Location/Qualifiers
source                  1..24
                        mol_type = other DNA
                        note = Primer VK005-6-R
                        organism = synthetic construct
SEQUENCE: 9
gatgaagtgg acggaaggaa ggag                                          24

SEQ ID NO: 10           moltype = DNA   length = 23
FEATURE                 Location/Qualifiers
source                  1..23
                        mol_type = other DNA
                        note = Primer TaCIPK14-A-F
                        organism = synthetic construct
SEQUENCE: 10
gattgttggg gaaaggaaca ttt                                           23

SEQ ID NO: 11           moltype = DNA   length = 24
FEATURE                 Location/Qualifiers
source                  1..24
                        mol_type = other DNA
                        note = Primer TaCIPK14-A-R
                        organism = synthetic construct
SEQUENCE: 11
ttgtctcctt tctgcactcc tctc                                         24

SEQ ID NO: 12           moltype = DNA   length = 24
FEATURE                 Location/Qualifiers
source                  1..24
                        mol_type = other DNA
                        note = Primer TaCIPK14-B-F
                        organism = synthetic construct
SEQUENCE: 12
cgcagtccat ttgaattata gcca                                          24

SEQ ID NO: 13           moltype = DNA   length = 19
FEATURE                 Location/Qualifiers
source                  1..19
                        mol_type = other DNA
                        note = Primer TaCIPK14-B-R
                        organism = synthetic construct
SEQUENCE: 13
attcagcgcc tttgcaacg                                                19

SEQ ID NO: 14           moltype = DNA   length = 26
FEATURE                 Location/Qualifiers
source                  1..26
                        mol_type = other DNA
                        note = Primer TaCIPK14-D-F
                        organism = synthetic construct
SEQUENCE: 14
aagacatgag agtgttgttc actgtg                                        26
```

-continued

```
SEQ ID NO: 15          moltype = DNA   length = 23
FEATURE                Location/Qualifiers
source                 1..23
                       mol_type = other DNA
                       note = Primer TaCIPK14-D-R
                       organism = synthetic construct
SEQUENCE: 15
agctgtagga ggagcatttg tga                                    23

SEQ ID NO: 16          moltype = DNA   length = 20
FEATURE                Location/Qualifiers
source                 1..20
                       mol_type = other DNA
                       note = Primer g1off1-F
                       organism = synthetic construct
SEQUENCE: 16
cggagttcgg gacctcggtg                                        20

SEQ ID NO: 17          moltype = DNA   length = 22
FEATURE                Location/Qualifiers
source                 1..22
                       mol_type = other DNA
                       note = Primer g1off1-R
                       organism = synthetic construct
SEQUENCE: 17
tcgccttcct cctcctcctg cc                                     22

SEQ ID NO: 18          moltype = DNA   length = 25
FEATURE                Location/Qualifiers
source                 1..25
                       mol_type = other DNA
                       note = Primer g1off2-F
                       organism = synthetic construct
SEQUENCE: 18
acctcctcct ccttcctgtc gtctt                                  25

SEQ ID NO: 19          moltype = DNA   length = 20
FEATURE                Location/Qualifiers
source                 1..20
                       mol_type = other DNA
                       note = Primer g1off2-R
                       organism = synthetic construct
SEQUENCE: 19
tacggggttg ctggcacttg                                        20

SEQ ID NO: 20          moltype = DNA   length = 19
FEATURE                Location/Qualifiers
source                 1..19
                       mol_type = other DNA
                       note = Primer g1off3-F
                       organism = synthetic construct
SEQUENCE: 20
cacggagacg cccagagac                                         19

SEQ ID NO: 21          moltype = DNA   length = 19
FEATURE                Location/Qualifiers
source                 1..19
                       mol_type = other DNA
                       note = Primer g1off3-R
                       organism = synthetic construct
SEQUENCE: 21
cgcacggtag gagcaacgg                                         19

SEQ ID NO: 22          moltype = DNA   length = 25
FEATURE                Location/Qualifiers
source                 1..25
                       mol_type = other DNA
                       note = Primer g1off4-F
                       organism = synthetic construct
SEQUENCE: 22
tatttcctcc atcttgctct cttcc                                  25

SEQ ID NO: 23          moltype = DNA   length = 26
FEATURE                Location/Qualifiers
source                 1..26
                       mol_type = other DNA
                       note = Primer g1off-4-R
                       organism = synthetic construct
SEQUENCE: 23
```

-continued

```
caagtgtcta ctctctccat ccacaa                                          26

SEQ ID NO: 24            moltype = DNA   length = 20
FEATURE                  Location/Qualifiers
source                   1..20
                         mol_type = other DNA
                         note = Primer g1off5-F
                         organism = synthetic construct
SEQUENCE: 24
cgtgtgcctg ctttttgctg                                                 20

SEQ ID NO: 25            moltype = DNA   length = 23
FEATURE                  Location/Qualifiers
source                   1..23
                         mol_type = other DNA
                         note = Primer g1off5-R
                         organism = synthetic construct
SEQUENCE: 25
cgccagtgtt gatgtgagat tgt                                             23

SEQ ID NO: 26            moltype = DNA   length = 19
FEATURE                  Location/Qualifiers
source                   1..19
                         mol_type = other DNA
                         note = Primer g1off6-F
                         organism = synthetic construct
SEQUENCE: 26
ggggaggatg tgggcagat                                                  19

SEQ ID NO: 27            moltype = DNA   length = 22
FEATURE                  Location/Qualifiers
source                   1..22
                         mol_type = other DNA
                         note = Primer g1off6-R
                         organism = synthetic construct
SEQUENCE: 27
cgcaacgagg accaacactt ta                                              22

SEQ ID NO: 28            moltype = DNA   length = 27
FEATURE                  Location/Qualifiers
source                   1..27
                         mol_type = other DNA
                         note = Primer g1off7-F
                         organism = synthetic construct
SEQUENCE: 28
ctcatccatt tttatcacaa ccttaga                                         27

SEQ ID NO: 29            moltype = DNA   length = 19
FEATURE                  Location/Qualifiers
source                   1..19
                         mol_type = other DNA
                         note = Primer g1off7-R
                         organism = synthetic construct
SEQUENCE: 29
gctgaccgcc agacccact                                                  19

SEQ ID NO: 30            moltype = DNA   length = 23
FEATURE                  Location/Qualifiers
source                   1..23
                         mol_type = other DNA
                         note = OFF1
                         organism = Triticum aestivum
SEQUENCE: 30
agctcgaggt cacaaccatg ggg                                             23

SEQ ID NO: 31            moltype = DNA   length = 23
FEATURE                  Location/Qualifiers
source                   1..23
                         mol_type = other DNA
                         note = OFF2
                         organism = Triticum aestivum
SEQUENCE: 31
agctagaggt cacaaccatg ggg                                             23

SEQ ID NO: 32            moltype = DNA   length = 23
FEATURE                  Location/Qualifiers
source                   1..23
                         mol_type = other DNA
                         note = OFF3
```

```
                            organism = Triticum aestivum
SEQUENCE: 32
agctcgaggt cacaaccatg ggg                                        23

SEQ ID NO: 33            moltype = DNA   length = 23
FEATURE                  Location/Qualifiers
source                   1..23
                         mol_type = other DNA
                         note = OFF4
                         organism = Triticum aestivum
SEQUENCE: 33
cgagtgaggt cgcaaccatg cgg                                        23

SEQ ID NO: 34            moltype = DNA   length = 23
FEATURE                  Location/Qualifiers
source                   1..23
                         mol_type = other DNA
                         note = OFF5
                         organism = Triticum aestivum
SEQUENCE: 34
ggttctgtcc ttctctgcaa tgg                                        23

SEQ ID NO: 35            moltype = DNA   length = 23
FEATURE                  Location/Qualifiers
source                   1..23
                         mol_type = other DNA
                         note = OFF6
                         organism = Triticum aestivum
SEQUENCE: 35
aattttctcc ttcgctgcaa agg                                        23

SEQ ID NO: 36            moltype = DNA   length = 23
FEATURE                  Location/Qualifiers
source                   1..23
                         mol_type = other DNA
                         note = OFF7
                         organism = Triticum aestivum
SEQUENCE: 36
tgctctctac ttcactgcaa tgg                                        23

SEQ ID NO: 37            moltype = DNA   length = 29
FEATURE                  Location/Qualifiers
source                   1..29
                         mol_type = other DNA
                         note = Fragment of TaCIPK14-4A of Fielder
                         organism = Triticum aestivum
SEQUENCE: 37
gtcatggagt atgtgaaagg cggtgagct                                  29

SEQ ID NO: 38            moltype = DNA   length = 30
FEATURE                  Location/Qualifiers
source                   1..30
                         mol_type = other DNA
                         note = Fragment of TaCIPK14-4A of T0-4
                         organism = Triticum aestivum
SEQUENCE: 38
gtcatggagt atgtgaaaag gcggtgagct                                 30

SEQ ID NO: 39            moltype = DNA   length = 29
FEATURE                  Location/Qualifiers
source                   1..29
                         mol_type = other DNA
                         note = Fragment of TaCIPK14-4A of T0-12
                         organism = Triticum aestivum
SEQUENCE: 39
gtcatggagt atgtgaaagg cggtgagct                                  29

SEQ ID NO: 40            moltype = DNA   length = 29
FEATURE                  Location/Qualifiers
source                   1..29
                         mol_type = other DNA
                         note = Fragment of TaCIPK14-4B of Fielder
                         organism = Triticum aestivum
SEQUENCE: 40
gtcatggagt atgtgaaagg cggtgagct                                  29

SEQ ID NO: 41            moltype = DNA   length = 30
FEATURE                  Location/Qualifiers
source                   1..30
```

-continued

```
                          mol_type = other DNA
                          note = Fragment of TaCIPK14-4B of T0-4
                          organism = Triticum aestivum
SEQUENCE: 41
gtcatggagt atgtgaaaag gcggtgagct                                        30

SEQ ID NO: 42            moltype = DNA   length = 29
FEATURE                  Location/Qualifiers
source                   1..29
                          mol_type = other DNA
                          note = Fragment of TaCIPK14-4B of T0-12
                          organism = Triticum aestivum
SEQUENCE: 42
gtcatggagt atgggagagg agctcattt                                         29

SEQ ID NO: 43            moltype = DNA   length = 29
FEATURE                  Location/Qualifiers
source                   1..29
                          mol_type = other DNA
                          note = Fragment of TaCIPK14-4D of Fielder
                          organism = Triticum aestivum
SEQUENCE: 43
gtcatggagt atgtgaaagg cggtgagct                                         29

SEQ ID NO: 44            moltype = DNA   length = 29
FEATURE                  Location/Qualifiers
source                   1..29
                          mol_type = other DNA
                          note = Fragment of TaCIPK14-4D of T0-4
                          organism = Triticum aestivum
SEQUENCE: 44
gtcatggagt atgtgaaagg cggtgagct                                         29

SEQ ID NO: 45            moltype = DNA   length = 29
FEATURE                  Location/Qualifiers
source                   1..29
                          mol_type = other DNA
                          note = Fragment of TaCIPK14-4D of T0-12
                          organism = Triticum aestivum
SEQUENCE: 45
gtcatggagt atgtgagggg agctctttg                                         29

SEQ ID NO: 46            moltype = DNA   length = 29
FEATURE                  Location/Qualifiers
source                   1..29
                          mol_type = other DNA
                          note = Fragment of TaCIPK14-4A of Fielder
                          organism = Triticum aestivum
SEQUENCE: 46
ggcgtgaggt cacaaccatg cggttggtg                                         29

SEQ ID NO: 47            moltype = DNA   length = 29
FEATURE                  Location/Qualifiers
source                   1..29
                          mol_type = other DNA
                          note = Fragment of TaCIPK14-4A of T0-21
                          organism = Triticum aestivum
SEQUENCE: 47
ggcgtgaggt cacaaccatg cggttggtg                                         29

SEQ ID NO: 48            moltype = DNA   length = 29
FEATURE                  Location/Qualifiers
source                   1..29
                          mol_type = other DNA
                          note = Fragment of TaCIPK14-4B of Fielder
                          organism = Triticum aestivum
SEQUENCE: 48
ggcgtgaggt cacaaccatg cggttggtg                                         29

SEQ ID NO: 49            moltype = DNA   length = 29
FEATURE                  Location/Qualifiers
source                   1..29
                          mol_type = other DNA
                          note = Fragment of TaCIPK14-4B of T0-21
                          organism = Triticum aestivum
SEQUENCE: 49
ggcgtgaggt cacaaccatg cggtgggct                                         29

SEQ ID NO: 50            moltype = DNA   length = 29
```

```
FEATURE                  Location/Qualifiers
source                   1..29
                         mol_type = other DNA
                         note = Fragment of TaCIPK14-4D of Fielder
                         organism = Triticum aestivum
SEQUENCE: 50
ggcgtgaggt cacaaccatg cggttggtg                                        29

SEQ ID NO: 51            moltype = DNA  length = 29
FEATURE                  Location/Qualifiers
source                   1..29
                         mol_type = other DNA
                         note = Fragment of TaCIPK14-4D of T0-21
                         organism = Triticum aestivum
SEQUENCE: 51
ggcgtgaggt cgttggtggc acacaagaa                                        29

SEQ ID NO: 52            moltype = DNA  length = 33
FEATURE                  Location/Qualifiers
source                   1..33
                         mol_type = other DNA
                         note = Fragment of TaCIPK14-4A of Fielder
                         organism = Triticum aestivum
SEQUENCE: 52
caggcgtgag gtcacaacca tgcggttggt ggc                                   33

SEQ ID NO: 53            moltype = DNA  length = 34
FEATURE                  Location/Qualifiers
source                   1..34
                         mol_type = other DNA
                         note = Fragment of TaCIPK14-4A of Fielder
                         organism = Triticum aestivum
SEQUENCE: 53
tatactttgt catggagtat gtgaaaggcg gtga                                  34

SEQ ID NO: 54            moltype = DNA  length = 33
FEATURE                  Location/Qualifiers
source                   1..33
                         mol_type = other DNA
                         note = Fragment of TaCIPK14-4B of Fielder
                         organism = Triticum aestivum
SEQUENCE: 54
caggcgtgag gtcacaacca tgcggctggt ggc                                   33

SEQ ID NO: 55            moltype = DNA  length = 34
FEATURE                  Location/Qualifiers
source                   1..34
                         mol_type = other DNA
                         note = Fragment of TaCIPK14-4B of Fielder
                         organism = Triticum aestivum
SEQUENCE: 55
tatactttgt catggagtat gtgaaaggcg gtga                                  34

SEQ ID NO: 56            moltype = DNA  length = 33
FEATURE                  Location/Qualifiers
source                   1..33
                         mol_type = other DNA
                         note = Fragment of TaCIPK14-4D of Fielder
                         organism = Triticum aestivum
SEQUENCE: 56
caggcgtgag gtcacaacca tgcggttggt ggc                                   33

SEQ ID NO: 57            moltype = DNA  length = 33
FEATURE                  Location/Qualifiers
source                   1..33
                         mol_type = other DNA
                         note = Fragment of TaCIPK14-4D of Fielder
                         organism = Triticum aestivum
SEQUENCE: 57
tatactttgt catggagtat ggaaaggcgg tga                                   33

SEQ ID NO: 58            moltype = DNA  length = 33
FEATURE                  Location/Qualifiers
source                   1..33
                         mol_type = other DNA
                         note = Fragment of TaCIPK14-4A of KO-1
                         organism = Triticum aestivum
SEQUENCE: 58
caggcgtgag gtcacaacca tgcggttggt ggc                                   33
```

```
SEQ ID NO: 59            moltype = DNA  length = 35
FEATURE                  Location/Qualifiers
source                   1..35
                         mol_type = other DNA
                         note = Fragment of TaCIPK14-4A of KO-1
                         organism = Triticum aestivum
SEQUENCE: 59
tatactttgt catggagtat gtgaaaaggc ggtga                                35

SEQ ID NO: 60            moltype = DNA  length = 32
FEATURE                  Location/Qualifiers
source                   1..32
                         mol_type = other DNA
                         note = Fragment of TaCIPK14-4B of KO-1
                         organism = Triticum aestivum
SEQUENCE: 60
caggcgtgag gtcacaacca tgcggctggt gg                                   32

SEQ ID NO: 61            moltype = DNA  length = 29
FEATURE                  Location/Qualifiers
source                   1..29
                         mol_type = other DNA
                         note = Fragment of TaCIPK14-4B of KO-1
                         organism = Triticum aestivum
SEQUENCE: 61
tatactttgt catggagtaa aggcggtga                                       29

SEQ ID NO: 62            moltype = DNA  length = 33
FEATURE                  Location/Qualifiers
source                   1..33
                         mol_type = other DNA
                         note = Fragment of TaCIPK14-4D of KO-1
                         organism = Triticum aestivum
SEQUENCE: 62
caggcgtgag gtcacaacca tgcggttggt ggc                                  33

SEQ ID NO: 63            moltype = DNA  length = 29
FEATURE                  Location/Qualifiers
source                   1..29
                         mol_type = other DNA
                         note = Fragment of TaCIPK14-4D of KO-1
                         organism = Triticum aestivum
SEQUENCE: 63
tatactttgt catggagtat aggcggtga                                       29

SEQ ID NO: 64            moltype = DNA  length = 33
FEATURE                  Location/Qualifiers
source                   1..33
                         mol_type = other DNA
                         note = Fragment of TaCIPK14-4A of KO-2
                         organism = Triticum aestivum
SEQUENCE: 64
caggcgtgag gtcacaacca tgcggttggt ggc                                  33

SEQ ID NO: 65            moltype = DNA  length = 35
FEATURE                  Location/Qualifiers
source                   1..35
                         mol_type = other DNA
                         note = Fragment of TaCIPK14-4A of KO-2
                         organism = Triticum aestivum
SEQUENCE: 65
tatactttgt catggagtat gtgaaaaggc ggtga                                35

SEQ ID NO: 66            moltype = DNA  length = 33
FEATURE                  Location/Qualifiers
source                   1..33
                         mol_type = other DNA
                         note = Fragment of TaCIPK14-4B of KO-2
                         organism = Triticum aestivum
SEQUENCE: 66
caggcgtgag gtcacaacca tgcggctggt ggc                                  33

SEQ ID NO: 67            moltype = DNA  length = 35
FEATURE                  Location/Qualifiers
source                   1..35
                         mol_type = other DNA
                         note = Fragment of TaCIPK14-4B of KO-2
                         organism = Triticum aestivum
```

-continued

```
SEQUENCE: 67
tatactttgt catggagtat gtgaaaaggc ggtga                              35

SEQ ID NO: 68            moltype = DNA   length = 33
FEATURE                  Location/Qualifiers
source                   1..33
                         mol_type = other DNA
                         note = Fragment of TaCIPK14-4D of KO-2
                         organism = Triticum aestivum
SEQUENCE: 68
caggcgtgag gtcacaacca tgcggttggt ggc                                33

SEQ ID NO: 69            moltype = DNA   length = 28
FEATURE                  Location/Qualifiers
source                   1..28
                         mol_type = other DNA
                         note = Fragment of TaCIPK14-4D of KO-2
                         organism = Triticum aestivum
SEQUENCE: 69
tatacttgtc atggagtata ggcggtga                                      28

SEQ ID NO: 70            moltype = DNA   length = 33
FEATURE                  Location/Qualifiers
source                   1..33
                         mol_type = other DNA
                         note = Fragment of TaCIPK14-4A of KO-3
                         organism = Triticum aestivum
SEQUENCE: 70
caggcgtgag gtcacaacca tgcggttggt ggc                                33

SEQ ID NO: 71            moltype = DNA   length = 35
FEATURE                  Location/Qualifiers
source                   1..35
                         mol_type = other DNA
                         note = Fragment of TaCIPK14-4A of KO-3
                         organism = Triticum aestivum
SEQUENCE: 71
tatactttgt catggagtat gtgaaaaggc ggtga                              35

SEQ ID NO: 72            moltype = DNA   length = 33
FEATURE                  Location/Qualifiers
source                   1..33
                         mol_type = other DNA
                         note = Fragment of TaCIPK14-4B of KO-3
                         organism = Triticum aestivum
SEQUENCE: 72
caggcgtgag gtcacaacca tgcggctggt ggc                                33

SEQ ID NO: 73            moltype = DNA   length = 29
FEATURE                  Location/Qualifiers
source                   1..29
                         mol_type = other DNA
                         note = Fragment of TaCIPK14-4B of KO-3
                         organism = Triticum aestivum
SEQUENCE: 73
tatactttgt catggagtaa aggcggtga                                     29

SEQ ID NO: 74            moltype = DNA   length = 33
FEATURE                  Location/Qualifiers
source                   1..33
                         mol_type = other DNA
                         note = Fragment of TaCIPK14-4D of KO-3
                         organism = Triticum aestivum
SEQUENCE: 74
caggcgtgag gtcacaacca tgcggttggt ggc                                33

SEQ ID NO: 75            moltype = DNA   length = 33
FEATURE                  Location/Qualifiers
source                   1..33
                         mol_type = other DNA
                         note = Fragment of TaCIPK14-4D of KO-3
                         organism = Triticum aestivum
SEQUENCE: 75
tatactttgt catggagtat gtgaaggcgg tga                                33

SEQ ID NO: 76            moltype = DNA   length = 33
FEATURE                  Location/Qualifiers
source                   1..33
                         mol_type = other DNA
```

-continued

```
                          note = Fragment of TaCIPK14-4A of KO-4
                          organism = Triticum aestivum
SEQUENCE: 76
caggcgtgag gtcacaacca tgcggttggt ggc                              33

SEQ ID NO: 77         moltype = DNA   length = 35
FEATURE               Location/Qualifiers
source                1..35
                      mol_type = other DNA
                      note = Fragment of TaCIPK14-4A of KO-4
                      organism = Triticum aestivum
SEQUENCE: 77
tatactttgt catggagtat gtgaaaaggc ggtga                           35

SEQ ID NO: 78         moltype = DNA   length = 19
FEATURE               Location/Qualifiers
source                1..19
                      mol_type = other DNA
                      note = Fragment of TaCIPK14-4B of KO-4
                      organism = Triticum aestivum
SEQUENCE: 78
caggcgtgag gtcacaacc                                             19

SEQ ID NO: 79         moltype = DNA   length = 22
FEATURE               Location/Qualifiers
source                1..22
                      mol_type = other DNA
                      note = Fragment of TaCIPK14-4D of KO-4
                      organism = Triticum aestivum
SEQUENCE: 79
caggcgtgag gtcgttggtg gc                                         22

SEQ ID NO: 80         moltype = DNA   length = 34
FEATURE               Location/Qualifiers
source                1..34
                      mol_type = other DNA
                      note = Fragment of TaCIPK14-4D of KO-4
                      organism = Triticum aestivum
SEQUENCE: 80
tatactttgt catggagtat gtgaaaggcg gtga                            34

SEQ ID NO: 81         moltype = DNA   length = 33
FEATURE               Location/Qualifiers
source                1..33
                      mol_type = other DNA
                      note = Fragment of TaCIPK14-4A of KO-5
                      organism = Triticum aestivum
SEQUENCE: 81
caggcgtgag gtcacaacca tgcggttggt ggc                             33

SEQ ID NO: 82         moltype = DNA   length = 35
FEATURE               Location/Qualifiers
source                1..35
                      mol_type = other DNA
                      note = Fragment of TaCIPK14-4A of KO-5
                      organism = Triticum aestivum
SEQUENCE: 82
tatactttgt catggagtat gtgaaaaggc ggtga                           35

SEQ ID NO: 83         moltype = DNA   length = 33
FEATURE               Location/Qualifiers
source                1..33
                      mol_type = other DNA
                      note = Fragment of TaCIPK14-4B of KO-5
                      organism = Triticum aestivum
SEQUENCE: 83
caggcgtgag gtcacaacca tgcggctggt ggc                             33

SEQ ID NO: 84         moltype = DNA   length = 35
FEATURE               Location/Qualifiers
source                1..35
                      mol_type = other DNA
                      note = Fragment of TaCIPK14-4B of KO-5
                      organism = Triticum aestivum
SEQUENCE: 84
tatactttgt catggagtat gtgaaaaggc ggtga                           35

SEQ ID NO: 85         moltype = DNA   length = 21
FEATURE               Location/Qualifiers
```

```
source              1..21
                    mol_type = other DNA
                    note = Fragment of TaCIPK14-4D of KO-5
                    organism = Triticum aestivum
SEQUENCE: 85
caggcgtgag gtcgttgggg c                                        21

SEQ ID NO: 86           moltype = DNA  length = 34
FEATURE                 Location/Qualifiers
source                  1..34
                        mol_type = other DNA
                        note = Fragment of TaCIPK14-4D of KO-5
                        organism = Triticum aestivum
SEQUENCE: 86
tatactttgt catggagtat gtgaaaggcg gtga                          34

SEQ ID NO: 87           moltype = DNA  length = 1336
FEATURE                 Location/Qualifiers
source                  1..1336
                        mol_type = other DNA
                        note = TaCIPK14-4A of KO-1
                        organism = Triticum aestivum
SEQUENCE: 87
atggcaaaca gagggaagat tctaatggag cggtacgagc tgggaagatt gttggggaaa   60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaaa ggcggtgagc tctttgacaa   300
ggttgcaaag agtggcaagc tcacagaggg tgctgcacat aagtatttcc agcagctcat   360
cagtgcagtg gattactgcc acagccaagg cgtgtatcac cgggatctca agctggagaa   420
cctgctcctg gatgagaatg agaaccttaa ggtctcggat tttggattga gcgcactttc   480
agagtcaaag aggcaagatg gcttgctgca caccacctgc ggaacacccg catatgtagc   540
tccggaggtc atcagcaaga caggttatga tggtgcgaaa tcagatatct ggtcttgtgg   600
tgttatcctt tttgttcttg ttgctggtta tctccctttc catgttcca acttgatgga   660
catgtaccgg aagattgagc aaggagattt caggtgcccc agctggttct cacacaaact   720
ccagaagctc ttgttcaaga ttctggaccc caatccaagc accagggcat ctatccagaa   780
gataaaagag tctacctggt tccggaaagg tccaagggga acccttgcag tgaaggagag   840
aactcccagt gagaacgtca ccacaaatgc tcctcctaca gctggtgtga ggccaaggaa   900
gaacactcat gaagatgtga agccctgat ggtgacaaac ttaaatgcct ttgagatcat   960
ctccttctcc acgggggtttg acctgtctgg cctattcatc cgagaggagt gcagaaagga   1020
gacaaggttc acttcagaca agcctgcttc agccatcatc tcgaagctgg aatatgttgc   1080
gaaagcgctg aatctcaggg taaggaagaa ggacaatggc gtggtgaaga tgcaagcgag   1140
gaaggaagga aggaatggtg ctgttcagtt agacatggag atcttcggaa tcacaccttc   1200
ccaccacctc attgagatga aacaaacaag tggtgatcca ctggagtacc gggagctatt   1260
ggaggacatc cggccagcgc tgaaggacat agtctgggcc tggcacggag atgaccacca   1320
ccagcagcta gagtag                                              1336

SEQ ID NO: 88           moltype = DNA  length = 1330
FEATURE                 Location/Qualifiers
source                  1..1330
                        mol_type = other DNA
                        note = TaCIPK14-4B of KO-1
                        organism = Triticum aestivum
SEQUENCE: 88
atggcaaaca gagggaagat tctaatggag cggtacgagc tgggaagatt gttggggaaa   60
ggaacattcg gcaaggtgca ctatgcaagg agcctagagt cgaaccaaag cgtcgccata   120
aagatgctgg acaaggagaa ggtgctcaag gttgggctct cggagcaaat caggcgtgag   180
gtcacaacca tgcggctggt ggcacacaag aacattgttc agcttcatga ggtcatggcg   240
acacgaaaca aaatatactt tgtcatggag taaaggcggt gagctctttg acaaggttgc   300
aaagagtggc aagctcacag agggtgctgc acataagtat ttccagcagc tcatcagtgc   360
agtggattac tgccacagcc aaggcgtgta tcaccgggat ctcaagctgg agaacctgct   420
cctgatgag aatgagaacc ttaaggtctc agatttggga ctgagcgcac tttcagagtc   480
aaagaggcaa gatggcttgc tccacaccac ctgcggaaca cctgcatatg tagctccgga   540
ggtcatcagc aagacaggtt acgatggtgc gaaatcagat atctggtctt gtggtcatgta   600
ccttttttgtt cttgttgctg ttatctccc tttccatgtt tccaacttga tggacatgta   660
ccggaagatt gaacaaggag atttcaggtg ccccagctgg ttctcacaca aactccagaa   720
gctcttgtgc aagatcctgg accccaatcc aagcaccagg gcatctatcc agaagataaa   780
agagtctacc tggtttcgga aaggtccaag gggcacccct gcagtgaagg agagaactcc   840
cagtgagaat gtcaccacaa atgctcctcc tacagctggt gtgaggccaa ggaagaacac   900
tcatgaagat gtgcagcccc tgacggtgac aaacttaaat gcctttgaga tcatctcctt   960
ctccacgggg tttgacctgt ccggcctatt catccaagag gactgcagaa aggagacaag   1020
gttcacttca gacaagcctg cttcagccat catctcgaag ctggaatacg ttgcaaaggc   1080
gctgaatctc agggtaagga agaaggacaa tggtgtggtg aagatgcaag caaggaagga   1140
gggaaggaat ggtgctgttc agttagacat ggagatcacc cttcccacca cttcccacca   1200
cctcattgag atgaaacaaa caagtggtga tccgctggag taccgggagc tattggagga   1260
catccggcca cgcgctgaag gacatagtct ggcctggcac ggagatgacc accagcagca   1320
gctagagtag                                                    1330

SEQ ID NO: 89           moltype = DNA  length = 1330
```

-continued

```
FEATURE           Location/Qualifiers
source            1..1330
                  mol_type = other DNA
                  note = TaCIPK14-4D of KO-1
                  organism = Triticum aestivum
SEQUENCE: 89
atggcaaaca gagggaagat tctaatggag cggtacgagc tgggaagatt gttggggaaa    60
ggaacattcg gcaaggtgca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tataggcggt gagctctttg acaaggttgc   300
aaagagtggc aagctcacag agggtgctgc acataagtat ttccagcagc tcatcagtgc   360
agtggattac tgccacagcc aaggcgtgta tcaccgggat ctcaagctgg agaacctgct   420
cctggatgag aatgagaacc ttaaggtctc ggattttgga ttgagcgccc tttcagagtc   480
aaagaggcaa gatggcttgc tccacaccac ctgcggaaca cccgcatatg tagctccgga   540
ggtcatcagc aagacaggtt acgatggtgc aaaatcagat atctggtctt gtggtgttat   600
cctttttgtt cttgttgctg gttatctccc tttccatggt tccaacttga tggacatgta   660
ccggaagatt gagcaaggag atttcaggtg ccccggctgg ttctcacaca aactccagaa   720
gctcttgctc aagatcctgg accccaatcc aagcaccagg gcatctatcc agaagataaa   780
agagtctacc tggttccgga aaggtccaag gggcacccct gcagtgaagg agagaactcc   840
cagtgagaat gtcatcacaa atgctcctcc tacagctggt gtgaggccaa ggaagaacac   900
tcatgaagat gtgaagcccc taatggtgac aaacttaaat gcctttgaga tcatctcctt   960
ctccacgggg tttgacctgt ccggcctatt catccaagag gactgcagaa aggagacaag  1020
gttcacttca gacaagcctg cttcaaccat catctcgaag ctggaatatg ttgcgaaggc  1080
gctgaatctc agggtaagga agaaggacaa tggcgtggtg aagatgcaag cgaggaagga  1140
gggaaggaat ggtgctgtac agttagacat ggagatcttc gagatcacac cttcccacca  1200
cctcattgag atgaaacaaa caagtggtga tccgctggag taccgggagc tattggagga  1260
catccggcca gcgctgaagg acatagtctg ggcctggcac ggagatgacc accagcagca  1320
gctagagtag                                                        1330

SEQ ID NO: 90         moltype = DNA   length = 1336
FEATURE               Location/Qualifiers
source                1..1336
                      mol_type = other DNA
                      note = TaCIPK14-4A of KO-2
                      organism = Triticum aestivum
SEQUENCE: 90
atggcaaaca gagggaagat tctaatggag cggtacgagc tgggaagatt gttggggaaa    60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaaa ggcggtgagc tctttgacaa   300
ggttgcaaag agtggcaagc tcacagaggg tgctgcacat aagtatttcc agcagctcat   360
cagtgcagtg gattactgcc acagccaagg cgtgtatcac cgggatctca agctggagaa   420
cctgctcctg gatgagaatg agaaccttaa ggtctcggat tttggattga gcgcactttc   480
agagtcaaag aggcaagatg gcttgctgca caccacctgc ggaacacccg catatgtagc   540
tccggaggtc atcagcaaga caggttatga tggtgcaaaa tcagatatct ggtcttgtgg   600
tgttatcctt tttgttcttg ttgctggtta tctccctttc catggttcca acttgatgga   660
catgtaccgg aagattgagc aaggagattt caggtgcccc agctggttct cacacaaact   720
ccagaagctc ttgttcaaga ttctggaccc caatccaagc accagggcat ctatccagaa   780
gataaaagag tctacctggt tccggaaagg tccaagggga cccttgcag tgaaggagga   840
aactcccagt gagaacgtca ccacaaatgc tcctcctaca gctggtgtga ggccaaggaa   900
gaacactcat gaagatgtga gccctgat ggtgacaaac ttaaatgcct ttgagatcat   960
ctccttctcc acggggtttg acctgtctgg cctattcatc cgagaggagt gcagaaagga  1020
gacaaggttc acttcagaca gcctgcttc agccatcatc tcgaagctgcg aatatgttgc  1080
gaaagcgctg aatctcaggg taaggaagaa ggacaatggc gtggtgaaga tgcaagcgag  1140
gaaggaagga aggaatggtg ctgttcagtt agacatggag atcttcgaga tcacaccttc  1200
ccaccacctc attgagatga aacaaacaag tggtgatcca ctggagtacc gggagctatt  1260
ggaggacatc cggccagcgc tgaaggacat agtctgggcc tggcacggag atgaccacca  1320
ccagcagcta gagtag                                                  1336

SEQ ID NO: 91         moltype = DNA   length = 1336
FEATURE               Location/Qualifiers
source                1..1336
                      mol_type = other DNA
                      note = TaCIPK14-4B of KO-2
                      organism = Triticum aestivum
SEQUENCE: 91
atggcaaaca gagggaagat tctaatggag cggtacgagc tgggaagatt gttggggaaa    60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaaa ggcggtgagc tctttgacaa   300
ggttgcaaag agtggcaagc tcacagaggg tgctgcacat aagtatttcc agcagctcat   360
cagtgcagtg gattactgcc acagccaagg cgtgtatcac cgggatctca agctggagaa   420
cctgctcctg gatgagaatg agaaccttaa ggtctcggat tttggattga gcgcactttc   480
agagtcaaag aggcaagatg gcttgctgca caccacctgc ggaacacccg catatgtagc   540
tccggaggtc atcagcaaga caggttatga tggtgcaaaa tcagatatct ggtcttgtgg   600
tgttatcctt tttgttcttg ttgctggtta tctccctttc catggttcca acttgatgga   660
```

-continued

```
catgtaccgg aagattgagc aaggagattt caggtgcccc agctggttct cacacaaact   720
ccagaagctc ttgttcaaga ttctggaccc caatccaagc accagggcat ctatccagaa   780
gataaaagag tctacctggt tccggaaagg tccaagggga acccttgcag tgaaggagag   840
aactcccagt gagaacgtca ccacaaatgc tcctcctaca gctggtgtga ggccaaggaa   900
gaacactcat gaagatgtga agcccctgat ggtgacaaac ttaaatgcct ttgagatcat   960
ctccttctcc acggggtttg acctgtctgg cctattcatc cgagaggagt gcagaaagga  1020
gacaaggttc acttcagaca agcctgcttc agccatcatc tcgaagctgg aatatgttgc  1080
gaaagcgctg aatctcaggg taaggaagaa ggacaatggc gtggtgaaga tgcaagcgag  1140
gaaggaagga aggaatggtg ctgttcagtt agacatggag atcttcgaga tcacaccttc  1200
ccaccacctc attgagatga aacaaacaag tggtgatcca ctggagtacc gggagctatt  1260
ggaggacatc cggccagcgc tgaaggacat agtctgggcc tggcacggag atgaccacca  1320
ccagcagcta gagtag                                                  1336
```

SEQ ID NO: 92          moltype = DNA  length = 1330
FEATURE                Location/Qualifiers
source                 1..1330
                       mol_type = other DNA
                       note = TaCIPK14-4D of KO-2
                       organism = Triticum aestivum SEQUENCE: 92
```
atggcaaaca gagggaagat tctaatggag cggtacgagc tgggaagatt gttggggaaa    60
ggaacattcg gcaaggtgca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tataggcggt gagctctttg acaaggttgc   300
aaagagtggc aagctcacag agggtgctgc acataagtat ttccagcagc tcatcagtgc   360
agtggattac tgccacagcc aaggcgtgta tcaccgggat ctcaagctgg agaacctgct   420
cctggatgag aatgagaacc ttaaggtctc ggattttgga ttgagcgccc tttcagagtc   480
aaagaggcaa gatggcttgc tccacaccac ctgcggaaca cccgcatatg tagctccgga   540
ggtcatcagc aagacaggtt acgatggtgc aaaatcagat atctggtctt gtggtgttat   600
ccttttttgtt cttgttgctg gttatctccc tttccatggt tccaacttga tggacatgta   660
ccggaagatt gagcaaggag atttcaggtg ccccggctgg ttctcacaca aactccagaa   720
gctcttgctc aagatcctgg accccaatcc aagcaccagg gcatctatcc agaagataaa   780
agagtctacc tggttccgga aaggtccaag gggcaccctt gcagtgaagg agagaaactcc   840
cagtgagaat gtcatcacaa atgctcctcc tacagctggt gtgaggccaa ggaagaacac   900
tcatgaagat gtgaagcccc taatggtgac aaacttaaat gcctttgaga tcatctcctt   960
ctccacgggg tttgacctgt ccggcctatt catccaagag gactgcagaa aggagacaag  1020
gttcacttca gacaagcctg cttcaaccat catctcgaag ctggaatatg ttgcgaaggc  1080
gctgaatctc agggtaagga agaaggacaa tggcgtggtg gaagatgcaag cgaggaagaac  1140
gggaaggaat ggtgctgtac agttagacat ggagatcttc gagatcacac cttcccacca  1200
cctcattgag atgaaacaaa caagtggtga tccgctggag taccgggagc tattggagga  1260
catccggcca gcgctgaagg acatagtctg ggcctggcac ggagatgacc accagcagca  1320
gctagagtag                                                        1330
```

SEQ ID NO: 93          moltype = DNA  length = 1336
FEATURE                Location/Qualifiers
source                 1..1336
                       mol_type = other DNA
                       note = TaCIPK14-4A of KO-3
                       organism = Triticum aestivum SEQUENCE: 93
```
atggcaaaca gagggaagat tctaatggag cggtacgagc tgggaagatt gttggggaaa    60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaaa ggcggtgagc tctttgacaa   300
ggttgcaaag agtggcaagc tcacagaggg tgctgcacat aagtatttcc agcagctcat   360
cagtgcagtg gattactgcc acagccaggc gtgtatcac cgggatctca gctggagaa   420
cctgctcctg gatgagaatg agaaccttaa ggtctcggat tttggattga gcgcactttc   480
agagtcaaag aggcaagatg gcttgctgca caccactgc ggaacacccg catatgtagc   540
tccgaggtc atcagcaaga caggttatga tggtgcgaaa tcagatatct ggtcttgtgg   600
tgttatcctt tttgttcttg ttgctggtta tctcccttc catggttcca acttgatgga   660
catgtaccgg aagattgagc aaggagattt caggtgcccc agctggttct cacacaaact   720
ccagaagctc ttgttcaaga ttctggaccc caatccaagc accagggcat ctatccagaa   780
gataaaagag tctacctggt tccggaaagg tccaagggga acccttgcag tgaaggagag   840
aactcccagt gagaacgtca ccacaaatgc tcctcctaca gctggtgtga ggccaaggaa   900
gaacactcat gaagatgtga agcccctgat ggtgacaaac ttaaatgcct ttgagatcat   960
ctccttctcc acggggtttg acctgtctgg cctattcatc cgagaggagt gcagaaagga  1020
gacaaggttc acttcagaca agcctgcttc agccatcatc tcgaagctgg aatatgttgc  1080
gaaagcgctg aatctcaggg taaggaagaa ggacaatggc gtggtgaaga tgcaagcgag  1140
gaaggaagga aggaatggtg ctgttcagtt agacatggag atcttcgaga tcacaccttc  1200
ccaccacctc attgagatga aacaaacaag tggtgatcca ctggagtacc gggagctatt  1260
ggaggacatc cggccagcgc tgaaggacat agtctgggcc tggcacggag atgaccacca  1320
ccagcagcta gagtag                                                  1336
```

SEQ ID NO: 94          moltype = DNA  length = 1330
FEATURE                Location/Qualifiers
source                 1..1330
                       mol_type = other DNA

```
                            note = TaCIPK14-4B of KO-3
                            organism = Triticum aestivum
SEQUENCE: 94
atggcaaaca gagggaagat tctaatggag cggtacgagc tgggaagatt gttggggaaa    60
ggaacattcg gcaaggtgca ctatgcaagg agcctagagt cgaaccaaag cgtcgccata   120
aagatgctgg acaaggagaa ggtgctcaag gttgggctct cggagcaaat caggcgtgag   180
gtcacaacca tgcggctggt ggcacacaag aacattgttc agcttcatga ggtcatggcg   240
acacgaaaca aaatatactt tgtcatggag taaaggcggt gagctctttg acaaggttgc   300
aaagagtggc aagctcacag agggtgctgc acataagtat ttccagcagc tcatcagtgc   360
agtggattac tgccacagcc aaggcgtgta tcaccgggat ctcaagctgg agaacctgct   420
cctggatgag aatgagaacc ttaaggtctc agattttgga ctgagcgcac tttcagagtc   480
aaagaggcaa gatggcttgc tccacaccac ctgcggaaca cctgcatatg tagctccgga   540
ggtcatcagc aagacaggtt acgatggtgc gaaatcagat atctggtctt gtggtgttat   600
cctttttgtt cttgttgctg gttatctccc tttccatggt tccaacttga tggacatgta   660
ccggaagatt gaacaaggag atttcaggtg ccccagctgg ttctcacaca aactccagaa   720
gctcttgtgc aagatcctgg accccaatcc aagcaccagg gcatctatcc agaagataaa   780
agagtctacc tggtttcgga aaggtccaag gggcaccctt gcagtgaagg agagaactcc   840
cagtgagaat gtcaccacaa atgctcctcc tacagctggt gtgaggccaa ggaagaacac   900
tcatgaagat gtgcagcccc tgacggtgac aaacttaaat gcctttgaga tcatctcctt   960
ctccacgggg tttgacctgt ccggcctatt catccaagag gactgcagaa aggagacaag  1020
gttcacttca gacaagcctg cttcagccat catctcgaag ctggaatacg ttgcaaaggc  1080
gctgaatctc agggtaagga agaaggacaa tggtgtggtg aagatgcaag caaggaagga  1140
gggaaggaat ggtgctgttc agttagacat ggagatcttc gagatcacac cttcccacca  1200
cctcattgag atgaaacaaa caagtggtga tccgctggag taccgggagc tattggagga  1260
catccggcca gcgctgaagg acatagtctg ggcctggcac ggagatgacc accagcagca  1320
gctagagtag                                                        1330

SEQ ID NO: 95             moltype = DNA  length = 1334
FEATURE                   Location/Qualifiers
source                    1..1334
                          mol_type = other DNA
                          note = TaCIPK14-4D of KO-3
                          organism = Triticum aestivum
SEQUENCE: 95
atggcaaaca gagggaagat tctaatggag cggtacgagc tgggaagatt gttggggaaa    60
ggaacattcg gcaaggtgca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaagg cggtgagctc tttgacaagg   300
ttgcaaagag tggcaagctc acagagggtg ctgcacataa gtatttccag cagctcatca   360
gtgcagtgga ttactgccac agccaaggcg tgtatcaccg ggatctcaag ctggagaacc   420
tgctcctgga tgagaatgag aaccttaagg tctcggattt tggattgagc gccctttcag   480
agtcaaagag gcaagatggc ttgctccaca ccacctgcgg aacacccgca tatgtagctc   540
cggaggtcat cagcaagaca ggttacgatg gtgcaaaatc agatatctgg tcttgtggta   600
ttatcctttt tgttcttgtt gctggttatc tcccttccca tggttccaac ttgatggaca   660
tgtaccggaa gattgagcaa ggagatttca ggtgcccccg gctggttctc acaaaactcc   720
agaagctctt gctcaagatc ctggacccca atccaagcac cagggcatct atccagaaga   780
taaaagagtc tacctggttc cggaaaggtc aaggggcac ccttgcagtg aaggagagaa   840
ctcccagtga gaatgtcatc acaaatgctc tcctacagc tggtgtgagg ccaaggaaga   900
acactcatga agatgtgaag cccctaatgg tgacaaactt aaatgccttt gagatcatct   960
ccttctccac ggggtttgac ctgtccggcc tattcatcca agaggactgc agaaaggaga  1020
caaggttcac ttcagacaag cctgcttcaa ccatcatctc gaagctggaa tatgttgcga  1080
aggcgctgaa tctcagggta aggaagaagg acaatggcgt ggtgaagatg caagcgagga  1140
aggagggaag gaatggtgct gtacagttag acatggagat cttcgagatc acccttccc   1200
accacctcat tgagatgaaa caaacaagtg tgatccgct ggagtaccgg agctattgg   1260
aggacatccg gccagcgctg aaggacatag tctgggcctg gcacggagat gaccaccagc  1320
agcagctaga gtag                                                    1334

SEQ ID NO: 96             moltype = DNA  length = 1336
FEATURE                   Location/Qualifiers
source                    1..1336
                          mol_type = other DNA
                          note = TaCIPK14-4A of KO-4
                          organism = Triticum aestivum
SEQUENCE: 96
atggcaaaca gagggaagat tctaatggag cggtacgagc tgggaagatt gttggggaaa    60
ggaacatttg gcaaggtaca ctatgcaagg agcctagagt cgaaccgaag cgtcgccata   120
aagatgctgg acaaggagaa ggtgctcaag gttgggctct cggagcaaat caggcgtgag   180
gtcacaacca tgcggttggt ggcacacaag aacattgttc agcttcatga ggtcatggcg   240
acacgaaaca aaatatactt tgtcatggag tatgtgaaaa ggcggtgagc tctttgacaa   300
ggttgcaaag agtggcaagc tcacagaggg tgctgcacat aagtatttcc agcagctcat   360
cagtgcagtg gattactgcc acagccaagg cgtgtatcac cgggatctca gctggagaa   420
cctgctcctg gatgagaatg agaacctta ggtctcggat tttggattga gcgcactttc   480
agagtcaaag aggcaagatg gcttgctgca caccacctgc ggaacacccg catatgtagc   540
tccgaggtc atcagcaaga caggttatga tggtgcgaaa tcagatatct ggtcttgtgt   600
tgttatcctt tttgttcttg ttgctggtta tctccctttc catggttcca acttgatgga   660
catgtaccga agattgagc aaggagattt caggtgcccc agctggttct cacacaaact   720
ccagaagctc ttgttcaaga ttctggaccc caatccaagc accagggcat ctatccagaa   780
gataaaagag tctacctggt tccggaaagg tccaaggga acccttgcag tgaaggagag   840
```

```
aactcccagt gagaacgtca ccacaaatgc tcctcctaca gctggtgtga ggccaaggaa    900
gaacactcat gaagatgtga agcccctgat ggtgacaaac ttaaatgcct ttgagatcat    960
ctccttctcc acggggtttg acctgtctgg cctattcatc cgagaggagt gcagaaagga   1020
gacaaggttc acttcagaca agcctgcttc agccatcatc tcgaagctgg aatatgttgc   1080
gaaagcgctg aatctcaggg taaggaagaa ggacaatggc gtggtgaaga tgcaagcgag   1140
gaaggaagga aggaatggtg ctgttcagtt agacatggag atcttcgaga tcacaccttc   1200
ccaccacctc attgagatga aacaaacaag tggtgatcca ctggagtacc gggagctatt   1260
ggaggacatc cggccagcgc tgaaggacat agtctgggcc tggcacggag atgaccacca   1320
ccagcagcta gagtag                                                    1336
```

```
SEQ ID NO: 97              moltype = DNA   length = 1246
FEATURE                    Location/Qualifiers
source                     1..1246
                           mol_type = other DNA
                           note = TaCIPK14-4B of KO-4
                           organism = Triticum aestivum
SEQUENCE: 97
atggcaaaca gagggaagat tctaatggag cggtacgagc tgggaagatt gttggggaaa     60
ggaacattcg gcaaggtgca ctatgcaagg agcctagagt cgaaccaaag cgtcgccata    120
aagatgctgg acaaggagaa ggtgctcaag gttgggctct cggagcaaat caggcgtgag    180
gtcacaacca ggcggtgagc tctttgacaa ggttgcaaag agtggcaagc tcacagaggg    240
tgctgcacat aagtatttcc agcagctcat cagtgcagtg gattactgcc acagccaagg    300
cgtgtatcac cgggatctca agctggagaa cctgctcctg gatgagaatg agaaccttaa    360
ggtctcagat tttggactga gcgcactttc agagtcaaag aggcaagatg cttgctcca    420
caccacctgc ggaacacctg catatgtagc tccggaggtc atcagcaaga caggttacga    480
tggtgcgaaa tcagatatct ggtcttgtgg tgttatcctt tttgttcttg ttgctggtta    540
tctcccttc catggttcca acttgatgga catgtaccgg aagattgaac aaggagattt    600
caggtgcccc agctggttct cacacaaact ccagaagctc ttgtgcaaga tcctggaccc    660
caatccaagc accagggcat ctatccagaa gataaaagag tctacctggt ttcggaaagg    720
tccaagggc acccttgcag tgaaggagag aactcccagt gagaatgtca ccacaaatgc    780
tcctcctaca gctggtgtga ggccaaggaa gaacactcat gaagatgtgc agcccctgac    840
ggtgacaaac ttaaatgcct ttgagatcat ctccttctcc acggggtttg acctgtccgg    900
cctattcatc caagaggact gcagaaagga gacaaggttc acttcagaca agcctgcttc    960
agccatcatc tcgaagctgg aatacgttgc aaaggcgctg aatctcaggg taaggaagaa   1020
ggacaatggt gtggtgaaga tgcaagcaag gaaggaggga aggaatggtg ctgttcagtt   1080
agacatggag atcttcgaga tcacaccttc ccaccacctc attgagatga aacaaacaag   1140
tggtgatccg ctggagtacc gggagctatt ggaggacatc cggccagcgc tgaaggacat   1200
agtctgggcc tggcacggag atgaccacca gcagcagcta gagtag                  1246
```

```
SEQ ID NO: 98              moltype = DNA   length = 1324
FEATURE                    Location/Qualifiers
source                     1..1324
                           mol_type = other DNA
                           note = TaCIPK14-4D of KO-4
                           organism = Triticum aestivum
SEQUENCE: 98
atggcaaaca gagggaagat tctaatggag cggtacgagc tgggaagatt gttggggaaa     60
ggaacattcg gcaaggtgca ctatgcaagg agcctagagt cgaaccgaag cgtcgccata    120
aagatgctgg acaaggagaa ggtgctcaag gttgggctct cggagcaaat caggcgtgag    180
gtcgttggtg gcacacaaga acattgttca gcttcatgag gtcatggcga cacgaaacaa    240
aatatacttt gtcatggagt atgtgaaagg cggtgagctc tttgacaagg ttgcaaagag    300
tggcaagctc acagagggtg ctgcacataa gtatttccag cagctcatca gtgcagtgga    360
ttactgccac agccaaggcg tgtatcaccg ggatctcaag ctggagaacc tgctcctgga    420
tgagaatgag aaccttaagg tctcggattt tggattgagc gcccttcag agtcaaagag    480
gcaagatggc ttgctccaca ccacctgcgg aacacccgca tatgtagctc cggaggtcat    540
cagcaagaca ggttacgatg gtgcaaatc agatatctgg tcttgtggtg ttatcctttt    600
tgttcttgtt gctggttatc tccctttcca tggttccaac ttgatggaca tgtaccggaa    660
gattgagcaa ggagatttca ggtgcccgg ctggttctca cacaaactcc agaagctctt    720
gctcaagatc ctgacccca tccaagcac cagggcatct atccagaaga taaaagagtc    780
tacctggttc cggaaaggtc caagggcac ccttgcagtg aaggagagaa ctcccagtga    840
gaatgtcatc acaaatgctc ctcctacagc tggtgtgagg ccaaggaaga acactcatga    900
agatgtgaag cccctaatgg tgacaaactt aaatgccttt gagatcatct ccttctccac    960
ggggtttgac ctgtccggcc tattcatcca gaggactgc agaaaggaga caaggttcac   1020
ttcagacaag cctgcttcaa ccatcatctc gaagctgaa tatgttgcga ggcgctgaa    1080
tctcagggta aggaagaagg acaatggcgt ggtgaagatg caagcgagga aggagggaag   1140
gaatggtgct gtacagttag acatggagat cttcgagatc acccttccc accacctcat    1200
tgagatgaaa caaacaagtg gtgatccgct ggagtaccgg gagctattgg aggacatccg   1260
gccagcgctg aaggacatag tctgggcctg cacggagat gaccaccagc agcagctaga   1320
gtag                                                               1324
```

```
SEQ ID NO: 99              moltype = DNA   length = 1336
FEATURE                    Location/Qualifiers
source                     1..1336
                           mol_type = other DNA
                           note = TaCIPK14-4A of KO-5
                           organism = Triticum aestivum
SEQUENCE: 99
atggcaaaca gagggaagat tctaatggag cggtacgagc tgggaagatt gttggggaaa     60
ggaacatttg gcaaggtaca ctatgcaagg agcctagagt cgaaccgaag cgtcgccata    120
```

```
aagatgctgg acaaggagaa ggtgctcaag gttgggctct cggagcaaat caggcgtgag    180
gtcacaacca tgcggttggt ggcacacaag aacattgttc agcttcatga ggtcatggcg    240
acacgaaaca aaatatactt tgtcatggag tatgtgaaaa ggcggtgagc tctttgacaa    300
ggttgcaaag agtggcaagc tcacagaggg tgctgcacat aagtatttcc agcagctcat    360
cagtgcagtg gattactgcc acagccaagg cgtgtatcac cgggatctca agctggagaa    420
cctgctcctg gatgagaatg agaaccttaa ggtctcggat tttggattga gcgcactttc    480
agagtcaaag aggcaagatg gcttgctgca caccacctgc ggaacacccg catatgtagc    540
tccggaggtc atcagcaaga caggttatga tggtgcgaaa tcagatatct ggtcttgtgg    600
tgttatcctt tttgttcttg ttgctggtta tctccctttc catggttcca acttgatgga    660
catgtaccgg aagattgagc aaggagattt caggtgcccc agctggttct cacacaaact    720
ccagaagctc ttgttcaaga ttctggaccc caatccaagc accagggcat ctatccagaa    780
gataaaagag tctacctggt tccggaaagg tccaaggggga acccttgcag tgaaggagag    840
aactcccagt gagaacgtca ccacaaatgc tcctcctaca gctggtgtga ggccaaggaa    900
gaacactcat gaagatgtga agcccctgat ggtgacaaac ttaaatgcct ttgagatcat    960
ctccttctcc acgggggtttg acctgtctgg cctattcatc cgagaggagt gcagaaagga   1020
gacaaggttc acttcagaca agcctgcttc agccatcatc tcgaagctgg aatatgttgc   1080
gaaagcgctg aatctcaggg taaggaagaa ggacaatggc gtggtgaaga tgcaagcgag   1140
gaaggaagga aggaatggtg ctgttcagtt agacatggag atcttcgaga tcacaccttc   1200
ccaccacctc attgagatga aacaaacaag tggtgatcca ctggagtacc gggagctatt   1260
ggaggacatc cggccagcgc tgaaggacat agtctgggcc tggcacggag atgaccacca   1320
ccagcagcta gagtag                                                    1336
```

```
SEQ ID NO: 100          moltype = DNA   length = 1336
FEATURE                 Location/Qualifiers
source                  1..1336
                        mol_type = other DNA
                        note = TaCIPK14-4B of KO-5
                        organism = Triticum aestivum
SEQUENCE: 100
atggcaaaca gagggaagat tctaatggag cggtacgagc tgggaagatt gttggggaaa     60
ggaacatttg gcaaggtaca ctatgcaagg agcctagagt cgaaccgaag cgtcgccata    120
aagatgctgg acaaggagaa ggtgctcaag gttgggctct cggagcaaat caggcgtgag    180
gtcacaacca tgcggttggt ggcacacaag aacattgttc agcttcatga ggtcatggcg    240
acacgaaaca aaatatactt tgtcatggag tatgtgaaaa ggcggtgagc tctttgacaa    300
ggttgcaaag agtggcaagc tcacagaggg tgctgcacat aagtatttcc agcagctcat    360
cagtgcagtg gattactgcc acagccaagg cgtgtatcac cgggatctca agctggagaa    420
cctgctcctg gatgagaatg agaaccttaa ggtctcggat tttggattga gcgcactttc    480
agagtcaaag aggcaagatg gcttgctgca caccacctgc ggaacacccg catatgtagc    540
tccggaggtc atcagcaaga caggttatga tggtgcgaaa tcagatatct ggtcttgtgg    600
tgttatcctt tttgttcttg ttgctggtta tctccctttc catggttcca acttgatgga    660
catgtaccgg aagattgagc aaggagattt caggtgcccc agctggttct cacacaaact    720
ccagaagctc ttgttcaaga ttctggaccc caatccaagc accagggcat ctatccagaa    780
gataaaagag tctacctggt tccggaaagg tccaaggggga acccttgcag tgaaggagag    840
aactcccagt gagaacgtca ccacaaatgc tcctcctaca gctggtgtga ggccaaggaa    900
gaacactcat gaagatgtga agcccctgat ggtgacaaac ttaaatgcct ttgagatcat    960
ctccttctcc acgggggtttg acctgtctgg cctattcatc cgagaggagt gcagaaagga   1020
gacaaggttc acttcagaca agcctgcttc agccatcatc tcgaagctgg aatatgttgc   1080
gaaagcgctg aatctcaggg taaggaagaa ggacaatggc gtggtgaaga tgcaagcgag   1140
gaaggaagga aggaatggtg ctgttcagtt agacatggag atcttcgaga tcacaccttc   1200
ccaccacctc attgagatga aacaaacaag tggtgatcca ctggagtacc gggagctatt   1260
ggaggacatc cggccagcgc tgaaggacat agtctgggcc tggcacggag atgaccacca   1320
ccagcagcta gagtag                                                    1336
```

```
SEQ ID NO: 101          moltype = DNA   length = 1324
FEATURE                 Location/Qualifiers
source                  1..1324
                        mol_type = other DNA
                        note = TaCIPK14-4D of KO-5
                        organism = Triticum aestivum
SEQUENCE: 101
atggcaaaca gagggaagat tctaatggag cggtacgagc tgggaagatt gttggggaaa     60
ggaacattcg gcaaggtgca ctatgcaagg agcctagagt cgaaccgaag cgtcgccata    120
aagatgctgg acaaggagaa ggtgctcaag gttgggctct cggagcaaat caggcgtgag    180
gtcgttggtg gcacacaaga acattgttca gcttcatgag gtcatggcga cacgaaaact    240
aatatacttt gtcatggagt atgtgaaagg cggtgagctc tttgacaagg ttgcaaagag    300
tggcaagctc acagagggtg ctgcacataa gtatttccag cagctcatca gtgcagtgga    360
ttactgccac agccaaggcg tgtatcaccg gatctcaag ctggagaacc tgctcctgga     420
tgagaatgag aaccttaagg tctcggattt tggattgagc gcccttcag agtcaaagag     480
gcaagatggc ttgctcccaca ccacctgcgg aacacccga tatgtcggag gtcac         540
cagcaagaca ggttacgatg gtgcaaaatc agatatctgg tcttgtggtg ttatcctttt    600
tgttcttgtt gctggttatc tccctttcca tggttccaac ttgatggaca tgtaccggaa    660
gattgagcaa ggagatttca ggtgcccgg ctggttctca cacaaactcc agaagctctt     720
gctcaagatc ctgaccccca tccaagcac agggcatct atccagaaga taaaagagtc      780
tacctggttc cggaaaggtc caagggggcac ccttgcagtg aggagagac tcccagtga     840
gaatgtcatc acaaatgctc tcctacagc tggtgtgagg ccaaggaaga acactcatga     900
agatgtgaag cccctaatgg tgacaaactt aaatgccttt gagatcatct ccttctccac    960
gggggtttgac ctgtccggcc tattcatcca agaggactgc agaaggagac aaggttcac   1020
ttcagacaag cctgcttcaa ccatcatctc gaagctggaa tatgttgcga aggcgctgaa   1080
tctcagggta aggaagaagg acaatggcgt ggtgaagatg caagcgagga aggagggaag   1140
```

-continued

```
gaatggtgct gtacagttag acatggagat cttcgagatc acaccttccc accacctcat   1200
tgagatgaaa caaacaagtg gtgatccgct ggagtaccgg gagctattgg aggacatccg   1260
gccagcgctg aaggacatag tctgggcctg gcacggagat gaccaccagc agcagctaga   1320
gtag                                                                1324

SEQ ID NO: 102              moltype = AA   length = 105
FEATURE                     Location/Qualifiers
source                      1..105
                            mol_type = protein
                            note = Deduced amino acid sequence fragment of TaCIPK14-4A
                             of Fielder
                            organism = synthetic construct
SEQUENCE: 102
IRREVTTMRL VAHKNIVQLH EVMATRNKIY FVMEYVKGGE LFDKVAKSGK LTEGAAHKYF   60
QQLISAVDYC HSQGVYHRDL KLENLLLDEN ENLKVSDFGL SALSE                    105

SEQ ID NO: 103              moltype = AA   length = 106
FEATURE                     Location/Qualifiers
source                      1..106
                            mol_type = protein
                            note = Deduced amino acid sequence fragment of TaCIPK14-4B
                             of Fielder
                            organism = synthetic construct
SEQUENCE: 103
IRREVTTMRL VAHKNIVQLH EVMATRTNKI YFVMEYVKGG ELFDKVAKSG KLTEGAAHKY   60
FQQLISAVDY CHSQGVYHRD LKLENLLLDE NENLKVSDFG LSALSE                   106

SEQ ID NO: 104              moltype = AA   length = 105
FEATURE                     Location/Qualifiers
source                      1..105
                            mol_type = protein
                            note = Deduced amino acid sequence fragment of TaCIPK14-4D
                             of Fielder
                            organism = synthetic construct
SEQUENCE: 104
IRREVTTMRL VAHKNIVQLH EVMATRNKIY FVMEYVKGGE LFDKVAKSGK LTEGAAHKYF   60
QQLISAVDYC HSQGVYHRDL KLENLLLDEN ENLKVSDFGL SALSE                    105

SEQ ID NO: 105              moltype = AA   length = 39
FEATURE                     Location/Qualifiers
source                      1..39
                            mol_type = protein
                            note = Deduced amino acid sequence fragment of TaCIPK14-4A
                             of KO-1
                            organism = synthetic construct
SEQUENCE: 105
IRREVTTMRL VAHKNIVQLH EVMATRNKIY FVMEYVKRR                          39

SEQ ID NO: 106              moltype = AA   length = 34
FEATURE                     Location/Qualifiers
source                      1..34
                            mol_type = protein
                            note = Deduced amino acid sequence fragment of TaCIPK14-4B
                             of KO-1
                            organism = synthetic construct
SEQUENCE: 106
IRREVTTMRL VAHKNIVQLH EVMATRNKIY FVME                               34

SEQ ID NO: 107              moltype = AA   length = 93
FEATURE                     Location/Qualifiers
source                      1..93
                            mol_type = protein
                            note = Deduced amino acid sequence fragment of TaCIPK14-4D
                             of KO-1
                            organism = synthetic construct
SEQUENCE: 107
MANRGKILME RYELGRLLGK GTFGKVHYAR SLESNRSVAI KMLDKEKVLK VGLSEQIRRE   60
VTTMRLVAHK NIVQLHEVMA TRNKIYFVME YRR                                93

SEQ ID NO: 108              moltype = AA   length = 39
FEATURE                     Location/Qualifiers
source                      1..39
                            mol_type = protein
                            note = Deduced amino acid sequence fragment of TaCIPK14-4A
                             of KO-2
                            organism = synthetic construct
SEQUENCE: 108
IRREVTTMRL VAHKNIVQLH EVMATRNKIY FVMEYVKRR                          39
```

-continued

```
SEQ ID NO: 109          moltype = AA  length = 39
FEATURE                 Location/Qualifiers
source                  1..39
                        mol_type = protein
                        note = Deduced amino acid sequence fragment of TaCIPK14-4B
                         of KO-2
                        organism = synthetic construct
SEQUENCE: 109
IRREVTTMRL VAHKNIVQLH EVMATRNKIY FVMEYVKRR                                39

SEQ ID NO: 110          moltype = AA  length = 37
FEATURE                 Location/Qualifiers
source                  1..37
                        mol_type = protein
                        note = Deduced amino acid sequence fragment of TaCIPK14-4D
                         of KO-2
                        organism = synthetic construct
SEQUENCE: 110
IRREVTTMRL VAHKNIVQLH EVMATRNKIY FVMEYRR                                  37

SEQ ID NO: 111          moltype = AA  length = 39
FEATURE                 Location/Qualifiers
source                  1..39
                        mol_type = protein
                        note = Deduced amino acid sequence fragment of TaCIPK14-4A
                         of KO-3
                        organism = synthetic construct
SEQUENCE: 111
IRREVTTMRL VAHKNIVQLH EVMATRNKIY FVMEYVKRR                                39

SEQ ID NO: 112          moltype = AA  length = 34
FEATURE                 Location/Qualifiers
source                  1..34
                        mol_type = protein
                        note = Deduced amino acid sequence fragment of TaCIPK14-4B
                         of KO-3
                        organism = synthetic construct
SEQUENCE: 112
IRREVTTMRL VAHKNIVQLH EVMATRNKIY FVME                                     34

SEQ ID NO: 113          moltype = AA  length = 99
FEATURE                 Location/Qualifiers
source                  1..99
                        mol_type = protein
                        note = Deduced amino acid sequence fragment of TaCIPK14-4D
                         of KO-3
                        organism = synthetic construct
SEQUENCE: 113
IRREVTTMRL VAHKNIVQLH EVMATRNKIY FVMEYVKAVS SLTRLQRVAS SQRVLHISIS  60
SSSSVQWITA TAKACITGIS SWRTCSWMRM RTLRSRILD                                99

SEQ ID NO: 114          moltype = AA  length = 39
FEATURE                 Location/Qualifiers
source                  1..39
                        mol_type = protein
                        note = Deduced amino acid sequence fragment of TaCIPK14-4A
                         of KO-4
                        organism = synthetic construct
SEQUENCE: 114
IRREVTTMRL VAHKNIVQLH EVMATRNKIY FVMEYVKRR                                39

SEQ ID NO: 115          moltype = AA  length = 9
FEATURE                 Location/Qualifiers
source                  1..9
                        mol_type = protein
                        note = Deduced amino acid sequence fragment of TaCIPK14-4B
                         of KO-4
                        organism = synthetic construct
SEQUENCE: 115
IRREVTTRR                                                                  9

SEQ ID NO: 116          moltype = AA  length = 16
FEATURE                 Location/Qualifiers
source                  1..16
                        mol_type = protein
                        note = Deduced amino acid sequence fragment of TaCIPK14-4D
                         of KO-4
                        organism = synthetic construct
SEQUENCE: 116
```

-continued

```
IRREVVGGTQ EHCSAS                                                        16

SEQ ID NO: 117          moltype = AA  length = 39
FEATURE                 Location/Qualifiers
source                  1..39
                        mol_type = protein
                        note = Deduced amino acid sequence fragment of TaCIPK14-4A
                         of KO-5
                        organism = synthetic construct
SEQUENCE: 117
IRREVTTMRL VAHKNIVQLH EVMATRNKIY FVMEYVKRR                               39

SEQ ID NO: 118          moltype = AA  length = 39
FEATURE                 Location/Qualifiers
source                  1..39
                        mol_type = protein
                        note = Deduced amino acid sequence fragment of TaCIPK14-4B
                         of KO-5
                        organism = synthetic construct
SEQUENCE: 118
IRREVTTMRL VAHKNIVQLH EVMATRNKIY FVMEYVKRR                               39

SEQ ID NO: 119          moltype = AA  length = 16
FEATURE                 Location/Qualifiers
source                  1..16
                        mol_type = protein
                        note = Deduced amino acid sequence fragment of TaCIPK14-4D
                         of KO-5
                        organism = synthetic construct
SEQUENCE: 119
IRREVVGGTQ EHCSAS                                                        16

SEQ ID NO: 120          moltype = AA  length = 95
FEATURE                 Location/Qualifiers
source                  1..95
                        mol_type = protein
                        note = Deduced amino acid sequence TaCIPK14-4A of KO-1
                        organism = synthetic construct
SEQUENCE: 120
MANRGKILME RYELGRLLGK GTFGKVHYAR SLESNRSVAI KMLDKEKVLK VGLSEQIRRE  60
VTTMRLVAHK NIVQLHEVMA TRNKIYFVME YVKRR                                   95

SEQ ID NO: 121          moltype = AA  length = 90
FEATURE                 Location/Qualifiers
source                  1..90
                        mol_type = protein
                        note = Deduced amino acid sequence TaCIPK14-4B of KO-1
                        organism = synthetic construct
SEQUENCE: 121
MANRGKILME RYELGRLLGK GTFGKVHYAR SLESNQSVAI KMLDKEKVLK VGLSEQIRRE  60
VTTMRLVAHK NIVQLHEVMA TRNKIYFVME                                         90

SEQ ID NO: 122          moltype = AA  length = 93
FEATURE                 Location/Qualifiers
source                  1..93
                        mol_type = protein
                        note = Deduced amino acid sequence TaCIPK14-4D of KO-1
                        organism = synthetic construct
SEQUENCE: 122
MANRGKILME RYELGRLLGK GTFGKVHYAR SLESNRSVAI KMLDKEKVLK VGLSEQIRRE  60
VTTMRLVAHK NIVQLHEVMA TRNKIYFVME YRR                                     93

SEQ ID NO: 123          moltype = AA  length = 95
FEATURE                 Location/Qualifiers
source                  1..95
                        mol_type = protein
                        note = Deduced amino acid sequence TaCIPK14-4A of KO-2
                        organism = synthetic construct
SEQUENCE: 123
MANRGKILME RYELGRLLGK GTFGKVHYAR SLESNRSVAI KMLDKEKVLK VGLSEQIRRE  60
VTTMRLVAHK NIVQLHEVMA TRNKIYFVME YVKRR                                   95

SEQ ID NO: 124          moltype = AA  length = 95
FEATURE                 Location/Qualifiers
source                  1..95
                        mol_type = protein
                        note = Deduced amino acid sequence TaCIPK14-4B of KO-2
                        organism = synthetic construct
SEQUENCE: 124
```

-continued

```
MANRGKILME RYELGRLLGK GTFGKVHYAR SLESNQSVAI KMLDKEKVLK VGLSEQIRRE  60
VTTMRLVAHK NIVQLHEVMA TRNKIYFVME YVKRR                            95

SEQ ID NO: 125          moltype = AA  length = 93
FEATURE                 Location/Qualifiers
source                  1..93
                        mol_type = protein
                        note = Deduced amino acid sequence TaCIPK14-4D of KO-2
                        organism = synthetic construct
SEQUENCE: 125
MANRGKILME RYELGRLLGK GTFGKVHYAR SLESNRSVAI KMLDKEKVLK VGLSEQIRRE  60
VTTMRLVAHK NIVQLHEVMA TRNKIYFVME YRR                              93

SEQ ID NO: 126          moltype = AA  length = 95
FEATURE                 Location/Qualifiers
source                  1..95
                        mol_type = protein
                        note = Deduced amino acid sequence TaCIPK14-4A of KO-3
                        organism = synthetic construct
SEQUENCE: 126
MANRGKILME RYELGRLLGK GTFGKVHYAR SLESNRSVAI KMLDKEKVLK VGLSEQIRRE  60
VTTMRLVAHK NIVQLHEVMA TRNKIYFVME YVKRR                            95

SEQ ID NO: 127          moltype = AA  length = 90
FEATURE                 Location/Qualifiers
source                  1..90
                        mol_type = protein
                        note = Deduced amino acid sequence TaCIPK14-4B of KO-3
                        organism = synthetic construct
SEQUENCE: 127
MANRGKILME RYELGRLLGK GTFGKVHYAR SLESNQSVAI KMLDKEKVLK VGLSEQIRRE  60
VTTMRLVAHK NIVQLHEVMA TRNKIYFVME                                  90

SEQ ID NO: 128          moltype = AA  length = 155
FEATURE                 Location/Qualifiers
source                  1..155
                        mol_type = protein
                        note = Deduced amino acid sequence TaCIPK14-4D of KO-3
                        organism = synthetic construct
SEQUENCE: 128
MANRGKILME RYELGRLLGK GTFGKVHYAR SLESNRSVAI KMLDKEKVLK VGLSEQIRRE  60
VTTMRLVAHK NIVQLHEVMA TRNKIYFVME YVKAVSSLTR LQRVASSQRV LHISISSSSS  120
VQWITATAKA CITGISSWRT CSWMRMRTLR SRILD                            155

SEQ ID NO: 129          moltype = AA  length = 95
FEATURE                 Location/Qualifiers
source                  1..95
                        mol_type = protein
                        note = Deduced amino acid sequence TaCIPK14-4A of KO-4
                        organism = synthetic construct
SEQUENCE: 129
MANRGKILME RYELGRLLGK GTFGKVHYAR SLESNRSVAI KMLDKEKVLK VGLSEQIRRE  60
VTTMRLVAHK NIVQLHEVMA TRNKIYFVME YVKRR                            95

SEQ ID NO: 130          moltype = AA  length = 65
FEATURE                 Location/Qualifiers
source                  1..65
                        mol_type = protein
                        note = Deduced amino acid sequence TaCIPK14-4B of KO-4
                        organism = synthetic construct
SEQUENCE: 130
MANRGKILME RYELGRLLGK GTFGKVHYAR SLESNQSVAI KMLDKEKVLK VGLSEQIRRE  60
VTTRR                                                            65

SEQ ID NO: 131          moltype = AA  length = 72
FEATURE                 Location/Qualifiers
source                  1..72
                        mol_type = protein
                        note = Deduced amino acid sequence TaCIPK14-4D of KO-4
                        organism = synthetic construct
SEQUENCE: 131
MANRGKILME RYELGRLLGK GTFGKVHYAR SLESNRSVAI KMLDKEKVLK VGLSEQIRRE  60
VVGGTQEHCS AS                                                    72

SEQ ID NO: 132          moltype = AA  length = 95
FEATURE                 Location/Qualifiers
source                  1..95
                        mol_type = protein
                        note = Deduced amino acid sequence TaCIPK14-4A of KO-5
```

-continued

```
                          organism = synthetic construct
SEQUENCE: 132
MANRGKILME RYELGRLLGK GTFGKVHYAR SLESNRSVAI KMLDKEKVLK VGLSEQIRRE   60
VTTMRLVAHK NIVQLHEVMA TRNKIYFVME YVKRR                              95

SEQ ID NO: 133           moltype = AA  length = 95
FEATURE                  Location/Qualifiers
source                   1..95
                         mol_type = protein
                         note = Deduced amino acid sequence TaCIPK14-4B of KO-5
                         organism = synthetic construct
SEQUENCE: 133
MANRGKILME RYELGRLLGK GTFGKVHYAR SLESNQSVAI KMLDKEKVLK VGLSEQIRRE   60
VTTMRLVAHK NIVQLHEVMA TRNKIYFVME YVKRR                              95

SEQ ID NO: 134           moltype = AA  length = 72
FEATURE                  Location/Qualifiers
source                   1..72
                         mol_type = protein
                         note = Deduced amino acid sequence TaCIPK14-4D of KO-5
                         organism = synthetic construct
SEQUENCE: 134
MANRGKILME RYELGRLLGK GTFGKVHYAR SLESNRSVAI KMLDKEKVLK VGLSEQIRRE   60
VVGGTQEHCS AS                                                       72
```

METHOD FOR IMPROVING WHEAT RESISTANCE TO FUSARIUM HEAD BLIGHT (FHB) BY GENOME EDITING

CROSS-REFERENCE TO RELATED APPLICATION

This patent application is a national phase application of PCT application No. PCT/CN2022/143089, filed on Dec. 29, 2022, which claims the benefit and priority of Chinese Patent Application No. 202210674184.4 filed with the China National Intellectual Property Administration on Jun. 15, 2022, both of which are incorporated by reference herein in their entirety as part of the present application.

REFERENCE TO SEQUENCE LISTING

A computer readable XML file entitled "GWPCTP20230705602_seqlist", that was created on Sep. 18, 2023, with a file size of about 174,597 bytes, contains the sequence listing for this application, has been filed with this application, and is hereby incorporated by reference in its entirety.

TECHNICAL FIELD

The present disclosure relates to the technical field of breeding of disease-resistant varieties, and in particular to a method for improving wheat resistance to *Fusarium* head blight (FHB) by genome editing.

BACKGROUND

*Fusarium* head blight (FHB) is a fungal disease that severely disrupts global wheat production, causing billions of dollars in losses during wheat production each year (McMullen et al., 2012). Since 2000, wheat FHB epidemics have become more severe due to global warming, and the number of years of wheat FHB epidemics has significantly increased, with yield losses as high as 70% in some fields (Yerkovich et al., 2017). Since 2010, the area of wheat FHB has been increasing, and according to data from the National Center for Agricultural Technology Extension (NCATE), the annual average area of wheat FHB in China from 2011-2015 amounted to 82 million mu. Particularly, in 2012, the incidence of wheat FHB was extensive and the extent was historically rare, with an incidence area of 140 million mu (www.natesc.org.cn/). Chemical control is currently major means for controlling wheat FHB in the field. However, the long-term use of a single agent leads to resistance of pathogen to fungicides, and breeding disease-resistant varieties is the most economical, effective, and environmentally friendly strategy to prevent FHB. Although breeders have improved wheat resistance to FHB through traditional breeding approaches, there is still a lack of stable FHB resistant varieties (Wang et al., 2020). Therefore, it is still the main task to mine for genes associated with FHB resistance and to breed stable resistant varieties in the breeding of wheat with FHB resistance. The enhancement of wheat disease resistance should be balanced with wheat yield in order to meet the needs of wheat production and population growth.

Susceptibility genes(S) are necessary for pathogens and hosts to establish affinity interactions, and at the same time, they are the key for pathogens to successfully invade the host. It has become an important tool to utilize plant susceptibility genes to improve plant disease resistance in the breeding process, and the gene editing technology Clustered Regularly Interspaced Short Palindromic Repeats (CRISPR) can realize non-transgenic editing of susceptibility genes, thus reducing the potential risks associated with the transfer of exogenous genes. The editing of susceptibility genes can be utilized to rapidly improve the disease resistance of crops, thus facilitating the development of disease-resistance breeding.

In summary, the current technical problems are as following.

Wheat susceptibility gene resources are scarce and cannot meet the current breeding needs, and the traditional genetic improvement method of screening susceptibility genes is time-consuming, so how should we quickly screen to obtain wheat susceptibility genes and improve the wheat varieties?

As editing of susceptibility genes in the wheat variety Fielder was found to significantly improve disease resistance in wheat, can susceptibility genes be edited in major domestic cultivars, and can edition of susceptibility genes in cultivars improve their disease resistance?

Editing of wheat susceptibility genes can significantly increase wheat resistance to pathogens. However, editing of susceptibility genes may lead to the occurrence of wheat immune overload and depletion of nutrients during its own growth and development, so how should one balance wheat resistance to disease and maintenance of normal growth and development?

SUMMARY

It is an object of the present disclosure to provide a method for improving wheat resistance to FHB in by genome editing.

In a first aspect, the present disclosure is drawn to use of TaCIPK14 protein or a related biomaterial thereto in regulation of plant resistance to FHB.

The TaCIPK14 protein is a TaCIPK14-4A protein, a TaCIPK14-4B protein and/or a TaCIPK14-4D protein;

the TaCIPK14-4A protein is selected from the group consisting of (A1) a protein having the amino acid sequence of SEQ ID NO: 4;

(A2) a wheat-derived protein having the amino acid sequence of SEQ ID NO: 4 with one or more substitutions and/or deletions and/or additions of amino acid residues, and having the same function;

(A3) a wheat-derived protein having at least 99%, at least 95%, at least 90%, at least 85%, or at least 80% identity to the amino acid sequence of any of (A1)-(A2) and having the same function; and (A4) a fusion protein obtained by attaching a protein tag to an N- and/or C-terminus of the protein of any one of (A1)-(A3);

the TaCIPK14-4B protein is selected from the group consisting of (B1) a protein having the amino acid sequence of SEQ ID NO: 5;

(B2) a wheat-derived protein having the amino acid sequence of SEQ ID NO: 5 with one or more substitutions and/or deletions and/or additions of amino acid residues, and having the same function;

(B3) a wheat-derived protein having at least 99%, at least 95%, at least 90%, at least 85%, or at least 80% identity to the amino acid sequence of any of (B1)-(B2) and having the same function; and (B4) a fusion protein obtained by attaching a protein tag to an N- and/or C-terminus of the protein of any one of (B1)-(B3);

the TaCIPK14-4C protein is selected from the group consisting of (C1) a protein having the amino acid sequence of SEQ ID NO: 6;

(C2) a wheat-derived protein having the amino acid sequence of SEQ ID NO: 6 with one or more substitutions and/or deletions and/or additions of amino acid residues, and having the same function;

(C3) a wheat-derived protein having at least 99%, at least 95%, at least 90%, at least 85%, or at least 80% identity to the amino acid sequence of any of (C1)-(C2) and having the same function; and (C4) a fusion protein obtained by attaching a protein tag to an N- and/or C-terminus of the protein of any one of (C1)-(C3).

In the above description of proteins, the term 'protein tag' refers to a polypeptide or protein expressed in fusion with a target protein using the technology of DNA recombination in vitro to facilitate expression, detection, tracing and/or purification of the target protein. The protein tag is selected from the group consisting of a Flag-tag, a His-tag, an MBP-tag, an HA-tag, a myc-tag, a GST-tag and/or a SUMO-tag.

In the above description of proteins, the term 'identity' refers to the identity of the amino acid sequence. Identity of amino acid sequences can be determined using alignment search tools on the internet, such as BLAST of the NCBI homepage website. For example, this can be done in Advanced BLAST 2.1 by using blastp as program, with an Expect value being 10, all Filters being OFF, BLOSUM62 as Matrix, and Gap existence cost, Per residue gap cost and Lambda ratio set to 11, 1 and 0.85 (default values), respectively, and performing search to calculate the identity of a pair of amino acid sequences, so that the identity (%) is obtained.

In the above description of proteins, 'at least 95% identity' may be at least 96%, 97%, 98% identity. 'At least 90% identity' may be at least 91%, 92%, 93%, 94% identity. 'At least 85% identity' may be at least 86%, 87%, 88%, 89% identity. 'At least 80% identity' may be at least 81%, 82%, 83%, or 84% identity.

The related biomaterial includes a nucleic acid molecule capable of expressing the TaCIPK14 protein, or an expression cassette, a recombinant vector, a recombinant microorganism or a transgenic cell line containing the nucleic acid molecule.

The expression cassette is a DNA capable of expressing TaCIPK14 in a host cell, and the DNA may include not only a promoter that initiates transcription of TaCIPK14, but also a terminator that terminates transcription of the TaCIPK14 gene. Furthermore, the expression cassette may also include an enhancer sequence. Promoters that can be used in the present disclosure include, but are not limited to constitutive promoters, tissue-, organ- and development-specific promoters, and inducible promoters. Exemplary promoters include, but are not limited to the Ubiqutin promoter (pUbi); the constitutive 35S promoter of cauliflower mosaic virus (CaMV); the trauma-inducible promoter from tomato, leucine aminopeptidase ("LAP", Chao et al. (1999) Plant Physiol 120:979-992); the chemically inducible promoter, pathogenesis-related 1 (PR1) from tobacco, which is induced by salicylic acid and BTH (benzothiadiazole-7-thioglycolic acid S-methyl ester); tomato protease inhibitor II promoter (PIN2) or LAP promoter (both inducible with cockroach jasmonate); heat shock promoter (U.S. Pat. No. 5,187,267); tetracycline-inducible promoter (U.S. Pat. No. 5,057,422); embryo-specific promoter, such as seed-specific promoter pF128 from foxtail millet (CN101063139B (CN Patent NO: 200710099169.7)), embryonic storage protein-specific promoters (e.g., promoters for legumin from common bean, napin, oleosin, and beta conglycinin from soybean (Beachy et al. (1985) EMBO J. 4:3047-3053)). They can be used alone or in combination with other plant promoters. All references cited herein are incorporated in their entirety. Suitable transcriptional terminators include, but are not limited to the Nopaline Synthase terminator (NOS terminator), the CaMV 35S terminator, the tml terminator, the pea rbcS E9 terminator, and mannopine synthase (Mas) or octopine synthase (Ocs) terminators (see, e.g., Odell et al. ($I^{985}$) Nature 313:810; Rosenberg et al. (1987) Gene, 56:125; Guerineau et al. (1991) Mol. Gen. Genet, 262:141; Proudfoot (1991) Cell, 64:671; Sanfacon et al. Genes Dev. Cell, 2:1261; Munroe et al. (1990) Gene, 91:151; Ballad et al. (1989) Nucleic Acids Res. 17:7891; Joshi et al. (1987) Nucleic Acid Res., 15:9627).

A recombinant expression vector containing the TaCIPK14 gene expression cassette is constructed. The plant expression vectors utilized may be binary *Agrobacterium* vectors or Gateway system vectors, etc., such as pBin438, pCAMBIA1302, pCAMBIA2301, pCAMBIA1301, pCAMBIA1300, pBI121, pGWB411, pGWB412, pGWB405, pCAMBIA1391-Xa or pCAMBIA1391-Xb. When TaCIPK14 is used to construct recombinant expression vectors, any one of the enhancement, constitutive, tissue-specific, or inducible promoters, such as the CaMV) 35S promoter, the Ubiqutin promoter (pUbi), etc., can be added before its transcription start nucleotide etc., which can be used alone or in combination with other plant promoters; furthermore, when the gene of the present disclosure is used to construct plant expression vectors, enhancers including translational enhancers and transcriptional enhancers can also be used. These enhancers can be located in the region where the ATG start codons is located or a neighboring region, provided that the region shares the same reading frame with the coding sequence in order to ensure the correct translation of the whole sequence. The sources of the translation control signals and start codons are wide-ranging and can be natural or synthetic. Translation initiation regions can be derived from transcription initiation regions or structural genes.

In order to facilitate the identification and screening of transgenic plant cells or plants, the plant expression vectors used can be processed, such as incorporating genes encoding enzymes or luminescent compounds that can produce color changes (GUS genes, luciferase genes, etc.), antibiotic-resistant markers (gentamicin markers, kanamycin markers, etc.), or chemical reagent-resistant markers (e.g., herbicide-resistant genes), etc., which can be expressed in plants.

In the use, the vector may be a plasmid, a cosmid, a phage or a viral vector.

In the use, the microorganisms may be yeast, bacteria, algae or fungi. The bacteria may be selected from the group consisting of genera *Escherichia, Erwinia, Agrobacterium* (e.g. *Agrobacterium rhizogenes* EHA105), *Flavobacterium, Alcaligenes, Pseudomonas*, and *Bacillus.*

In the use, the regulation of plant resistance to FHB may be manifested as a reduction in expression and/or activity of the TaCIPK14 protein and an increase in plant resistance to FHB in the plant.

Herein, the reduction in expression and/or activity of the TaCIPK14 protein is preferably a simultaneous reduction in expression and/or activity of the TaCIPK14-4A protein, the TaCIPK14-4B protein and the TaCIPK14-4D protein, if the TaCIPK14 gene is knocked out or knocked down simultaneously on the wheat A genome, B genome and D genome.

In a second aspect, the present disclosure is drawn to use of a substance capable of causing a reduction in expression and/or activity of the TaCIPK14 protein in a plant in any one of the following:

(D1) Improvement of plant resistance to FHB; and (D2) Breeding plant varieties with improved resistance to FHB.

The TaCIPK14 protein is selected from the group consisting of the TaCIPK14-4A protein, the TaCIPK14-4B protein, and/or the TaCIPK14-4D protein, as previously described.

In some embodiments, the substance may be an RNA interference fragment, an RNA interference vector, a homologous recombinant fragment, a homologous recombinant vector, or a gene editing tool capable of causing a decrease in the expression and/or activity of the TaCIPK14 protein in the plant.

In a specific embodiment of the present disclosure, the substance is a CRISPR/CRISPR-associated protein 9 (Cas9) system, where the target sequence of the gRNA includes SEQ ID NO: 7 (gRNA1) and/or SEQ ID NO: 8 (gRNA2). Expression cassettes for gRNA1 and gRNA2 were constructed in tandem by digestion and ligation into a gene editing vector VK006 to produce a specific recombinant plasmid VK005-06-g1g2. The specific recombinant plasmid VK005-06-g1g2 contains a gene coding for a Cas9 protein and genes coding for the gRNA1 and the gRNA2.

In a third aspect, the present disclosure is drawn to a method for increasing plant resistance to FHB.

The method for increasing plant resistance to FHB in the present disclosure includes causing a decrease in expression and/or activity of the TaCIPK14 protein in a recipient plant.

The TaCIPK14 protein includes the TaCIPK14-4A protein, the TaCIPK14-4B protein, and the TaCIPK14-4D protein, as previously described.

In a fourth aspect, the present disclosure is drawn to a method for breeding plant varieties with improved resistance to FHB.

The method for breeding plant varieties with improved resistance to FHB in the present disclosure includes causing a reduction in expression and/or activity of the TaCIPK14 protein in the recipient plant.

The TaCIPK14 protein includes the TaCIPK14-4A protein, the TaCIPK14-4B protein, and the TaCIPK14-4D protein, as previously described.

The methods in the third and fourth aspects may be achieved by hybridization or by genetic modification.

In the third and fourth aspects, causing a reduction in expression and/or activity of the TaCIPK14 protein in a recipient plant can be achieved by methods known in the art, such as RNA interference, homologous recombination, genome targeted editing, and the like.

In some embodiments, this can be achieved specifically by inhibiting expression of TaCIPK14.

In some embodiments, this can be achieved specifically by knocking out TaCIPK14, the knocking out including knocking out entire or a partial fragment of TaCIPK14.

In some embodiments, this can be achieved specifically by silencing TaCIPK14.

In some embodiments, this can be achieved specifically by gene editing of TaCIPK14.

In specific embodiments of the present disclosure, the gene editing is realized with the aid of a CRISPR/Cas9 system. In the CRISPR/Cas9 system, the guide RNA (gRNA) comprises gRNA1 and gRNA2, and the target sequences of gRNA1 and gRNA2 are shown in SEQ ID NO: 7 and SEQ ID NO: 8, respectively. The gene editing is achieved by introducing into the recipient plant (e.g., wheat) a specific DNA molecule containing the gene encoding the Cas9 protein and the gene encoding the gRNA. The gene editing is achieved by introducing a recombinant plasmid containing the specific DNA molecule in the recipient plant (e.g., wheat).

In a fifth aspect, the present disclosure claims a method for breeding a transgenic plant with improved resistance to FHB.

The method for breeding a transgenic plant with improved resistance to FHB in the present disclosure may include the steps of: inhibiting expression of a nucleic acid molecule capable of expressing the TaCIPK14 protein in a recipient plant, and obtaining a transgenic plant with improved resistance to FHB.

The TaCIPK14 protein includes the TaCIPK14-4A protein as previously described, the TaCIPK14-4B protein as previously described, and/or the TaCIPK14-4D protein as previously described.

In the method, it is understood that the transgenic plant include not only a first and a second generation of the transgenic plant, but also their offspring. In the case of the transgenic plant, the gene can be propagated in the species, or it can be transferred into other varieties of the same species, including in particular commercial varieties, using conventional breeding techniques. The transgenic plant includes seeds, healing tissues, complete plants and cells.

In some embodiments, inhibition of expression of a nucleic acid molecule capable of expressing the TaCIPK14 protein in the recipient plant may be achieved by introducing an RNA interference fragment, a RNA interference vector, a homologous recombinant fragment, a homologous recombinant vector, or a gene editing tool, etc., into the recipient plant.

In a specific embodiment of the present disclosure, the gene editing tool is a CRISPR/Cas9 system, where the target sequences of the gRNA include SEQ ID NO: 7 (gRNA1) and/or SEQ ID NO: 8 (gRNA2). The expression cassettes for gRNA1 and gRNA2 were constructed in tandem by enzymatic ligation into gene editing vector VK006 to generate a recombinant plasmid VK005-06-g1g2. The specific recombinant plasmid VK005-06-g1g2 contains a gene encoding Cas9 protein and genes encoding the gRNA1 and the gRNA2.

In the method, after attainment of the transgenic plant by inhibiting expression of a nucleic acid molecule capable of expressing the TaCIPK14 protein in the recipient plant, the method may further include a step of screening for a gene-edited plant from the transgenic plant, the gene-edited plant having higher resistance to FHB than the recipient plant.

In the method, after attainment of the transgenic plant by inhibiting expression of a nucleic acid molecule capable of expressing the TaCIPK14 protein in the recipient plant, the method may further include steps of self-crossing the transgenic plant, obtaining self-crossed progeny, and screening a gene-edited plant from the self-crossed progeny, the gene-edited plant having higher resistance to Fhb than the recipient plant.

Screening of the gene-edited plant may specifically include screening of a transgenic plant in which gene editing occurs and TaCIPK14 expression is simultaneously suppressed on the A, B and D genomes. If the TaCIPK14 gene is not edited on the A, B and D genomes at the same time, the method further include steps of: crossing the plant (e.g., wheat) in which editing of the TaCIPK14 gene occurs on the A, B or D genomes, self-crossing the progeny of a crossed plant, and screening for a transgenic plant (e.g., wheat) in which TaCIPK14 is edited in A, B and D genomes simultaneously and the expression of TaCIPK14 is suppressed.

Self-crossing the transgenic plant (e.g., wheat) may specifically include self-crossing a transgenic plant (e.g., wheat) in which gene editing occurs and TaCIPK14 expression is suppressed. Screening the gene-edited plant (e.g. wheat) from the self-cross progeny may specifically include screening the transgenic plant (e.g. wheat) from the self-cross progeny in which gene editing occurs and TaCIPK14 expression is suppressed.

The gene-edited plant (e.g., wheat) is a plant (e.g., wheat) that satisfies the following conditions: the A genome, the B genome, and the D genome are all mutated in the target region and are all homozygous.

The gene-edited plant (e.g., wheat) is a plant (e.g., wheat) that satisfies the following conditions: the A genome, the B genome, and the D genome are all mutated in the target region, are all homozygous, and does not carry a vector sequence.

The progeny obtained by self-crossing homozygous mutant plants in which all three copies of the TaCIPK14 gene in the A, B, and D genomes of a plant (e.g., wheat) are knocked out at the same time are known as gene-edited plants.

In all of the above aspects, the nucleic acid molecule capable of expressing the TaCIPK14 protein may be nucleic acid molecule A, nucleic acid molecule B, and/or nucleic acid molecule C.

The nucleic acid molecule A is capable of expressing the TaCIPK14-4A protein; the nucleic acid molecule B is capable of expressing the TaCIPK14-4B protein; and the nucleic acid molecule C is capable of expressing the TaCIPK14-4D protein.

The nucleic acid molecule A may be any of the following:
(a1) A DNA molecule set forth in SEQ ID NO: 1;
(a2) A DNA molecule hybridized with the DNA molecule defined in (a1) under stringent conditions and encoding the TaCIPK14-4A protein;
(a3) A DNA molecule having at least 99%, at least 95%, at least 90%, at least 85%, or at least 80% identity to any of the DNA sequences defined in (a1)-(a2) and encoding the TaCIPK14-4A protein;
The nucleic acid molecule B may be any of the following:
(b1) A DNA molecule set forth in SEQ ID NO: 2;
(b2) A DNA molecule hybridized with the DNA molecule defined in (b1) under stringent conditions and encoding the TaCIPK14-4B protein;
(b3) A DNA molecule having at least 99%, at least 95%, at least 90%, at least 85%, or at least 80% homology to any of the DNA sequences defined in (b1)-(b2) and encoding the TaCIPK14-4B protein;
The nucleic acid molecule C may be any of the following:
(c1) A DNA molecule set forth in SEQ ID NO: 3;
(c2) A DNA molecule hybridized with the DNA molecule defined in (c1) under stringent conditions and encoding the TaCIPK14-4D protein;
(c3) A DNA molecule having at least 99%, at least 95%, at least 90%, at least 85%, or at least 80% homology to any of the DNA sequences defined in (c1)-(c2) and encoding the TaCIPK14-4D protein.
For the above nucleic acid molecules, the stringent conditions may be as follows: 50° C., hybridized in a mixture of 7% sodium dodecyl sulfate (SDS), 0.5M $Na_3PO_4$ and 1 mM EDTA, rinsed at 50° C., 2×SSC, 0.1% SDS; and may also be: 50° C., hybridized in a mixture of 7% SDS, 0.5M $Na_3PO_4$ and 1 mM EDTA, rinsed at 50° C. 1×SSC, 0.1% SDS; or: 50° C., hybridized in a mixture of 7% SDS, 0.5M $Na_3PO_4$ and 1 mM EDTA, rinsed at 50° C., 0.5×SSC, 0.1% SDS; or: 50° C., hybridized in a mixture of 7% SDS, 0.5M $Na_3PO_4$ and 1 mM EDTA, rinsed at 50° C., 0.1×SSC, 0.1% SDS; or: 50° C., hybridized in a mixture of 7% SDS, 0.1×SSC, 0.1% SDS; also available as: hybridized at 50° C. in a mixture of 7% SDS, 0.5M $Na_3PO_4$ and 1 mM EDTA, rinsed at 65° C. in 0.1×SSC, 0.1% SDS; also available as: hybridized at 65° C. in a solution of 6×SSC, 0.5% SDS, followed by 2×SSC, 0.1% SDS and 1×SSC, 0.1% SDS each to wash the membrane once.

In the above description of nucleic acid molecules, the term 'identity' refers to the identity of the amino acid sequence. Identity of amino acid sequences can be determined using alignment search tools on the internet, such as BLAST of the NCBI homepage website. For example, this can be done in Advanced BLAST 2.1 by using blastp as program, with an Expect value being 10, all Filters being OFF, BLOSUM62 as Matrix, and Gap existence cost, Per residue gap cost and Lambda ratio set to 11, 1 and 0.85 (default values), respectively, and performing search to calculate the identity of a pair of amino acid sequences, so that the identity (%) is obtained.

In the above description of nucleic acid molecules, 'at least 95% identity' may be at least 96%, 97%, 98% identity. 'At least 90% identity' may be at least 91%, 92%, 93%, 94% identity. 'At least 85% identity' may be at least 86%, 87%, 88%, 89% identity. 'At least 80% identity' may be at least 81%, 82%, 83%, or 84% identity.

In all of the above aspects, the plant may be a monocotyledonous plant or a dicotyledonous plant.

In some embodiments, the monocotyledon may be a graminaceous plant.

In some other embodiments, the graminaceous plant may be a plant of genus *Triticum*.

More specifically, the plant of genus *Triticum* may be *Triticum aestivum*.

The varieties of *Triticum aestivum* may specifically be Fielder, Jimai 22, Zhengmai 7698, Xinong 979, Bainong 207, Xinmai 26 and the like. The wheat described in the present disclosure is not limited to the above mentioned varieties.

In all of the foregoing aspects, the pathogen of the FHB may be *Fusarium graminearum*.

In a specific embodiment of the present disclosure, the pathogen of the FHB is the wild-type strain of *F. graminearum* PH-1.

In a sixth aspect, the present disclosure claims a transgenic plant with improved resistance to FHB obtained by the method in the fifth aspect hereinbefore.

In particular, the transgenic plant may be a genetically modified plant, seed or tissue, etc.

BRIEF DESCRIPTION OF THE DRAWINGS

FIGS. 1A-1C shows a schematic diagram of the cDNA sequence alignment analysis of three copies of TaCIPK14 (SEQ ID NO: 1-3) provided in an example of the present disclosure.

FIG. 2 shows a schematic diagram of a protein sequence alignment analysis of three copies of TaCIPK14 (SEQ ID NOs: 4-6) provided in an example of the present disclosure, where * indicates the kinase catalyzation domain and arrows indicate the activation loop.

Figure 5C:
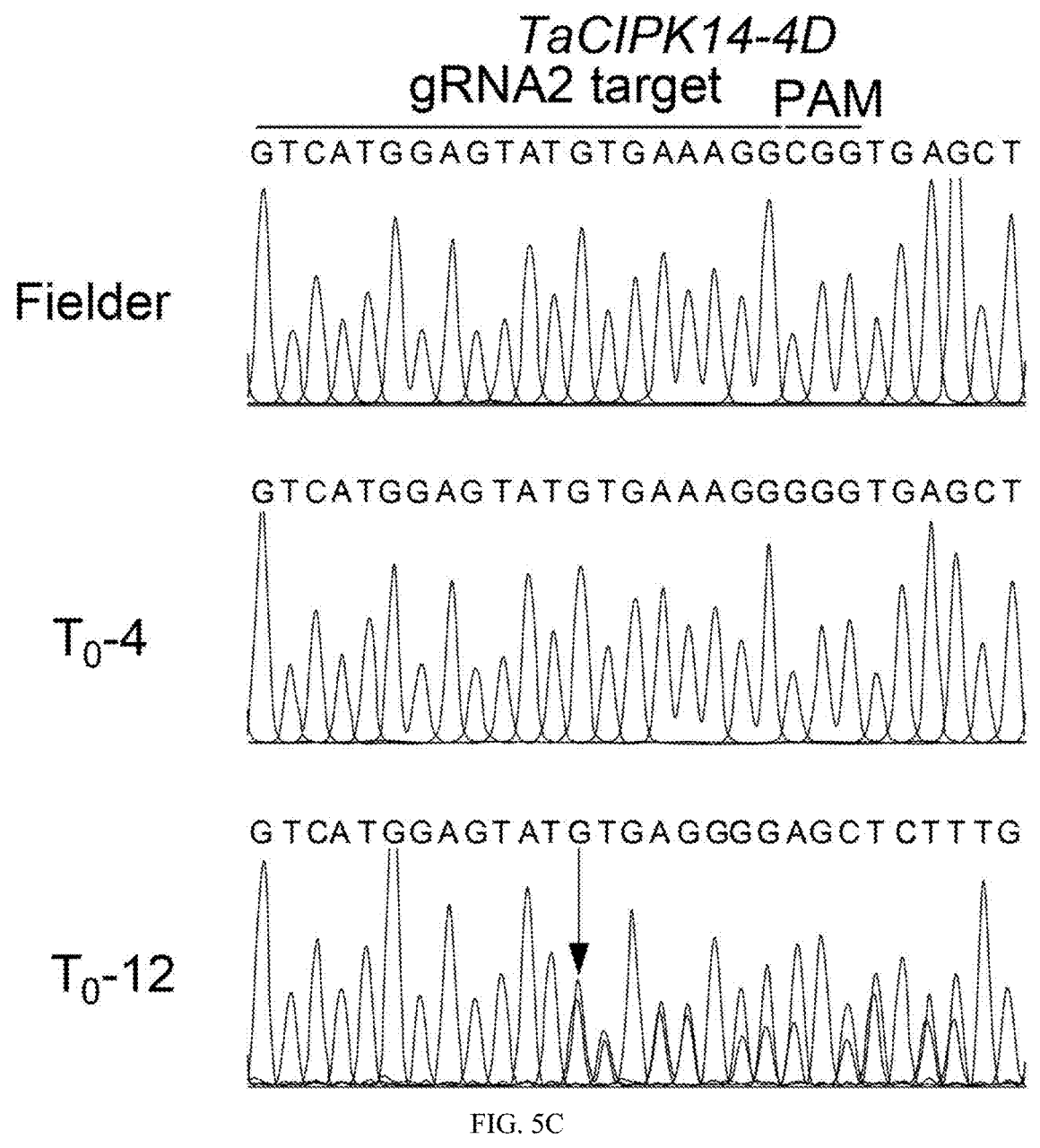

FIGS. 5A-5F show schematic diagrams of the results of sequencing analysis of TaCIPK14 To transgenic plants provided in an example of the present disclosure, where FIG. 5A-5C are schematic diagrams of the results of TaCIPK14 To transgenic plants $T_0$-4 and $T_0$-12 (SEQ ID NOS: 37-45) where editing occurs at the target sequence gRNA2; and FIGS. 5D-5F are schematic diagrams of the results of TaCIPK14 To transgenic plant $T_0$-21 (SEQ ID NOs: 46-51) where editing occurs at the target sequence gRNA1.

FIG. 6 shows a nucleotide alignment between the homzygous mutant with three copies of TaCIPK14 knocked out simultaneously in the wheat A, B, and D genomes and wild-type (SEQ ID NOs: 52-101) in an example of the present disclosure, where//indicates omissions.

FIG. 7 shows the deduced amino acid sequence alignment between the homozygous mutant with the three copies of TaCIPK14 knocked out simultaneously in the wheat A, B, and D genomes and the wild-type (SEQ ID NOs: 102-134) in an example of the present disclosure, where // indicates omissions, and * indicates termination.

FIG. 8A shows the incidence of wild-type plants and TaCIPK14 gene-edited plants after infection with FHB pathogens; and FIG. 8B shows the statistical analysis of the number of diseased spikelets in wild-type plants and TaCIPK14 gene-edited plants after FHB pathogen infestation.

DETAILED DESCRIPTION OF THE EMBODIMENTS

Figure 3:
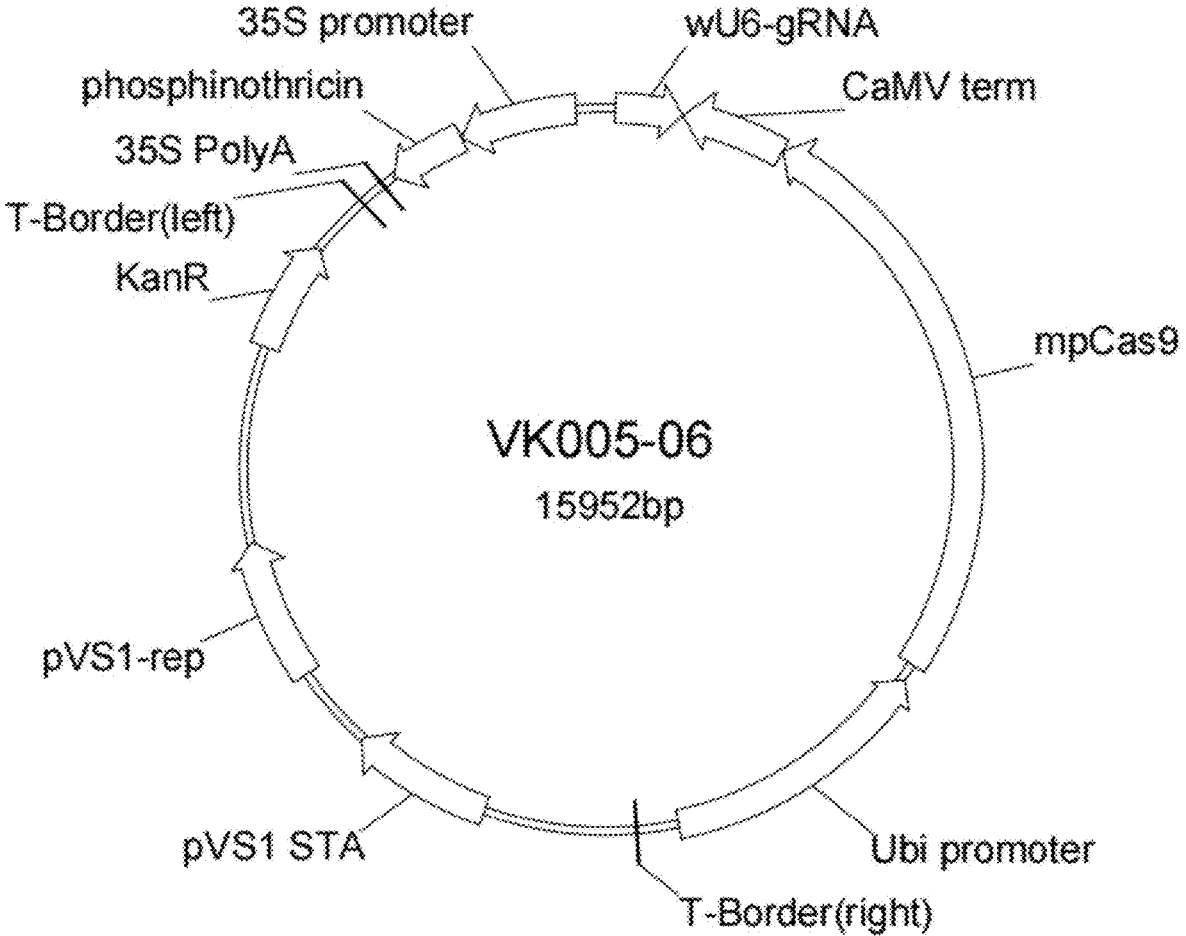
FIG. 3 shows a schematic diagram of editing vector VK005-06 for editing the wheat gene provided in an example of the present disclosure.

The following examples facilitate a better understanding of the disclosure, but do not limit the disclosure. The experimental methods in the following examples are conventional methods, if not otherwise specified. The test materials used in the following examples are, unless otherwise specified, purchased from a conventional biochemical reagent store. The quantitative tests in the following examples are set up for three repetitions, and the results are averaged.

The plant CRISPR/Cas9 gene editing vector is VK005-06, which is a product from Beijing Viewsolid Biotech Co., Ltd. and contains the wheat U6 promoter TaU6 for initiating small guide RNA (sgRNA), Cas9p mimics the graminaceous plant genes with higher GC content at the 5' end, and is a designed and synthesized gene with optimized codons for plants. The primers used in this disclosure were synthesized by Xi'an Tsingke Zexi Biotechnology Co. Ltd.

For the quantitative tests in the following examples, three replicate experiments are set up and the results are averaged.

Wheat variety Fielder (referred to as "Fielder" in the literature): Bai X, Zhan G, Tian S, et al. Transcription factor BZR2 activates chitinase Cht20. 2 transcription to confer resistance to wheat stripe rust [J]. Plant Physiology, 2021, 187 (4): 2749-2762. Fielder is assigned as WT, and the corresponding sequence in the A genome is assigned as WT-A, the corresponding sequence in the B genome is assigned as WT-B, and the corresponding sequence in the D genome is assigned as WT-D.

Example 1: Preparation of Recombinant Plasmids

The genomic sequences and coding sequences of the TaCIPK14 gene on chromosomes A, B, and D were amplified from the DNA and cDNA of the wheat variety Fielder. The nucleotide sequence of TaCIPK14 in the A genome was denoted by TaCIPK14-4A, and the nucleotide sequence of TaCIPK14 in the B genome was denoted by TaCIPK14-4B. The nucleotide sequence of TaCIPK14 in D genome was denoted by TaCIPK14-4D. The amplification results showed that the TaCIPK14 gene was 1335 bases in length and did not contain introns. In the wheat Fielder genome, the nucleotide sequence of the TaCIPK14 gene in the A genome (corresponding to the A chromosome group) is set forth in SEQ ID NO: 1 of the sequence listing (encoding the protein of SEO ID NO: 4), which is 100% identical to that in the Ensembl Plants database (plants.ensembl.org/index.html); the nucleotide sequence of the TaCIPK14 gene in the B genome (corresponding to the B chromosome group) is set forth in SEQ ID NO: 2 of the sequence listing (encoding the protein of SEQ ID NO: 5), which is 100% identical to that of wheat in the Ensembl Plants database; the nucleotide sequence of the TaCIPK14 gene in the B genome (corresponding to the B chromosome group) is set forth in SEQ ID NO: 3 of the sequence listing (encoding the protein of SEQ ID NO: 6), which is 100% identical to that of wheat in the Ensembl Plants database. The schematic diagram of the sequence alignment analysis of the cDNA sequences of the three copies of TaCIPK14 is shown in FIGS. 1A-1C. The schematic diagram of the protein sequence alignment analysis of the three copies of TaCIPK14 is shown in FIG. 2.

Through the website E-CRISPR (www.e-crisp.org/), common guide RNA (gRNA) sequences the TaCIPK14 gene on A, B and D genomes were found, and the 20 bp sequences in front of the Protospacer Adjacent Motif (PAM) were set as gRNA sequences. In the present Example, two of the sgRNAs were taken for the knockdown experiments as an example, the sequences were gRNA1:5'-GGCGTGAGGT-CACAACCATG-3' (SEQ ID NO: 7) and gRNA2:5'-GT-CATGGAGTATGTGAAA GG-3' (SEQ ID NO: 8).

VK005-6-gRNA1 recombinant plasmid and VK005-6-gRNA2 recombinant plasmid were constructed according to the instructions of the Plant Cas9/gRNA Plasmid Construction Kit (Beijing Viewsolid Biotech Co. Ltd.). The schematic diagram of gene editing vector VK005-06 is shown in FIG. 3. The structure of VK005-6-gRNA1 recombinant plasmid is described as a recombinant plasmid obtained by replacing positions 392-411 of the VK005-06 vector with the DNA fragment of SEQ ID NO: 7. The structure of VK005-6-gRNA2 recombinant plasmid is described as the recombinant plasmid obtained by replacing positions 392-411 of the VK005-06 vector with the DNA fragment of SEQ ID NO: 8.

The gRNA1 and gRNA2 were tandemly ligated together to construct a recombinant plasmid VK005-06-g1g2, and the specific steps included the followings. The recombinant plasmid VK005-6-gRNA1 was double-digested with AscI and SpeI, and a short band (wU6:510 bp) was recovered by running gels, which was ligated into the vector of recombinant plasmid VK005-6-gRNA2 double-digested with AscI and AvrII. The ligated product was transformed into *Escher-*

*ich coli*, and then cultured on LB (kan) plates until the clone grew. Then a single clone was picked for sequencing with the sequencing primer:

VK005-6-R: 5'-GATGAAGTGGACG-GAAGGAAGGAG-3' (SEQ ID NO: 9).

Figure 4:
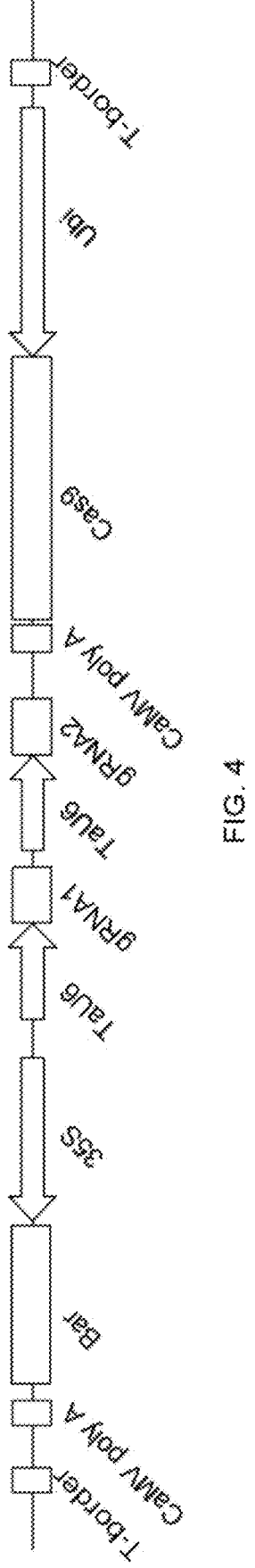
FIG. 4 shows a schematic diagram of the editing vector VK005-06-g1g2 for editing the wheat gene TaCIPK14 provided in an example of the present disclosure.
Figure 5B:
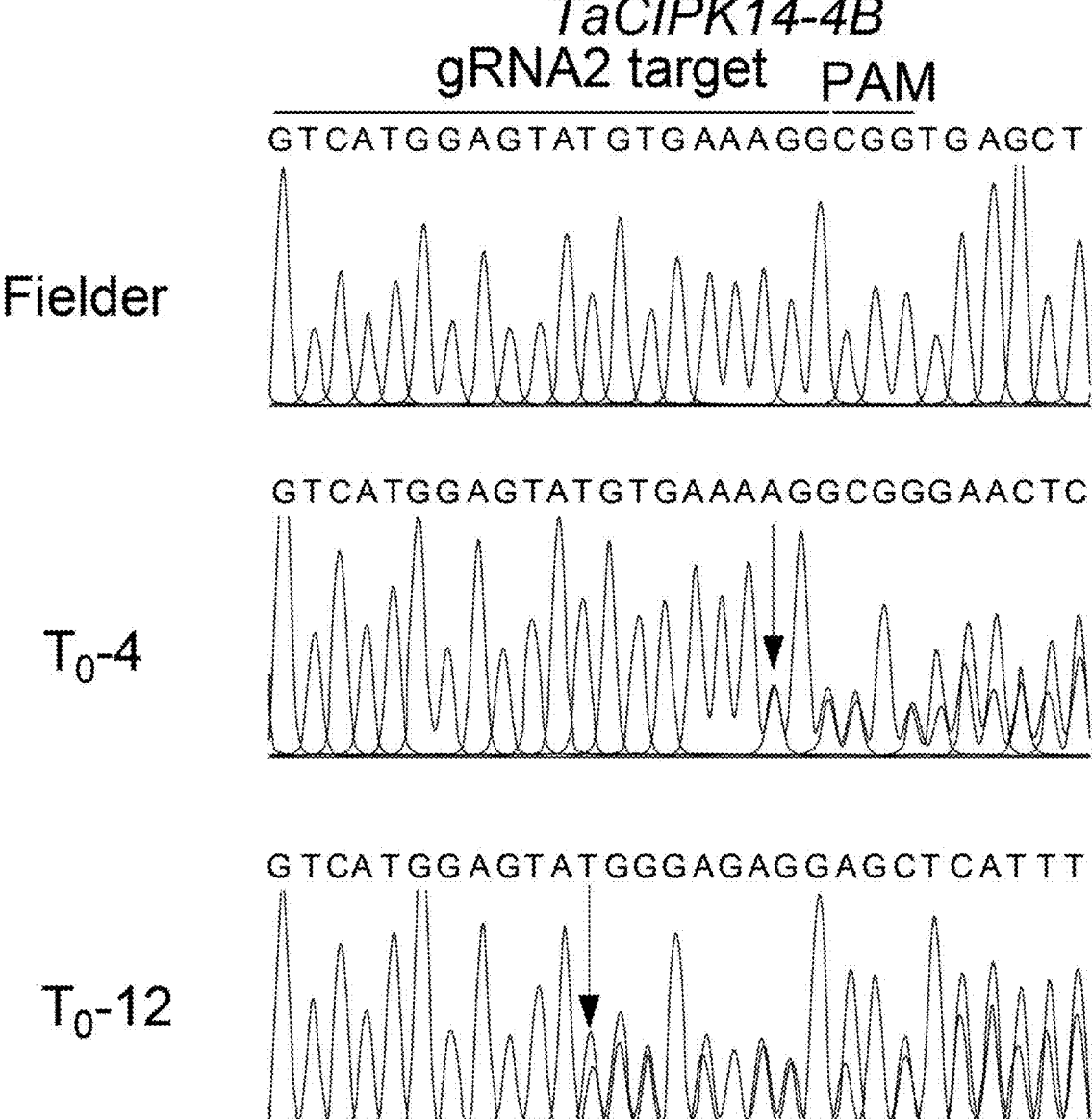

The sequencing results showed that the target sequences of sgRNA, gRNA1 and gRNA2 were detected, and TaU6 promoter sequences were all detected upstream of the target sequences. The sequencing results indicated that the sgRNA expression cassette was successfully constructed and assembled into the VK005-06 binary expression vector, which proved the successful construction of the CRISPR/Cas9 gene editing vector for TaCIPK14. The schematic diagram of the editing vector VK005-06-g1g2 for editing wheat TaCIPK14 gene is shown in FIG. 4.

The structure of the VK005-06-g1g2 vector is described as a recombinant plasmid obtained by replacing positions 392-411 of the VK005-06 vector with the DNA fragment of SEQ ID NO: 7, and replacing positions 864-883 of the VK005-06 vector with the DNA fragment of SEQ ID NO: 8 meanwhile.

Example 2: Obtaining Gene-Edited Wheat by *Agrobacterium*-Mediated Genetic Transformation Using Grna1 and Grna2

I. *Agrobacterium*-Mediated Genetic Transformation of Wheat

The gene editing recombinant plasmid VK005-06-g1g2 constructed in Example 1 was used to transform immature young embryos of the wheat variety Fielder by *Agrobacterium*-mediated genetic transformation, followed by differentiation, screening, regeneration, and rooting, and ultimately regenerated plants were obtained. Wheat genetic transformation was accomplished by the Genetic Transformation Platform of the State Key Laboratory of Crop Stress Biology for Arid Areas, Northwest Agriculture and Forestry University (NWAFSU), which can be commercially available to the public for the transformation operation.

II. Detection of Gene Editing

1. Identification of Regenerated Plants of to Generation

The test plants were: 22 To generation regenerated plants obtained in step I, and Fielder (as a reference plant for the regenerated plants). Genomic DNA was extracted from the leaves of the test plants and amplified by PCR using three specific primer pairs. The three specific primer pairs were: primer pairs consisting of TaCIPK14-A-F and TaCIPK14-A-R (the target sequences of the primer pairs in the wheat genomic DNA are set forth in SEQ ID NO: 1, where the gRNA1 and gRNA2 of the TaCIPK14 gene are located in the wheat A genome), TaCIPK14-B-F and TaCIPK14-B-R consisting of primer pairs (the target sequences of the primer pairs in wheat genomic DNA are set forth in SEQ ID NO: 2, in which gRNA1 and gRNA2 of the TaCIPK14 gene are located in the wheat B genome), TaCIPK14-D-F and TaCIPK14-D-R (the target sequences of the primer pairs in wheat genomic DNA are set forth in SEQ ID NO: 3, where gRNA1 and gRNA2 of the TaCIPK14 gene are located in the wheat D genome). The sequences of the three specific primer pairs are:

```
TaCIPK14-A-F:
                                  (SEQ ID NO: 10)
5'-GATTGTTGGGGAAAGGAACATTT-3';

TaCIPK14-A-R:
                                  (SEQ ID NO: 11)
5'-TTGTCTCCTTTCTGCACTCCTCTC-3';
```

-continued

```
TaCIPK14-B-F:
                                  (SEQ ID NO: 12)
5'-CGCAGTCCATTTGAATTATAGCCA-3';

TaCIPK14-B-R:
                                  (SEQ ID NO: 13)
5'-ATTCAGCGCCTTTGCAACG-3';

TaCIPK14-D-F:
                                  (SEQ ID NO: 14)
5'-AAGACATGAGAGTGTTGTTCACTGTG-3';

TaCIPK14-D-R:
                                  (SEQ ID NO: 15)
5'-AGCTGTAGGAGGAGCATTTGTGA-3'.
```

2. Sequencing of the Recovered PCR Amplification Products after Step 1.

The amplification products were purified and subjected to first-generation sequencing (Sanger sequencing), and the sequencing results were compared with the A, B, and D genomic sequences of the TaCIPK14 gene in Fielder. If sequence alignment shows double peaks at the target site, it is indicated heterozygous or bi-allelic mutations occurs at the target site, if there are base deletions or insertions at the target site, it is indicated homozygous mutations occurs at the target site, and if the nucleotide sequences of the target site is consistent with that of the PCR amplification products of Fielder, the regenerated plants are wild-type. The PCR products with mutations were ligated into T-Simple vector and transformed into *E. coli*, and the positive clones obtained were sequenced by colony PCR amplification using universal primers to clarify the mutation mode of TaCIPK14.

If the PCR amplification product of the regenerated plant is only one and the nucleotide sequence is consistent with that of the PCR amplification product of Fielder, the regenerated plant is wild-type. If the PCR amplification product of the regenerated plant is of two kinds, one of which is consistent with the nucleotide sequence of the PCR amplification product of Fielder, and the other of which has a mutation (the mutation includes a deletion, insertion, or substitution of one or more nucleotides) compared to the nucleotide sequence of the PCR amplification product of Fielder, the regenerated plant is heterozygous. If the PCR amplification product of the regenerated plant is of two kinds, both of which have mutations (the mutations include deletions, insertions or substitutions of one or more nucleotides) compared to the nucleotide sequence of the PCR amplification product of Fielder, the regenerated plant is bi-allelic mutant. If the PCR amplification product of the regenerated plant is of one kind and has a mutation (the mutation includes a deletion, insertion or substitution of one or more nucleotides) compared to the nucleotide sequence of the PCR amplification product of Fielder, the regenerated plant is a homozygous mutant. If the PCR amplification products of the regenerated plant are of three or more kinds, the regenerated plant is chimeric. Heterozygous, bi-allelic mutant, homozygous mutant, and chimeric plants were collectively referred to as edited plants. Of the 22 regenerated plants, 3 were edited plants (13.6%), and 19 were wild-type (86.4%). The results of the sequencing analysis of TaCIPK14 $T_0$ transgenic plants are shown schematically in FIGS. 5A-5F.

The genotypes of the three gene-edited strains based on the target sequence A, B, and D genomes, and the types of mutations based on the target sequences are shown in Table 1.

TABLE 1

| | Genotypes of $T_0$ gene edited strains | | |
|---|---|---|---|
| $T_0$ generation plant number | Genotypes based on target sequences | | Mutation types based on target sequences |
| $T_0$-4 | A | +1 | heterozygous mutant |
| | B | +1 | heterozygous mutant |
| | D | wt | wild type |
| $T_0$-12 | A | wt | wild type |
| | B | −5 | heterozygous mutant |
| | D | −1, −5 | chimeric mutant |
| $T_0$-21 | A | wt | wild type |
| | B | −89 | heterozygous mutant |
| | D | −11 | heterozygous mutant |

Note:
− stands for deletion, −5 stands for deletion of 5 nucleotides, and so on; + stands for insertion, +1 stands for insertion of 1 nucleotide, and so on.

The TaCIPK14 gene in one homologous chromosome in the A genome of $T_0$-4 was wild-type (SEQ ID NO: 1), and the TaCIPK14 gene in one homologous chromosome was the mutant gene obtained by inserting one base between nucleotides 276-277 (i.e., SEQ ID NO: 1 at positions 276-277) in the wild-type gene; The TaCIPK14 gene in one homologous chromosome in the B genome was wild-type (SEQ ID NO: 2), and the TaCIPK14 gene in one homologous chromosome was a mutant gene obtained by inserting one base between nucleotides 276-277 (i.e., positions 276-277 of SEQ ID NO: 2) in the wild-type gene; The TaCIPK14 gene in two homologous chromosomes in the D genome was wild-type (SEQ ID NO: 3). With the exception of wild type, all of the above mutant types of the gene resulted in a code-shifting mutation leading to a loss of function of the TaCIPK14 protein.

The TaCIPK14 gene in two homologous chromosomes in the A genome of $T_0$-12 was wild-type (SEQ ID NO: 1); the TaCIPK14 gene in one homologous chromosome in the B genome was wild-type (SEQ ID NO: 2) and in one homologous chromosome was a mutant gene obtained by deleting nucleotides at positions 272-276 (i.e., positions 272-276 of SEQ ID NO: 2) from the wild-type gene; the TaCIPK14 gene in the D genome was a chimeric mutation, in which one genotype was wild-type (SEQ ID NO: 3), one genotype was a mutation obtained by deleting the nucleotide at position 278 (i.e., position 278 of SEQ ID NO: 3) from the wild-type gene, and one genotype was a mutant gene obtained by deleting nucleotides at positions 274-278 (i.e., positions 274-278 of SEQ ID NO: 3) from the wild-type gene. With the exception of wild type, all of the above genotypes resulted in a code-shifting mutation leading to a loss of function of the TaCIPK14 protein.

The TaCIPK14 gene in two homologous chromosomes in the A genome of $T_0$-21 was wild-type (SEQ ID NO: 1); the TaCIPK14 gene in one homologous chromosome in the B genome was wild-type (SEQ ID NO: 2), and the TaCIPK14 gene in one homologous chromosome was a mutant gene obtained by deleting nucleotides at positions 190-278 (i.e., positions 190-278 of SEQ ID NO: 2) from the wild-type gene; the TaCIPK14 gene in one homologous chromosome in the D genome was wild-type (SEQ ID NO: 3), and in one homologous chromosome was a mutant gene obtained by deleting nucleotides at positions 184-194 (i.e., positions 184-194 of SEQ ID NO: 3) from the wild-type gene; With the exception of wild type, all of the above mutant types of the gene resulted in a code-shifting mutation leading to a loss of function of the TaCIPK14 protein.

2. Characterization of $T_1$ Generation Plants

To generation plants were taken for self-crossing to obtain $T_1$ generation seeds, and the $T_1$ generation seeds were cultivated to obtain $T_1$ generation plants.

Individual $T_1$ generation plants were characterized according to the method of step 1.

The results of each identification are shown in Table 2.

TABLE 2

| | Genetic profile of $T_1$ generation plants | | | | |
|---|---|---|---|---|---|
| | number of plants | | Number of wild-type plants | Number of heterozygous mutant plants | Number of homozygous mutant plants |
| $T_1$ generation plants from $T_0$ generation plant $T_0$-4 | 21 | A | 4 | 10 | 7 |
| | | B | 6 | 10 | 5 |
| | | D | 21 | 0 | 0 |
| $T_1$ generation plants from $T_0$ generation plant $T_0$-12 | 14 | A | 14 | 0 | 0 |
| | | B | 4 | 5 | 5 |
| | | D | 0 | 8 | 6 |
| $T_1$ generation plants from $T_0$ generation plant $T_0$-21 | 36 | A | 36 | 0 | 0 |
| | | B | 11 | 19 | 6 |
| | | D | 6 | 22 | 8 |

It was shown that the D genome of $T_0$-4, the A genome of $T_0$-12, and the A genome of $T_0$-21 of the unedited TaCIPK14 were stably inherited to $T_1$, and did not produce mutations; for the edited heterozygous mutant of TaCIPK14, segregation in $T_1$ obtained by strict self-crossing was in accordance with Mendelian inheritance; for the edited chimeric mutant of TaCIPK14, segregation in $T_1$ obtained by strict self-crossing did not conform to Mendelian inheritance.

$T_1$ generation plants that are of the mutation type 'A genome homozygous mutant, B genome homozygous mutant and D genome wild type' based on target sequence were selected from the $T_1$ generation plants of the $T_0$ generation plant $T_0$-4, $T_1$ generation plants that are of the mutation type 'A genome wild type, B genome homozygous mutant and D genome homozygous mutant' based on target sequence were selected from the $T_1$ generation plants of the $T_0$ generation plant $T_0$-12, and $T_1$ generation plants that are of the mutation type 'A genome wild type, B genome homozygous mutant and D genome homozygous mutant' based on target sequence were selected from the $T_1$ generation plants of the $T_0$ generation plant $T_0$-21. The selected $T_1$ generation plants were self-crossed and the resultant seeds were harvested. $T_2$ generation seeds were cultivated to obtain $T_2$ generation plants.

Figure 6:
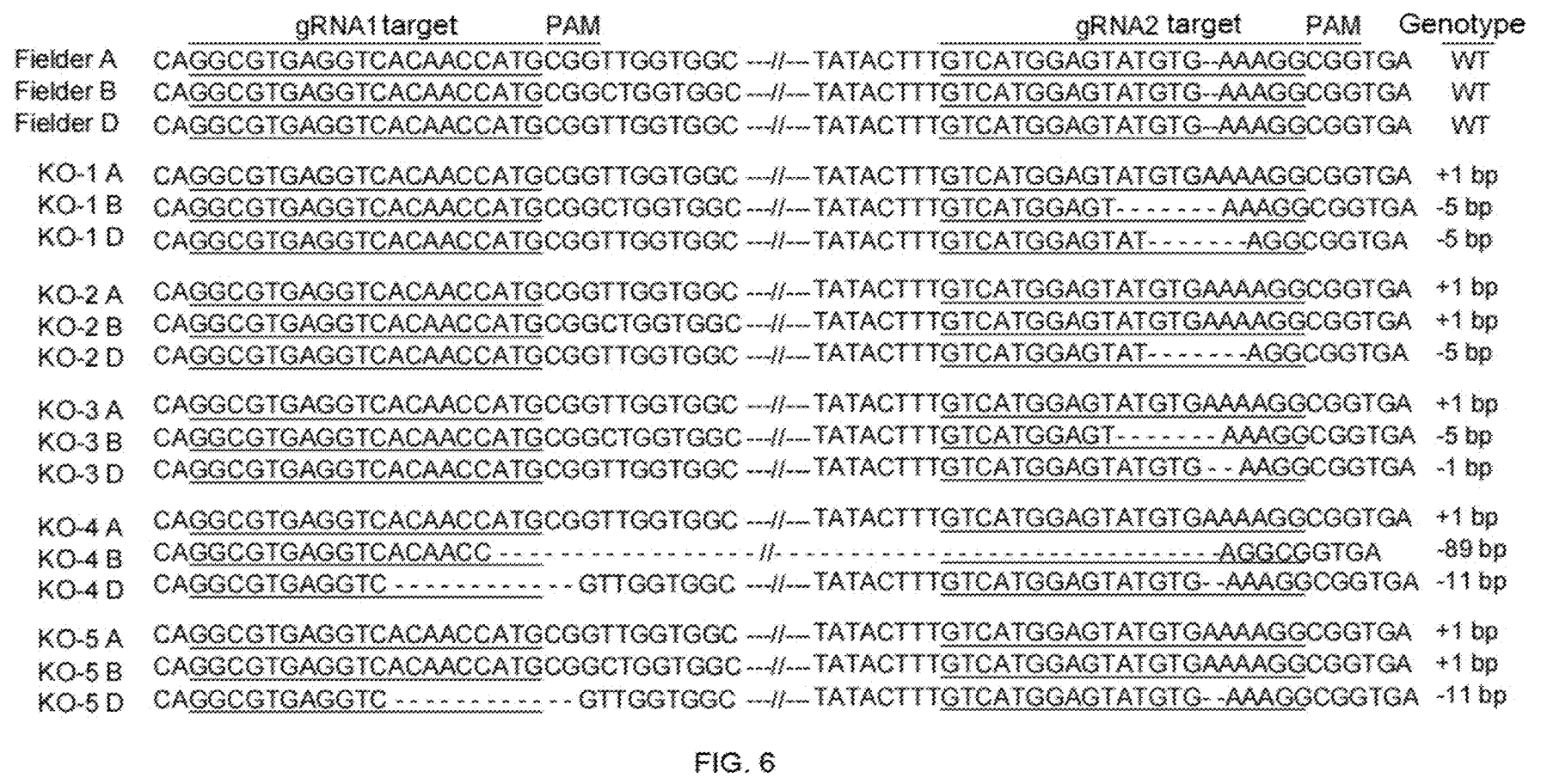

3. Creation of a Homozygous Mutant Strain with Simultaneous Knockout of Three Copies of TaCIPK14 in the A, B and D Genomes of Wheat In order to obtain homozygous mutant strains with three copies of TaCIPK14 knocked out simultaneously in the A, B and D genomes of wheat, $T_2$ generation plants that are of the mutation type 'A genome homozygous mutant, B genome homozygous mutant and D genome wild type' based on the target sequence were selected as the male parent, and $T_2$ generation plants that are of the mutation type 'A genome wild type, B genome homozygous mutant and D genome homozygous mutant' based on the target sequence were selected as the female parent. The selected $T_2$ generation plants were crossed to obtain $F_1$ plants. Each $F_1$ plant was characterized according to the method in step 1. $F_1$ plants with a target sequence-based mutation type 'A genome heterozygous mutant, B genome heterozygous mutant and D genome heterozygous mutant' were selected for self-crossing to obtain $F_2$ plants. Each of the $F_2$ plants was characterized according to the method in step 1. The $F_2$ plants with the mutation type 'A genome-homozygous mutant, B genome-homozygous mutant and D genome-homozygous mutant' based on the target sequences were selected, and the selected $F_2$ plants were self-crossed to obtain $F_3$ plants, which were the homozygous mutant strain with all three copies of TaCIPK14 knocked out simultaneously in the wheat A, B, and D genomes. In the process of obtaining homozygous mutant strain with three copies of TaCIPK14 knocked out simultaneously in wheat A, B and D genomes, the genotypic identification results of each generation of plants are shown in Table 3. The nucleotide alignment between homozygous mutant and wild-type genes with three copies of TaCIPK14 knocked out simultaneously in wheat A, B and D genomes is shown in FIG. 6. The deduced amino acid sequences of the three copies of TaCIPK14 in the wheat A, B and D genomes were aligned with those of the wild-type gene as shown in FIG. 7, indicating that the knock out of the three copies of TaCIPK14 in the wheat A, B and D genomes in the homozygous mutant phenotype resulted in code-shifting mutation, which led to a loss of function of the TaCIPK14 protein. It was shown that the homozygous mutant strain with TaCIPK14 mutation in $T_2$ generation could be inherited to $F_1$ and $F_2$ generation plants by crossing, and for the strict self-crossing of TaCIPK14 heterozygous mutant strain in $F_1$ generation plants to obtain the homozygous mutant strain with simultaneous knockout of all three copies of TaCIPK14 in wheat A, B, and D genomes, the segregation conformed to Mendelian inheritance. Homozygous mutant strains with simultaneous knockout of three copies of TaCIPK14 in wheat A, B and D genomes, including KO-1, KO-2, KO-3, KO-4 and KO-5, were available at $F_2$ generation.

TABLE 3

Genetic profile of $T_2$, $F_1$, $F_2$ generation plants

| Number of plants | Plant number | Genotype based on target sequence | | Mutation types based on target sequence | Number of homozygous three-copy homozygous mutant plants |
|---|---|---|---|---|---|
| — | $T_2$-4-1 | A | +1 | Homozygous mutant | — |
| | | B | +1 | Homozygous mutant | |
| | | D | wt | Wild type | |
| | $T_2$-4-13 | A | +1 | Homozygous mutant | |
| | | B | +1 | Homozygous mutant | |
| | | D | wt | Wild type | |
| | $T_2$-4-1 | A | +1 | Homozygous mutant | |
| | | B | +1 | Homozygous mutant | |
| | | D | wt | Wild type | |
| | $T_2$-4-13 | A | +1 | Homozygous mutant | |
| | | B | +1 | Homozygous mutant | |
| | | D | wt | Wild type | |

| Number of plants | Female Parent plant number | Genotype based on target sequence | | Mutation type based on target sequence | Number of homozygous three-copy homozygous mutant plant |
|---|---|---|---|---|---|
| — | $T_2$-12-12 | A | wt | Wild type | — |
| | | B | −5 | Homozygous mutant | |
| | | D | −5 | Heterozygous mutant | |
| | $T_2$-12-1 | A | wt | Wild type | |
| | | B | −5 | Homozygous mutant | |
| | | D | −1 | Homozygous mutant | |
| | $T_2$-21-1 | A | wt | Wild type | |
| | | B | −89 | Homozygous mutant | |
| | | D | −11 | Homozygous mutant | |
| | $T_2$-21-2 | A | wt | Wild type | |
| | | B | −89 | Homozygous mutant | |
| | | D | −11 | Homozygous mutant | |

| Number of $F_1$ plant | | Mutation type based on target sequence | | |
|---|---|---|---|---|
| 10 | — | A | Heterozygous mutant | — |
| | | B | Heterozygous mutant | |
| | | D | Heterozygous mutant | |
| 10 | | A | Heterozygous mutant | |
| | | B | Heterozygous mutant | |
| | | D | Heterozygous mutant | |
| 8 | | A | Heterozygous mutant | |
| | | B | Heterozygous mutant | |
| | | D | Heterozygous mutant | |
| 9 | | A | Heterozygous mutant | |
| | | B | Heterozygous mutant | |
| | | D | Heterozygous mutant | |

TABLE 3-continued

| | | | | Genetic profile of $T_2$, $F_1$, $F_2$ generation plants | | |
|---|---|---|---|---|---|
| Number of $F_2$ plant | Homozygous three-copy homozygous mutant plant Number | Genotype based on target sequences | | Mutation type based on target sequence | Number of homozygous three-copy homozygous mutant plants |
| 81 | KO-1 | A | 1 | Homozygous mutant | 2 |
| | | B | −5 | Homozygous mutant | |
| | | D | −5 | Homozygous mutant | |
| | KO-2 | A | 1 | Homozygous mutant | 2 |
| | | B | 1 | Heterozygous mutant | |
| | | D | −5 | Heterozygous mutant | |
| 87 | KO-3 | A | 1 | Heterozygous mutant | 1 |
| | | B | −5 | Homozygous mutant | |
| | | D | −1 | Homozygous mutant | |
| 44 | KO-4 | A | 1 | Homozygous mutant | 1 |
| | | B | −89 | Homozygous mutant | |
| | | D | −11 | Homozygous mutant | |
| 69 | KO-5 | A | 1 | Homozygous mutant | 2 |
| | | B | 1 | Homozygous mutant | |
| | | D | −11 | Homozygous mutant | |

III. Off-Target Analysis of CRISPR/Cas9

The possible off-target sites of the sgRNA1 target of TaCIPK14 gene were predicted according to the prediction software CasOT (eendb.zfgenetics.org/casot/), and primers were designed based on the flanking sequences of the possible off-target sites: a primer pair consisting of g1off1-F and g1off1-R, a primer pair consisting of g1off2-F and g1off2-R, a primer pair consisting of g1off3-F and g1off3-R, and a primer pair consisting of g1off4-F and g1off4-R. The possible off-target sites of the sgRNA2 target of TaCIPK14 were also predicted according to the prediction software CasOT, and primers were designed according to the flanking sequences of the possible off-target sites: a primer pair consisting of g2off5-F and g2off5-R, a primer pair consisting of g2off6-F and g2off6-R, and a primer pair consisting of g2off7-F and g2off7-R.

```
g1off1-F:
                                    (SEQ ID NO: 16)
5'-CGGAGTTCGGGACCTCGGTG-3';

g1off1-R:
                                    (SEQ ID NO: 17)
5'-TCGCCTTCCTCCTCCTCCTGCC-3'.

g1off2-F:
                                    (SEQ ID NO: 18)
5'-ACCTCCTCCTCCTTCCTGTCGTCTT-3';

g1off2-R:
                                    (SEQ ID NO: 19)
5'-TACGGGGTTGCTGGCACTTG-3'.

g1off3-F:
                                    (SEQ ID NO: 20)
5'-CACGGAGACGCCCAGAGAC-3';

g1off3-R:
                                    (SEQ ID NO: 21)
5'-CGCACGGTAGGAGCAACGG-3'.

g1off4-F:
                                    (SEQ ID NO: 22)
5'-TATTTCCTCCATCTTGCTCTCTTCC-3';

g1off4-R:
                                    (SEQ ID NO: 23)
5'-CAAGTGTCTACTCTCTCCATCCACAA-3'.
```

```
                    -continued g2off5-F:
                                    (SEQ ID NO: 24)
5'-CGTGTGCCTGCTTTTTGCTG-3';

g2off5-R:
                                    (SEQ ID NO: 25)
5'-CGCCAGTGTTGATGTGAGATTGT-3'.

g2off6-F:
                                    (SEQ ID NO: 26)
5'-GGGGAGGATGTGGGCAGAT-3';

g2off6-R:
                                    (SEQ ID NO: 27)
5'-CGCAACGAGGACCAACACTTTA-3'.

g2off7-F:
                                    (SEQ ID NO: 28)
5'-CTCATCCATTTTTATCACAACCTTAGA-3';

g2off7-R:
                                    (SEQ ID NO: 29)
5'-GCTGACCGCCAGACCCACT-3'.
```

(1) $T_2$ generation of TaCIPK14 gene-edited plants ($T_2$-4-1, $T_2$-21-2, and $T_2$-12-12) and homozygous mutant $F_3$ plants (KO-1, KO-2, KO-3, KO-4, and KO-5) with three copies of TaCIPK14 knocked out at the same time in the wheat A, B, and D genomes were taken and their leaves were extracted for genomic DNA.

(2) With the genomic DNA extracted in step (1) as a template, the primer pair consisting of g1off1-F and g1off1-R, the primer pair consisting of g1off2-F and g1off2-R, the primer pair consisting of g1off3-F and g1off3-R, the primer pair consisting of g1off4-F and g1off4-R, the primer pair consisting of g2off5-F and g2off5-R, the primer pair consisting of g2off6-F and g2off6-R, and the primer pair consisting of g2off7-F and g2off7-R were used for PCR amplification.

(3) The PCR amplification product obtained in step (2) was sequenced.

Off-target sites are shown in Table 4.

TABLE 4

List of off-target sites

| gRNA targets | Off-target site | Location of off-target sites | Nucleotide sequence of off-target sites | Number of differential nucleotides compared to the target site |
|---|---|---|---|---|
| gRNA1 | OFF1 | chr2D: 139522328: 139524351 | aGCtcGAG_GTCACAACCAT G-GGG (SEQ ID NO: 30) | 3 |
| | OFF2 | chr3D: 156768495: 156770518 | aGCtaGAG_GTCACAACCAT G-GGG (SEQ ID NO: 31) | 3 |
| | OFF3 | chr5D: 534426169: 534428192 | aGCtcGAG_GTCACAACCAT G-GGG (SEQ ID NO: 32) | 3 |
| | OFF4 | chr7A: 176673733: 176675756 | cGaGTGAG_GTCgCAACCAT G-CGG (SEQ ID NO: 33) | 3 |
| gRNA2 | OFF5 | chr2B: 130489523: 130491546 | gGTTCTgT_CCTTCtCTGCAA- TGG (SEQ ID NO: 34) | 3 |
| | OFF6 | chr2B: 676945246: 676947269 | aaTTtTCT_CCTTCgCTGCAA- AGG (SEQ ID NO: 35) | 3 |
| | OFF7 | chr 6a: 42782254: 42784277 | tGcTCTCT_aCTTCACTGCAA- TGG (SEQ ID NO: 36) | 3 |

It was shown that for the seven predicted potential off-target sites mentioned above, no off-targets were detected in $T_2$ generation TaCIPK14 gene-edited plants ($T_2$-4-1, $T_2$-21-2, and $T_2$-12-12) and homozygous mutant $F_3$ plants (KO-1, KO-2, KO-3, KO-4, and KO-5) with simultaneous knockout of all three copies of TaCIPK14 in the wheat A, B, and D genomes. i.e., No off-target effects of gRNA1 and gRNA2 were detected at potential off-target sites.

Example 3: Analysis of Wheat FHB Resistance

The test plants were Fielder plants, and homozygous mutant strain with three copies of TaCIPK14 knocked out simultaneously in the wheat A, B, and D genomes, including KO-1, KO-4, and KO-5 prepared in Example 2.

The test plants were characterized for resistance to FHB in the following steps:

(1) *F. graminearum* wild-type strain PH-1, the causal agent of wheat FHB, was used for the culture of conidial spore, which was donated by Mr. Liu Huiquan from the College of Plant Protection, Northwest Agriculture and Forestry University, and was recorded in the paper "Li Yimin et al., Functional characterization of the HDACs genes in *Fusarium graminearum*. Northwest Agriculture and Forestry University, 2010, Master's Degree thesis", which is available to the public from the applicant, and may be used only for the purpose of repeating the experiments of the present disclosure, not for any other purpose. The strain was cultured and activated on PDA solid medium, and a piece of solid with FHB strain was taken from the above medium with a disc sampler, put into 200 mL of sterilized carboxymethyl cellulose (CMC) liquid medium, then cultured at 25° C. and 180 rpm for 4-5 days with oscillation, sampled for microscopic examination, and then filtered through gauze. The spore suspension was prepared, and the concentration was $1\times10^5$ spores/ml.

(2) Selection and preparation of plastic bags: transparent plastic bags with a size of 30 cm×40 cm×50 μm in length×width×thickness and plastic ties for bundling were purchased.

(3) FHB pathogen inoculation and bag moisturizing: during the wheat flowering, spore suspension prepared in step (1) were taken, 10 μL of which were dropped to the lower part of the spikelet base of the florets. At least 30 ears were inoculated for each strain, and the inoculation site of the glumes was marked with a marker. Inner side of the transparent plastic bags prepared in step (2) and pathogen-inoculated spikes were sprayed. The inoculated spikes were bagged with plastic bags, which were moderately tied at internode under the spike with plastic ties. The date of inoculation was marked on waterproof labels at inoculation row plot that was easy to observe, the moisturizing was conducted for 3 days, and then the moisturizing bag was removed.

(4) Observation, documentation and statistics: the number of diseased spikelets was surveyed and counted 21 days after inoculation, the resistance of test plants to FHB was evaluated as the average number of diseased spikelets, and the significance of differences was analyzed.

Figure 8A:
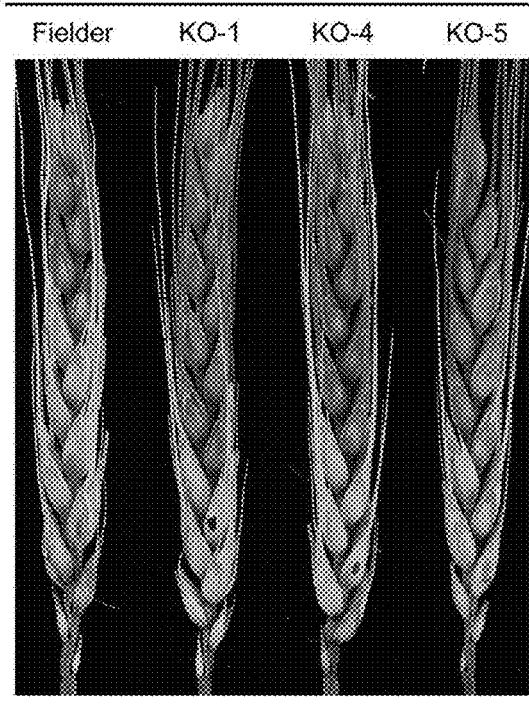
FIGS. 8A-8B show a schematic diagram of the TaCIPK14 gene-edited plant provided in an example of the present disclosure inoculated with FHB pathogens exhibiting resistance, where
Figure 8B:
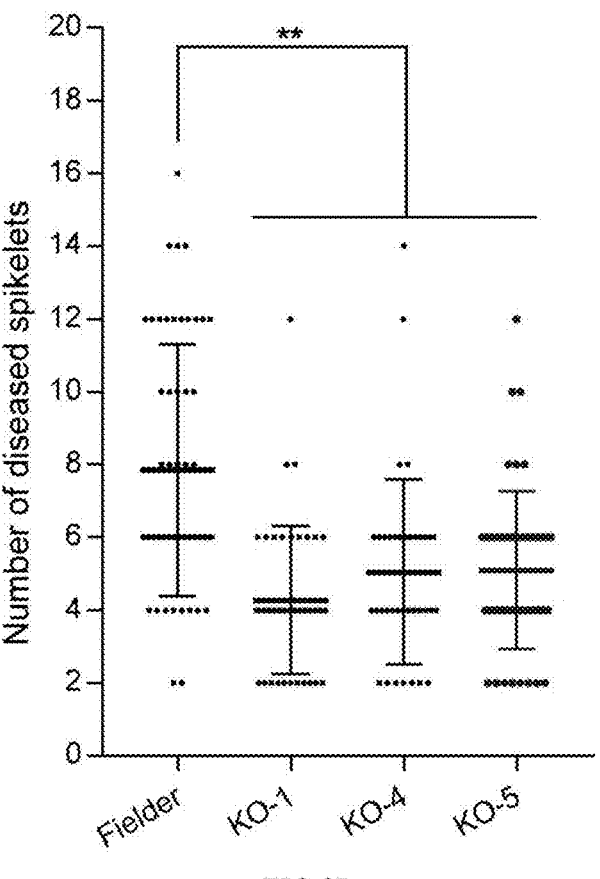

The number of diseased spikelets and the significance of differences of the test plants showed that the FHB infection of the wild-type material Fielder had expanded to the whole spike or half a spike, while the FHB infection of the homozygous mutant strain with three copies of TaCIPK14 knocked out simultaneously in the wheat A, B, and D genomes, including KO-1, KO-4, and KO-5, had expanded by only less than half a spike or very little. Statistical analysis of the significance of differences showed that the average number of diseased spikelets in inoculated spikelets was significantly lower ($P<0.05$) in the homozygous mutant strains (KO-1, KO-4, and KO-5) in which all three copies of TaCIPK14 were knocked out simultaneously in the wheat A, B, and D genomes, as compared to the wild-type material, Fielder. The schematic diagram of TaCIPK14 gene-edited plants inoculated with FHB pathogen showing resistance to the disease is shown in FIGS. 8A-8B. It is proved that TaCIPK14 gene-edited plants showed strong resistance to FHB pathogen.

Example 4: Agronomic Trait Analysis

The wild-type recipient variety Fielder and the homozygous mutant strains (KO-1, KO-4 and KO-5) with three copies of TaCIPK14 knocked out simultaneously in the wheat A, B and D genomes were planted together in the artificial climate chamber at the Southeast Kiln of the College of Plant Protection, Northwest Agriculture and Forestry University. The phenotypes of the above tested edited plants and wild-type plants at seedling stage and the filling stage, main spike at the maturity stage, and grain length and width of grains at the maturity stage were observed, and the main agronomic traits were counted. The statistical results are shown in Table 5. The observation results showed that, compared with the wild-type Fielder, the homozygous mutant strains (KO-1, KO-4, and KO-5) with the three copies of TaCIPK14 simultaneously knocked out in the wheat A, B, and D genomes did not show significant changes in plant morphology at the seedling and filling stages, as well as in the morphology of the spike and the grain at the maturity stage. Statistical analyses showed that there were no significant differences in plant height, flag leaf length, spike length, grain number per spike, grain length, grain width, and thousand-grain weight in the homozygous mutant strains (KO-1, KO-4, and KO-5) in which all three copies of TaCIPK14 were knocked out simultaneously in the A, B, and D genomes of wheat, as compared to those of the wild-type Fielder. This indicates that the wheat TaCIPK14 gene is involved as a susceptibility gene in wheat susceptibility to FHB, the TaCIPK14 knockout mutant has significantly improved resistance to wheat FHB, the TaCIPK14 knockout mutant maintains major agronomic traits, and the wheat TaCIPK14 gene editing material can be used as a new germplasm material that can be used for genetic improvement of wheat resistance to FHB. The technical solution of the present disclosure provides a practical method for realizing rapid wheat breeding and improving wheat disease resistance by genetic engineering technology, which has important breeding application value and broad market application prospect.

TABLE 5

| | Statistical results of agronomic traits | | | | | | |
|---|---|---|---|---|---|---|---|
| | Plant height (cm) | Flag leaf length (cm) | Spike length (cm) | Grain number per spike | Grain length (cm) | Grain width (cm) | Thousand-grain weight (g) |
| Fielder | 65.0 ± 6.9 | 19.8 ± 2.2 | 8.9 ± 0.8 | 29.3 ± 4.0 | 0.73 ± 0.03 | 0.33 ± 0.02 | 29.2 ± 1.4 |
| KO-1 | 63.9 ± 5.8 | 19.5 ± 1.6 | 8.8 ± 0.9 | 28.4 ± 4.6 | 0.73 ± 0.02 | 0.32 ± 0.02 | 28.7 ± 1.5 |
| KO-4 | 65.5 ± 5.1 | 20.4 ± 2.1 | 8.9 ± 1.0 | 27.3 ± 5.0 | 0.72 ± 0.03 | 0.33 ± 0.02 | 29.5 ± 1.5 |
| KO-5 | 65.2 ± 6.3 | 20.0 ± 1.9 | 8.7 ± 1.0 | 26.7 ± 3.9 | 0.72 ± 0.04 | 0.33 ± 0.02 | 29.8 ± 1.3 |

INDUSTRIAL APPLICATION

In the present disclosure, TaCIPK14 gene-edited plants of are obtained by *Agrobacterium*-mediated genetic transformation using CRISPR-Cas9 gene editing technology. The TaCIPK14 gene-edited plants are characterized for disease resistance, and it is found that the TaCIPK14 gene-edited plants have significantly improved disease resistance. Wheat TaCIPK14 gene is involved as a susceptibility gene in wheat susceptibility to FHB, and the TaCIPK14-edited wheat plants have significantly improved resistance to FHB, which can be used as new germplasm material for genetic improvement of wheat resistance to FHB.

The present disclosure utilizes CRISPR-Cas9 gene editing technology to simultaneously edit three alleles of TaCIPK14 in wheat, and after the detection of possible off-target genes predicted by Cas-Offinder, it is found that there is no possibility of off-targeting to other genes in TaCIPK14 gene-edited plants. Therefore, TaCIPK14 knockout mutant plants are successfully obtained. The TaCIPK14 knockout mutant showed resistance to inoculation with FHB pathogen, and the results of the evaluation of the major agronomic traits confirm that the TaCIPK14 knockout mutant still maintained the major agronomic traits. As a result, wheat plants with the potential for wheat FHB control are obtained.

What is claimed is:

1. A method for increasing wheat resistance to *Fusarium* Head Blight (FHB), said method comprising knocking out a TaCIPK14 genes to decrease expression and/or activity of TaCIPK14 protein in a wheat plant;
    wherein the TaCIPK14 protein is the TaCIPK14-4A protein of SEQ ID NO:4, the TaCIPK14-4B protein of SEQ ID NO:5, and the TaCIPK14-4D protein SEQ ID NO: 6, and the TaCIPK14 genes comprise the nucleotide sequences of SEQ ID NO:1, SEQ ID NO:2, and SEQ ID NO:3.

2. A method for breeding a wheat variety with improved resistance to *Fusarium* Head Blight (FHB), said method comprising knocking out a TaCIPK14 genes to reduce the expression and/or activity of TaCIPK14 protein in a wheat plant;
    wherein the TaCIPK14 protein is the TaCIPK14-4A protein of SEQ ID NO:4, the TaCIPK14-4B protein of SEQ ID NO:5, and the TaCIPK14-4D protein SEQ ID NO: 6, and the TaCIPK14 genes comprises the nucleotide sequences of SEQ ID NO:1, SEQ ID NO:2, and SEQ ID NO:3.

3. A method for cultivating transgenic wheat with improved resistance to FHB, comprising steps of inhibiting expression of a nucleic acid molecule capable of expressing TaCIPK14 protein in a wheat plant, and obtaining the transgenic wheat with improved resistance to FHB;
    wherein the TaCIPK14 protein comprises TaCIPK14-4A protein of SEQ ID NO: 4, TaCIPK14-4B protein of SEQ ID NO: 5 and/or TaCIPK14-4D protein of SEQ ID NO: 6.

4. The method of claim 3, wherein the inhibiting expression of the nucleic acid molecule capable of expressing TaCIPK14 protein in the wheat plant is achieved by introducing an RNA interference fragment, an RNA interference vector, a homologous recombinant fragment, a homologous recombinant vector, or a gene editing tool into the wheat plant.

5. The method of claim 4, wherein the gene editing tool is a CRISPR/Cas9 system, wherein a target sequence of the gRNA comprises SEQ ID NO: 7 and/or SEQ ID NO: 8.

6. The method of claim 3, wherein the nucleic acid molecule capable of expressing the TaCIPK14 protein is nucleic acid molecule A, nucleic acid molecule B and/or nucleic acid molecule C;

wherein the nucleic acid molecule A is capable of expressing the TaCIPK14-4A protein; the nucleic acid molecule B is capable of expressing the TaCIPK14-4B protein; and the nucleic acid molecule C is capable of expressing the TaCIPK14-4D protein;
the nucleic acid molecule A is
DNA molecule set forth in SEQ ID NO: 1;
the nucleic acid molecule B is
DNA molecule set forth in SEQ ID NO: 2;
and
the nucleic acid molecule C is
DNA molecule set forth in SEQ ID NO: 3.

7. The method of claim 3, wherein pathogen of the FHB is *Fusarium graminearum*.

8. The method of claim 7, wherein the pathogen of the FHB is a wild-type strain *F. graminearum* PH-1.

9. The method of claim 6, wherein the inhibiting expression of the nucleic acid molecule capable of expressing the TaCIPK14 protein in the wheat is achieved by introducing an RNA interference fragment, an RNA interference vector, a homologous recombinant fragment, a homologous recombinant vector, or a gene editing tool into the wheat plant.

10. The method of claim 3, wherein inhibiting expression of a nucleic acid molecule capable of expressing TaCIPK14 protein in a wheat plant is achieved by introducing an RNA interference fragment, an RNA interference vector, a homologous recombinant fragment, a homologous recombinant vector, or a gene editing tool into the wheat plant.

11. The method of claim 3, wherein the expression is inhibited by gene editing with a CRISPR/Cas9 system, wherein a target sequence of the gRNA comprises SEQ ID NO:7 and/or SEQ ID NO:8.

12. The method of claim 7, wherein the inhibiting expression of the nucleic acid molecule capable of expressing the TaCIPK14 protein in the wheat plant is achieved by introducing an RNA interference fragment, an RNA interference vector, a homologous recombinant fragment, a homologous recombinant vector, or a gene editing tool into the wheat plant.

13. The method of claim 7, wherein the gene editing tool is a CRISPR/Cas9 system, wherein a target sequence of the gRNA comprises SEQ ID NO: 7 and/or SEQ ID NO: 8.

* * * * *